(12) United States Patent
Wanker et al.

(10) Patent No.: US 6,905,818 B1
(45) Date of Patent: Jun. 14, 2005

(54) METHOD FOR THE IDENTIFICATION AND CHARACTERIZATION OF INTERACTING MOLECULES BY AUTOMATED INTERACTION MATING

(75) Inventors: Erich Wanker, Berlin (DE); David Bancroft, Gilching (DE); Hans Lehrach, Berlin (DE); Niels Wedemeyer, Norwalde (DE); Elmar Maier, Schäftlam (DE); Sebastian Meier-Ewert, Gelting (DE)

(73) Assignee: Max-Planck-Gesellschaft zur Forderungder Wissenschaften, Munich (DE)

( * ) Notice: Subject to any disclaimer, the term of this patent is extended or adjusted under 35 U.S.C. 154(b) by 326 days.

(21) Appl. No.: 09/583,066

(22) Filed: May 30, 2000

Related U.S. Application Data

(63) Continuation-in-part of application No. PCT/EP98/07657, filed on Nov. 27, 1998.

(30) Foreign Application Priority Data

Nov. 27, 1997 (EP) ............................................. 97120867
Nov. 27, 1997 (EP) ............................................. 97120879
Nov. 27, 1997 (EP) ............................................. 97120880

(51) Int. Cl.$^7$ ........................... C12Q 1/68; C12Q 1/00; C12Q 1/02; C12P 21/06; C12N 15/00

(52) U.S. Cl. ............................... 435/6; 435/4; 435/29; 435/69.1; 435/440

(58) Field of Search ...................... 435/4, 6, 29, 69.1, 435/440; 514/2, 44

(56) References Cited

U.S. PATENT DOCUMENTS

| | | | |
|---|---|---|---|
| 4,657,858 A | | 4/1987 | Davison |
| 4,981,783 A | * | 1/1991 | Augenlicht ..................... 435/6 |
| 5,283,173 A | * | 2/1994 | Fields et al. ................... 435/6 |
| 5,569,588 A | | 10/1996 | Ashby et al. ................... 435/6 |

FOREIGN PATENT DOCUMENTS

| | | |
|---|---|---|
| EP | 0 790 304 A1 | 8/1997 |
| WO | WO 96/32503 | 10/1996 |
| WO | WO 97/23609 | 7/1997 |
| WO | WO 97/31112 | 8/1997 |
| WO | WO 97/47763 | 12/1997 |
| WO | WO 98/07845 | 2/1998 |

OTHER PUBLICATIONS

Arkin et al., Bio/Technology, vol. 8, pp. 746–749 (1990).*
Yang et al., Bio/Technology, vol. 6, pp. 939–942 (1988).*
Brent et al., "Understanding Gene and Allele Function with Two–Hybrid Methods," Annual Review of Genetics, vol. 31, pp. 663–704 (1997).

Tsukamoto, Y. et al. Effects of Mutations of RAD50, RAD51, RAD52, and Related Genes on Illegitimate Recombination in *Saccharomyces cerevisiae*. Genetics 142, 383–391 (Feb. 1996).
Allen, J. et al., "Finding Prospective Partners in the Library: The Two–hybrid System and Phage Display find a Match", TIBS 20:511–516 (1995).
Anderson, M. et al., "Simultaneous Fluorescence–Activated Cell Sorter Analysis of Two Distinct Transcriptional Elements Within a Single Cell Using Engineered Green Fluorescent Proteins", Proc. Natl. Acad. Sci. USA 93: 8508–8511 (Aug. 1996).
Barillot, E. et al., "Theoretical Analysis of Library Screening Using a N–Dimensional Pooling Strategy", Nucleic Acids Research 19(22):6241–6247 (1991).
Bartel, P. et al., "Elimination of False Positive That Arise in Using the Two–Hybrid System", BioTechniques 14(6): 920–924 (1993).
Bartel, P. et al., "A Protein Linkage Map of *Escherichia coli* Bacteriophage T7", Nature Genetics 12: 72–77 (Jan. 1996).
Bendixen, C. et al., "A Yeast Mating–Selection Scheme for Detection of Protein–Protein Interactions", Nucleic Acids Research 22(9): 1778–1779 (1994).
Benton, David, "Bioinformatics—Principles and Potential of a New Multidisciplinary Tool", Trends in Biotechnology 14: 261–272 (1996).
Boeke, J. et al., "A Positive Selection for Mutants Lacking Orotidine–5'–phosphate Decarboxylase Activity in Yeast: 5–fluoro–orotic Acid Resistance", Gen. Genet. 197: 345–346 (1984).
Breeden, L. and Nasmyth, K., "Regulation of the Yeast HO Gene", Cold Spring Harbor Symp. Quant. Biol. 50: 643–650 (1985).
Chen, Claudia and Okayama, H., "High–Efficiency Transformation of Mammalian Cells by Plasmid DNA", Molecular and Cellular Biology 7(8): 2745–2752 (Aug. 1987).
Cubitt, A. et al., "Understanding, Improving and Using Green Fluoresecnt Proteins", TIBS20:448–455 (Nov. 1995).
Dang, C. et al., "Intracellular Leucine Zipper Interactions Suggest c–Myc Hetero–Oligomerization", Molecular and Cellular Biology 11(2): 654–962 (Feb. 1991).

(Continued)

*Primary Examiner*—Ardin H. Marschel
(74) *Attorney, Agent, or Firm*—Ropes & Gray LLP

(57) ABSTRACT

The present invention relates to an improved method for the identification and optionally the characterisation of interacting molecules designed to detect positive clones from the rather large numbers of false positive clones isolated by conventional two-hybrid systems. The method of the invention relies on a novel combination of selection steps used to detect clones that express interacting molecules from false positive clones. The present invention provides for high-throughput interaction screens for the reliable identification of interacting molecules, which in turn can lead to the identification of substances inhibiting said interactions. Such inhibitors can find their use in the formulation of a pharmaceutical composition. The present invention further relates to kits useful for carrying out the method of the invention.

76 Claims, 29 Drawing Sheets

OTHER PUBLICATIONS

DeRisi, J. et al., "Use of a cDNA Microarray to Analyse Gene Expression Patterns in Human Cancer", Nature Genetics 14: 457–460 (1996).

Dove, S. et al., "Activation of Prokaryotic Transcription Through Arbitrary Protein–Protein Contacts", Nature 386: 627–629 (Apr. 10, 1997).

Drmanac et al.; "Sequencing of Megabase Plus DNA by Hybridization: Theory of the Method", Genomics 4 : 114–128 (1989).

Fearon, E. et al., "Karoplasmic Interaction Selection Strategy: A General Strategy to Detect Protein–Protein Interactions in Mammalian Cells", Proc. Natl. cad. Sci. USA 89: 7958–7962 (Sep. 1992).

Feinberg, A. and Vogelstein, B., "A technique for Radiolabeling DNA Restriction Endonuclease Fragments to High Specific Activity", Analytical Biochemistry 132:6–13 (1983).

Fields, Stanley and Song, O., "A Novel Genetic System to Detect Protein–Protein Interactions", Nature 340: 245–246 (Jul. 20, 1989).

Fleischmann, R. et al., "Whole–Genome Random Sequencing and Assembly of *Haemophilus influenzae* RD", Science 269: 496–512 (Jul. 28, 1995).

Gietz, A. et al., "Improved Method for High Efficiency Transformation of Intact Yeast Cells", Nucleic Acids Research 20(6): 1425 (1992).

Gossen, Manfred and Bujard, H., "Tight Control of Gene Expression in Mammalian Cells By Tetracyclin–Responsive Promoters", Proc. Natl. Acad. Sci. USA 89: 5547–5551 (Jun. 1992).

Gossen, M. et al., "Transcriptional Activation by Tetracyclines in Mammalian cells", Science 268: 1766–1769 (Jun. 23, 1995).

Graham. F. L., and Smiley, J., "Characteristics of a Human Cell Line Transformed by DNA from Human Adenovirus Type 5", J. Gen. Virol. 36:59–72 (1977).

Graham, F. L. and Van der Eb, A. J., "Transformation of Rat Cells by DNA of Human Adenovirus 5", Virology 54: 5 6–539 (1973).

Gress, T. M. et al., "A Pancreatic Cancer–Specific Expression Profile", Oncogene 13: 1819–1830 (1996).

Guzman, L–M et al., "Tight Regulation, Modulation, and High–Level Expression by Vectors Containing the Arabinose PBAD Promoter", J Bacteriology 177(14): 4121–4130 (Jul. 1995).

Han, Limin and Colicelli, J., "A Human Protein Selected for Interference with Ras Function Interacts Directly with Ras and Completes with Raf1", Molecular and Cellular Biology 15(3): 1318–1323 (Mar. 1995).

Harper J. W. et al., "The p21 Cdk–Interacting Protein Cip1 is a Potent Inhibitor of G1 Cyclin–Dependent Kinases", Cell 75: 805–816 (Nov. 19, 1993).

Hoffmann, Werner, "Molecular Characterization of the CAN1 Locus in *Saccharomyces cerevisiae*", J. Biological Chemistry 260(21): 11831–11837 (1985).

Hoheisel, J. et al., "Use of High Coverage Reference Libraries of *Drosophila melanogaster* for Relational Data Analysis", Mol. Biol. 220:903–914 (1991)

Johnston F. R. et al.; "Autoradiography Using Storage Phosphor Technology", Electrophoresis, 11(5): 353–450 (May 1990).

Kaufer, N. et al., "Cycloheximide Resistance in Yeast: The Gene and Its Protein", Nucleic Acids Research 11(10): 31233135 (Nov. 10, 1983).

Kawaguchi, Y. et al., "CAG Expansions in a Novel Gene for Machado–Joseph Disease at Chromosome 14q32.1", Nature Genetics 8: 221–228 (Nov. 1994).

Li, Joachim J. and Herskowitz, I., "Isolation of ORC6, a Component of the Yeast Origin Recognition Complex by a One–Hybrid System", Science 262: 1870–1874 (Dec. 17, 1993).

Larin, Zoia and Lehrach, H., "Yeast Artificial Chromosomes: An Alternative Approach to the Molecular Analysis of Mouse Developmental Mutations", Genet. Res. 56: 203–208 (1990).

Le Douarin, B. et al., "A New Version of the Two–Hybrid Assay for Detection of Protein–Protein Interactions", Nucleic Acids Research 23(5): 876–878 (1995).

Link, A. et al., "Methods for Generating Precise Deletions and Insertions in the Genome of Wild–type *Escerichia coli*: Application to Open Reading Frame Characterization", J. Bacteriology 179(20): 6228–6237 (Oct. 1997).

Liu, J. et al., "Large–Scale Cloning of Human Chromosome 2–Specific Yeast Articicial Chromosomes (YACs) Using and Interspersed Repetitive Sequences (IRS)–PCR Approach", Genomics 26: 178–191 (1995).

Meier–Ewert, S. et al., "An Automated Approach to Generating Expressed Sequence Catalogues", Nature 361: 375–376 (Jan. 28, 1993).

Murphy, C. et al., "A Double Counter–Selection for the Study of Null Alleles of Essential Genes in *Escherichia coli*", Gene 155: 1–7 (1995).

Pansegrau, W. et al., "Nucleotide Sequence of the Kanamycin Resistance Determinant of Plasmid RP4: Homology to ofhter Aminoglycoside 3'–Phosphotansferases", Plasmid 18:193–204 (1987).

Probst, M. et al., "Two Murine Homologs of the Drosophila Single–minded Protein That Interact with the Mouse Aryl Hyrdocarbon Receptor Nuclear Translocator Protein", J. Biol. Chem. 272(7): 4451–4457 (Feb. 14, 1997).

Putz, U. et al., "A Tri–Hybrid System for the Analysis and Detection of RNA_protein Interactions", Nucleic Acids Research 24(23): 4838–4840 (1996).

Ray, B. et al., "Heteroduplex Formation and Mismatch Repair of the "Stuch" Mutation During Mating–type Switching in *Saccharomyces cerevisae*", Mol. Cell. Biol. 11(10):5372–5380 (Oct. 1991).

Redemann, N. et al., "Anti–Oncogenic Activity of Signalling–Defective Epidermal Growth Factor Receptor Mutants", Mol. Cell. Biol. 12(2): 491–498 (Feb. 1992).

Sadowski, I. Et al., "GAL Fusion Vectors for Expression in Yeast or Mammalian Cells", Gene 118: 137–141 (1989).

Sadowski, I. And Ptashne, M., "A Vector for Expressing GAL4(1–147) fusions in Mammalian Cells", Nucleic Acids Research 17(18):7539 (1989).

Schiestl H. R. and Gietz D. R.; "High Efficiency Transformation of Intact Yeast Cells Using Single Stranded Nucleic Acids as a Carrier", Current Genetics, 16(5/6): 339–346 (Dec. 1989).

Schober, A. et al., "Accurate High–Speed Liquid Handling of Very Small Biological Samples", BioTechniques 15(2): 324–329 (1993).

SenGupta, D. et al., "A Three–Hybrid System to Detect RNA–Protein Interactions in vivo", Proc. Natl. Acad. Sci. USA 93: 8496–8501 (Aug. 1996).

Shalon et al.; "A DNA Microarray System for Analyzing Complex DNA Samples Using Two–Color Fluorescent Probe Hybridization", Genome Research, 6(7): 639–645 (Jul. 1996).

Vidal, M. et al., "Reverse Two–Hybrid and One–Hybrid Systems to Detect Dissociation of Protein–Protein and DNA–Protein Interactions", Proc. Natl. Acad. Sci. USA 93: 10315–10320 (Sep. 1996).

Wanker, E. et al., "HIP–I: A Huntingtin Interacting Protein Isolated by the Yeast Two–Hybrid System", Human Mol. Genet. 6(3): 487–495 (1997).

Wu, L. et al., "Identification of a Ring Protein That Can Interact in vivo with the BRCA1 Gene Product", Nature Genetics 14: 430–440 (Dec. 1996).

Yang, M. et al., "Protein–Peptide Interactions Analyzed with the Yeast Two–Hybrid System", Nucleic Acids Research 23(7): 1152–1156 (1995).

Yang, T. et al., "Optimized Codon Usage and Chromophore Mutations Provide Enhanced Sensitivity with the Green Fluorescent Protein", Nucleic Acids Research 24(22): 4592–4593 (1996).

Zhang, J. and Lauter, S., "A Yeast Three–Hybrid Method to Clone Ternary Protein Complex Components", Anal. Biochemistry 242: 68–72 (1996).

* cited by examinerb
a) TCG A|GT CGA C|GC GGC CGC|TAA|CCG G
      *Sal* I        *Not* I      STOP
b) TCG AG|G TCG AC|G CGG CCG C|AG |TAA|CCG G
       *Sal* I        *Not* I          STOP
c) TCG AGA |GTC GAC|GCG GCC GC|T |TAA|CCG G
            *Sal* I       *Not* I         STOP
Figure 4 (II) ↑
Figure 5 ↓
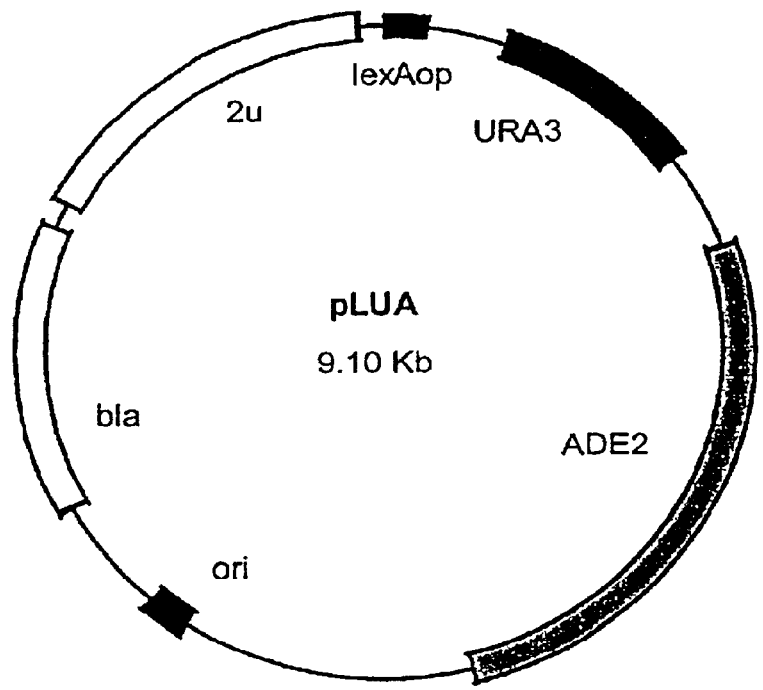

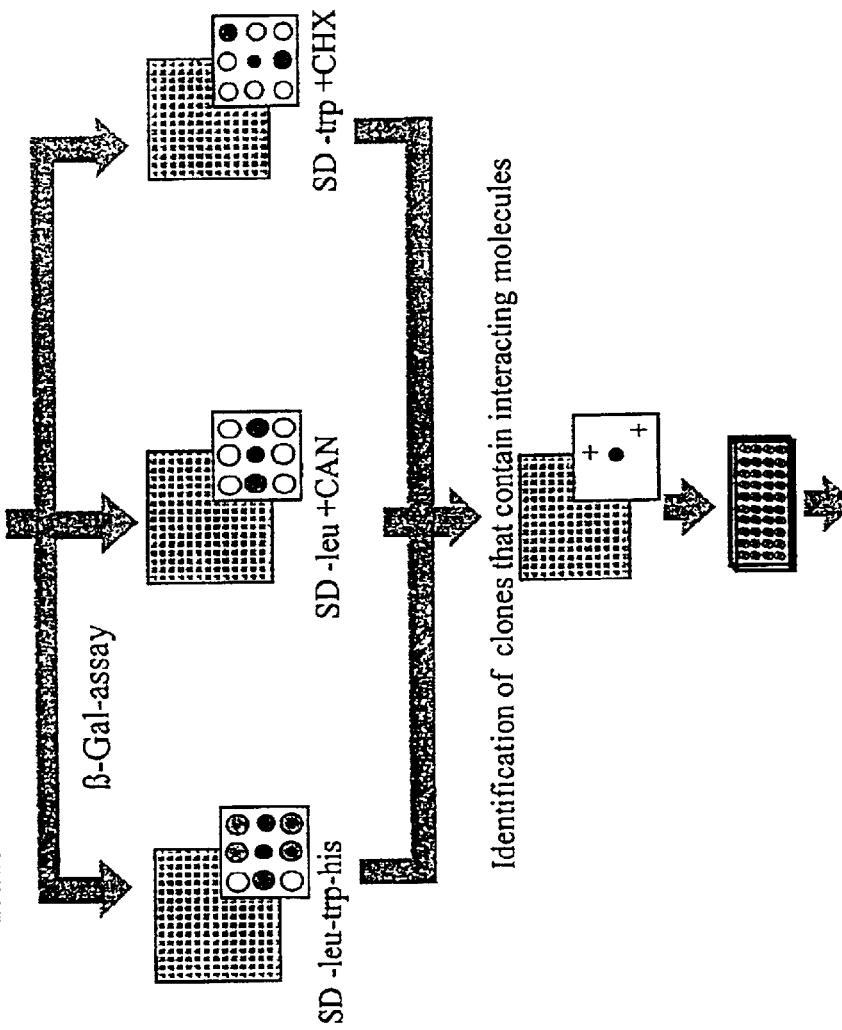
Figure 6 (II)

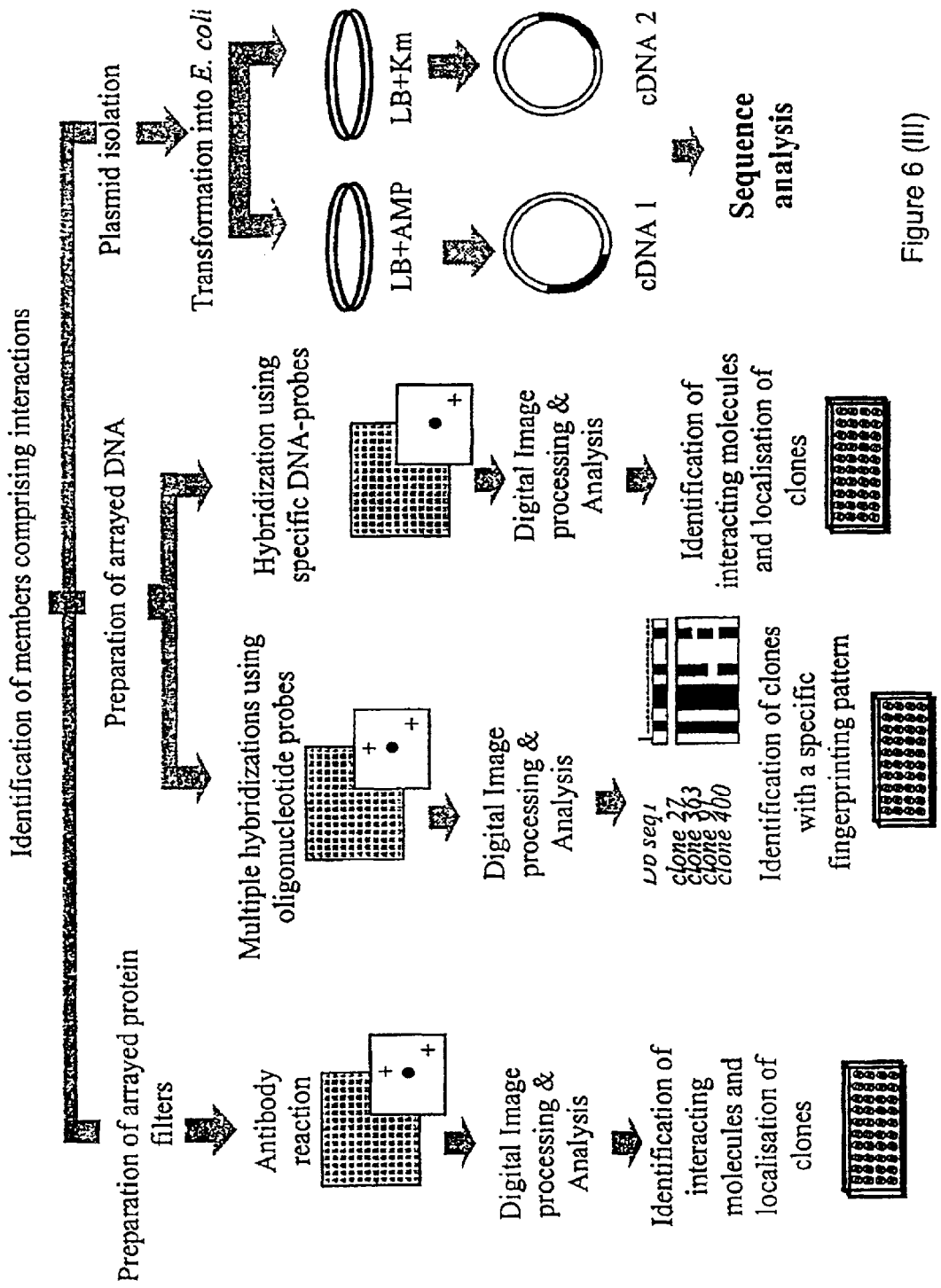
Figure 6 (III)

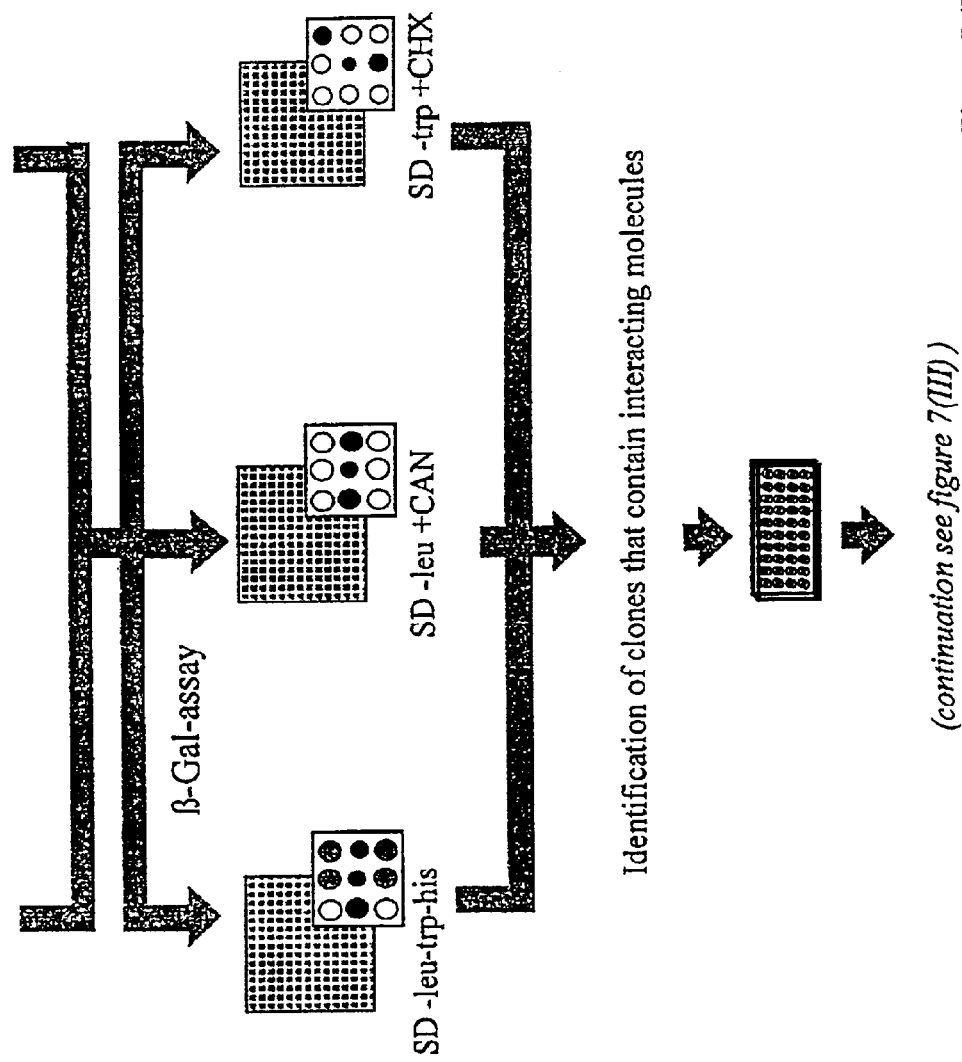
Figure 7 (II)

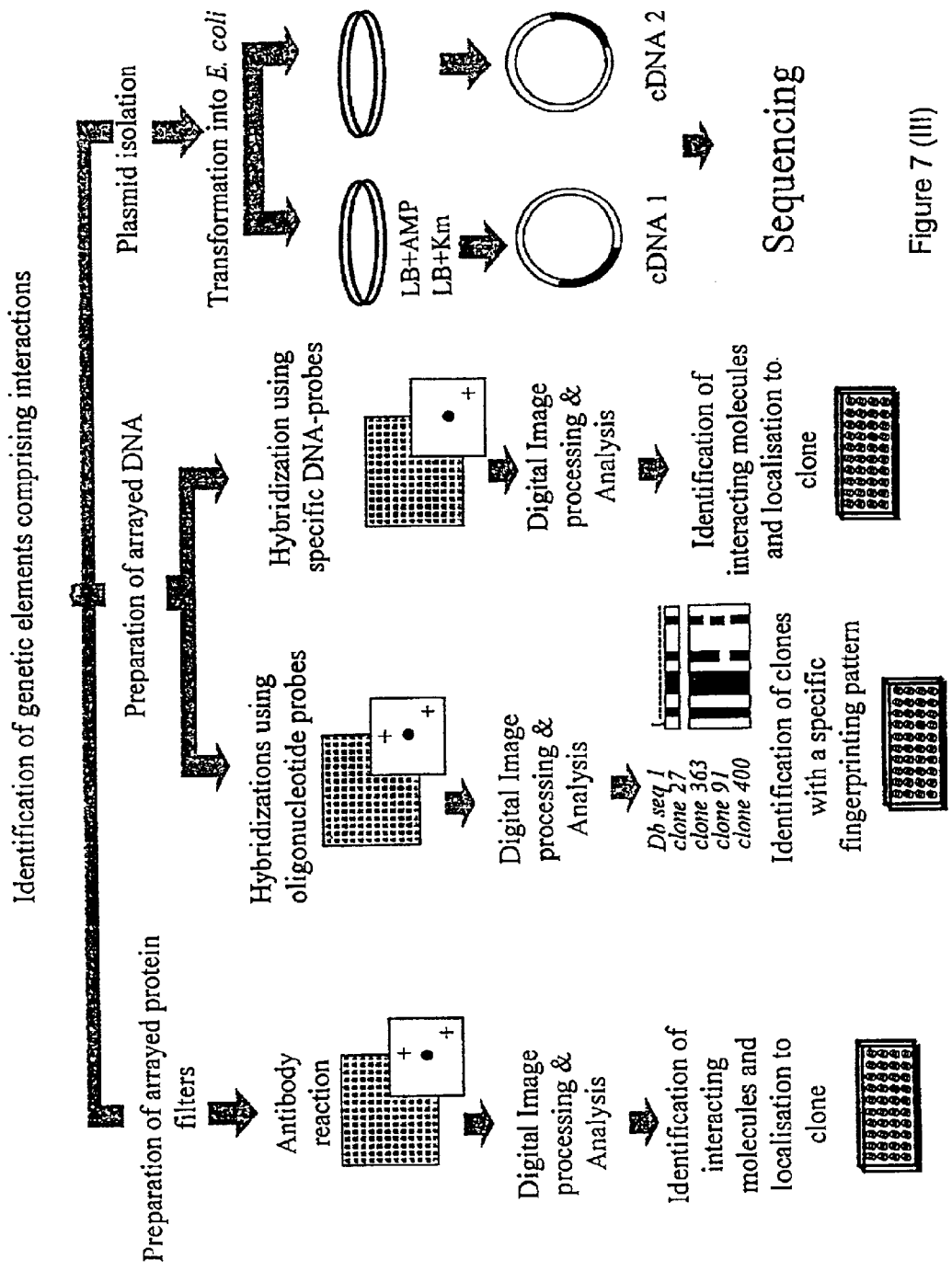
Figure 7 (III)

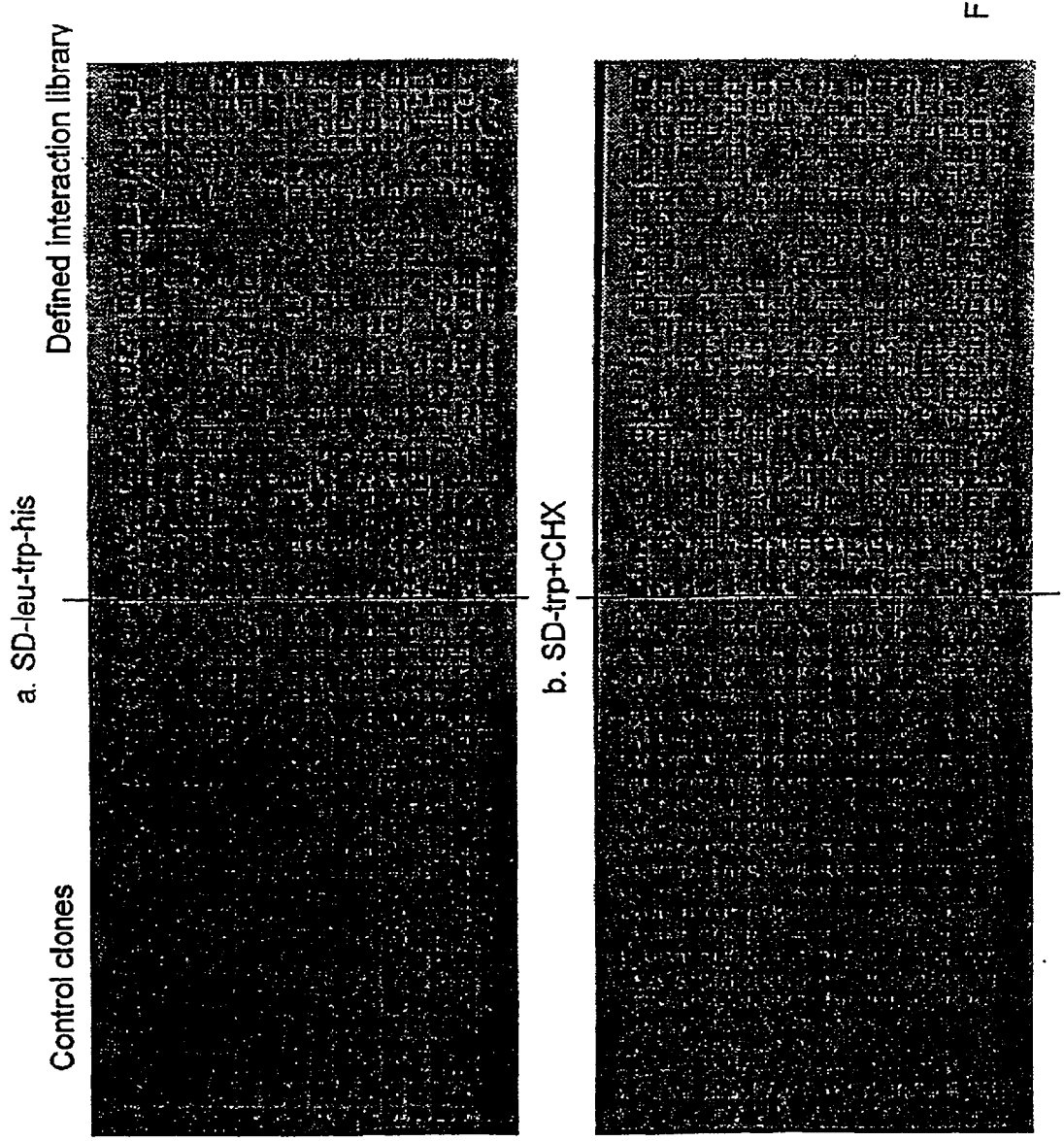

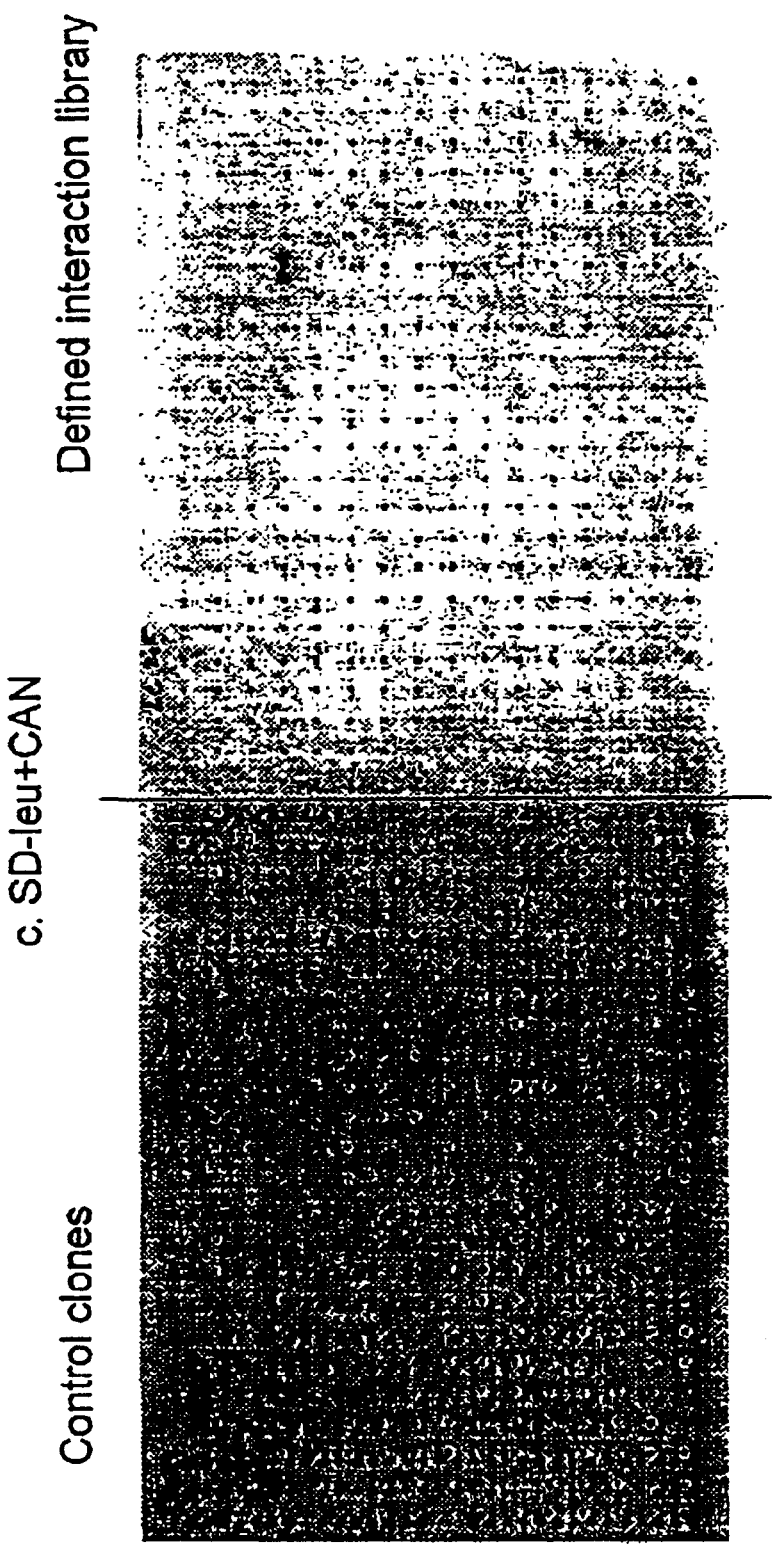
Figure 10 (II)

a.

| | Clone | SD-leu-trp-his | SD-trp+CHX | SD-leu+CAN |
|---|---|---|---|---|
| 675 | 2O8 | 2 | 0 | 0 |
| 687 | 2O22 | 2 | 0 | 0 |
| 689 | 2P1 | 3 | 0 | 0 |
| 690 | 2P2 | 2 | 0 | 0 |
| 693 | 2P5 | 3 | 0 | 0 |
| 696 | 2P8 | 3 | 0 | 0 |
| 699 | 2P12 | 3 | 0 | 0 |
| 709 | 2P23 | 2 | 0 | 0 |
| 710 | 2P24 | 2 | 0 | 0 |
| 711 | 3A2 | 3 | 0 | 0 |
| 712 | 3A3 | 3 | 0 | 0 |
| 713 | 3A4 | 3 | 0 | 0 |
| 714 | 3A5 | 3 | 0 | 0 |
| 716 | 3A7 | 3 | 0 | 0 |
| 717 | 3A8 | 3 | 0 | 0 |
| 718 | 3A11 | 3 | 0 | 0 |
| 719 | 3A12 | 2 | 0 | 0 |
| 720 | 3A14 | 3 | 0 | 0 |
| 721 | 3A15 | 3 | 0 | 0 |
| 722 | 3A18 | 2 | 0 | 0 |
| 723 | 3A21 | 2 | 0 | 0 |
| 724 | 3A23 | 2 | 0 | 0 |
| 725 | 3A24 | 3 | 0 | 0 |
| 727 | 3B2 | 3 | 0 | 0 |
| 728 | 3B3 | 3 | 0 | 0 |
| 729 | 3B4 | 3 | 0 | 0 |
| 730 | 3B5 | 3 | 0 | 0 |
| 731 | 3B6 | 3 | 0 | 0 |
| 732 | 3B7 | 3 | 0 | 0 |
| 733 | 3B8 | 3 | 0 | 0 |
| 734 | 3B9 | 3 | 0 | 0 |
| 735 | 3B10 | 3 | 0 | 0 |
| 736 | 3B12 | 3 | 0 | 0 |
| 737 | 3B13 | 3 | 0 | 0 |
| 738 | 3B14 | 3 | 0 | 0 |
| 739 | 3B15 | 3 | 0 | 0 |
| 741 | 3B17 | 3 | 0 | 0 | b.

| | Clone | SD-leu-trp-his | SD-trp+CHX | SD-leu+CAN |
|---|---|---|---|---|
| 1 | Clone | SD-leu-trp-his | SD-trp+CHX | SD-leu+CAN |
| 1733 | 6L22 | 3 | 0 | 0 |
| 2302 | 8N24 | 2 | 0 | 0 |

Figure 12

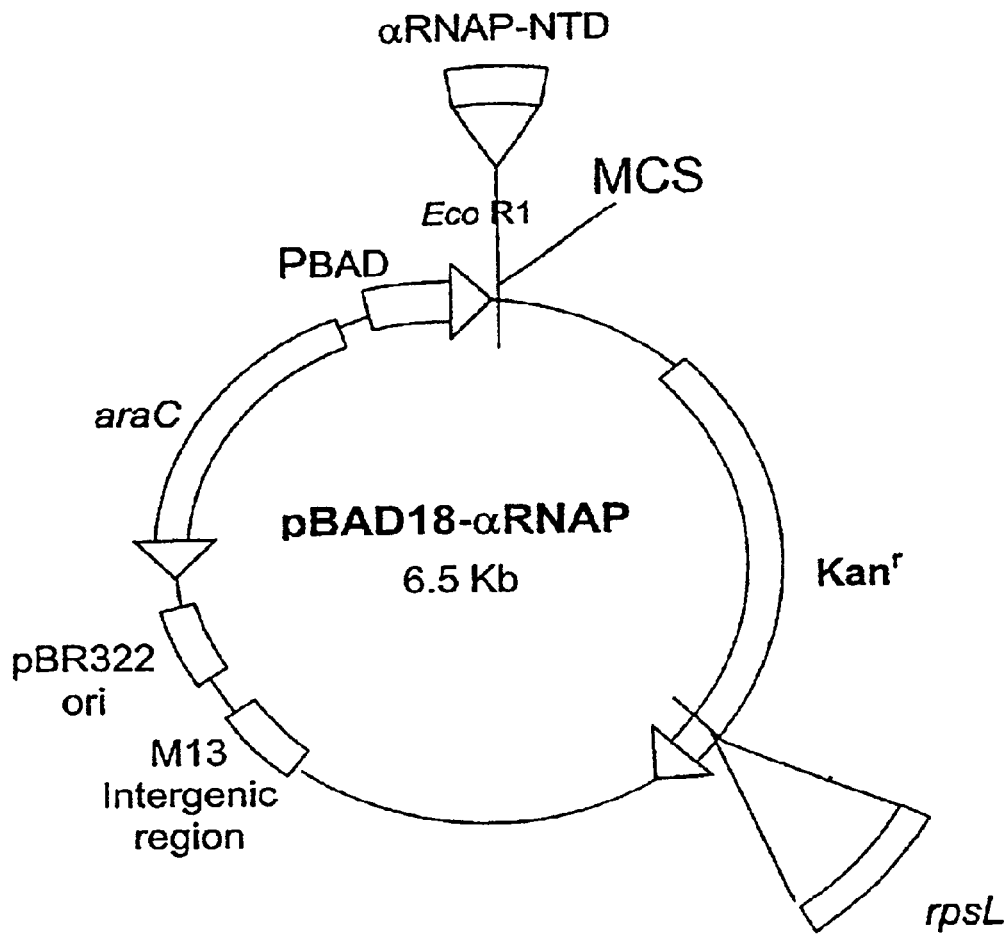
Figure 22 (II)

METHOD FOR THE IDENTIFICATION AND CHARACTERIZATION OF INTERACTING MOLECULES BY AUTOMATED INTERACTION MATING

REFERENCE TO RELATED APPLICATIONS

This application is a continuation-in-part of International Application Ser. No. PCT/EP98/07657, filed 27 Nov. 1998, which claims priority to European Patent Application Ser. Nos. 97120879.8, 97120867.3 and 97120880.6, all of which were filed on 27 Nov. 1997. The specifications of each of the above-referenced patent applications are incorporated by reference herein.

BACKGROUND OF THE INVENTION

The present invention relates to an improved method for the identification and optionally the characterisation of interacting molecules designed to detect positive clones from the rather large numbers of false positive clones isolated by conventional two-hybrid systems. The method of the invention relies on a novel combination of selection steps used to detect clones that express interacting molecules from false positive clones. The present invention provides for high-throughput interaction screens for the reliable identification of interacting molecules, which in turn can lead to the identification of substances inhibiting said interactions. Such inhibitors can find their use in the formulation of a pharmaceutical composition. The present invention further relates to kits useful for carrying out the method of the invention.

Protein-protein interactions are essential for nearly all biological processes like replication, transcription, secretion, signal transduction and metabolism. Classical methods for identifying such interactions like co-immunoprecipitation or cross-linking are not available for all proteins or may not be sufficiently sensitive. Said methods further have the disadvantage that only by a great deal of energy, potentially interacting partners and corresponding nucleic acid fragments or sequences may be identified. Usually, this is effected by protein sequencing or production of antibodies, followed by the screening of an expression-library.

An important development for the convenient identification of protein—protein interactions was the yeast two-hybrid (2H) system presented by Fields and Song (1989). This genetic procedure not only allows the rapid demonstration of in vivo interactions, but also the simple isolation of corresponding nucleic acid sequences encoding for the interacting partners. The yeast 2H system makes use of the features of a wide variety of eukaryotic transcription factors which carry two separable functional domains: one DNA binding domain as well as a second domain which activates the RNA-polymerase complex (activation domain). In the classical 2H system a so-called "bait" protein comprising of a DNA binding domain (GAL4bd or lex A) and a protein of interest "X" are expressed as a fusion protein in yeast ("bait hybrid"). The same yeast cell also simultaneously expresses a so called "fish" protein comprising of an activation domain (GAL4ad or VP16) and a protein "Y" ("fish hybrid"). Upon the interaction of a bait protein with a fish protein, the DNA binding and activation domains of the fusion proteins are brought into close proximity and the resulting protein complex triggers the expression of the reporter genes, e.g. HIS3 or lacZ. Said expression can be easily monitored by cultivation of the yeast cells on selective medium without histidine as well as upon the activation of the lacZ gene. The genetic sequence encoding, for example, an unknown fish protein, may easily be identified by isolating the corresponding plasmid and subsequent sequence analysis. Meanwhile, a number of variants of the 2H system have been developed. The most important of those are the "one hybrid" system for the identification of DNA-binding proteins, the "tri-hybrid" system for the identification of RNA-protein-interactions, the "reverse two hybrid" system, and some systems transferring the 2H approach to cellular systems other than yeast, namely bacterial and mammalian (Li and Hershowitz, 1993; SenGupta et al., 1996; Plutz et al., 1996; Vidal et al., 1996; Dove et al., 1997; Fearon et al., 1992). It should be noted that some 2H systems do not utilise a transactivation approach. For example, the functional reconstitution of enzymatic activity.

The classical 2H system for the identification of protein—protein-interaction, has, until today, only been carried out on a laboratory scale. Although recent developments have taken on the challenges in large scale 2H screening (e.g. Bartel et al., 1996), a successful large scale search of interacting proteins, for example on the basis of a library vs. library screen, has not been reported. However, on the laboratory scale, it is only possible to screen for interactions between gene products which are known and/or which are suspected to interact, as the probability of finding an interaction by random chance is less than $10^{-3}$. The true power of the 2H system, namely finding previously unsuspected interactions, and even interactions between previously unknown proteins and protein families, in screening whole genomes, can only be brought forward in a large scale approach.

One major difficulty in implementing large scale 2H systems lies in eliminating the large numbers of false positives not representing any biologically meaningful interactions between binding partners. In currently applied 2H systems, in which proteins of interest, optionally encoded by cDNA libraries, are fused to a DNA binding domain and an activation domain, respectively, false positives may arise by several different mechanisms:

A peptide or protein cloned into the bait hybrid might itself have activating properties, activating transcription of a reporter gene independent of an interaction with the fish hybrid (herein: "False Positives Class 1").

A peptide or protein cloned into the fish hybrid might itself constitute a DNA binding domain, binding to the DNA binding site or to the basal portion of the promoter, activating transcription of a reporter gene independent of an interaction with the bait hybrid (herein: "False Positives Class 2").

A peptide or protein cloned into the fish hybrid might specifically bind to the DNA binding domain of the bait hybrid, or, vice versa, a peptide or protein cloned into the bait hybrid might specifically bind to the activation domain of the fish hybrid, reconstituting activation of the reporter gene independent of an interaction between the bait and fish proteins. This may include binding to epitope tags fused to the DNA binding domain or activation domain (herein: "False Positives Class 3").

Certain peptides or proteins are able to bind non-specifically to many different other structures (commonly denoted: "Sticky Proteins"). These will result in a large number of positives with one common genetic element.

A number of strategies have been previously described which remove some of the above classes of false positives (Allen et al., 1995; Bartel et al., 1993).

The use of two reporter genes (Bartel et al., 1993): One of these genes usually expresses a selectable marker (e.g.

HIS3) and the other reporter gene a measurable marker activity (e.g. lacZ), and the reporter gene promoters usually are different. By scoring positives according to activation of both reporter genes, this allows removal of a certain part of the False Positives Class 2 since an interaction with both of the different promoters is less likely to occur.

The use of selectable markers and preselection (Bartel et al., 1996): This method employs replica plating of yeast clones that express one fusion protein from plates containing selective medium corresponding to the selectable marker introduced with the plasmid that encoded said one fusion protein to plates containing selective medium corresponding to a reporter gene product (e.g. LEU2 as selectable marker on plasmid, HIS3 as reporter gene). Yeast clones that showed growth on selective medium corresponding to the reporter gene product where identified as False Positives Class 1 or Class 2, respectively, and were subsequently not used for interaction mating.

The use of counterselectable genes and preselection (Vidal et al., 1996a): Two populations of mating competent yeast host cells of different mating type are provided that contain (a) the bait hybrid plasmid and one counterselectable reporter gene in the population of cells of the first mating type, and (b) the fish hybrid plasmid and the same or another counterselectable reporter gene in the population of cells of the second mating type. When these first and second populations are kept individually under conditions such that expression of said counterselectable reporter gene inhibits the growth of said host cells, False Positives Class 1 and False Positives Class 2 are hypothetically removed.

The use of a second, different bait hybrid protein: Several approaches have been described, all of which are performed on positive clones after scoring of positives: (a) curing of the bait hybrid plasmid, transfection with a second bait hybrid plasmid containing an unrelated bait protein fused to the same DNA binding domain as in the original bait hybrid plasmid; expression of the reporter gene(s) indicates False Positives Class 2 as well as a Sticky Protein or False Positive Class 3 being fused to the activation domain (Harper et al., 1993); (b) curing of the bait hybrid plasmid, transfection with a second bait hybrid plasmid containing an unrelated bait protein fused to a different DNA binding domain that binds to a second DNA binding site controlling a second site comprising the reporter gene; expression of the reporter gene indicates a Sticky Protein or certain types of False Positives Class 3 being fused to the activation domain (Le Douarin et al., 1995); (c) transfection with a control hybrid plasmid encoding a fusion protein comprising the bait protein and a second DNA binding domain that binds to a second DNA binding site controlling a second reporter gene; lack of expression of the second reporter gene indicates a False Positive Class 1 (Hurd et al., 1997).

All of these strategies are time and labour consuming, which is particularly inconvenient in cases where large numbers of clones are to be analysed, and, in order to eliminate all false positives, a combination would have to be used, necessitating even more handling steps. An efficient method for the elimination of false positives is, however, inherently more necessary in a library vs. library screen as compared to the screening of one bait protein against a library of fish proteins, because the combination of randomly chosen peptides or proteins/protein fragments with a DNA binding domain is much more likely to be able to auto-activate expression of a reporter gene than randomly chosen peptides or proteins/protein fragments fused to an activation domain. As a consequence, false positive rates of up to 50% would be expected in a library vs. library screen, which, together with the high total number of clones, does render such screen unfeasible with conventional 2H methods.

Moreover, as yeast is not the host cell of choice in a variety of investigations (e.g. when a mammalian protein suspected to interact with a second protein requires substantial post translational modifications), it would be desirable for a high throughput 2H system to be versatile with regard to the type of host cell employed. All systems put forward so far that are geared to eliminate the difficulties of 2H screening, although mostly claiming to be applicable to all types of cells, have been designed towards the specific biological properties of the yeast two hybrid system, and cannot necessarily be transferred to, for example, bacterial or mammalian cell systems.

The technical problem underlying the present invention was therefore to provide a method that allows the fast and reliable elimination of false positives. This method should, moreover, be suitable for large-scale library vs. library screens using a high-throughput approach. Preferably, this method would be applicable to a range of different host cell systems, such as yeast, bacterial, mammalian, plant and insect cells. Such method could routinely be applied to the identification of pathways of molecular interactions in biological systems, and the interconnections between such pathways. Ultimately, the identification of molecules involved in interactions that form part of such pathways can be employed in order to pinpoint targets for pharmaceuticals.

The solution to said technical problem is achieved by providing the embodiments characterised in the claims.

SUMMARY OF THE INVENTION

In a first aspect the present invention relates to a method for the identification of at least one member of a pair or complex of interacting molecules from a pool of potentially interacting molecules, comprising:

(A) providing at least one set of host cells, each set containing at least one genetic element comprising a selectable marker, said selectable marker being different between different sets of host cells, said genetic elements each comprising genetic information specifying one of said potentially interacting molecules, said host cells further carrying a readout system that is activated upon the presence of auto-activating molecules;

(B) selecting against host cells expressing a molecule able to auto-activate the readout system by transferring at least one set of host cells or progeny of at least one set of host cells to at least one selective medium which allows growth of said host cells in the presence of said selectable marker different for each set of host cells and which precludes growth of said host cells upon auto-activation of said readout system;

(C) combining in host cells at least two genetic elements, wherein at least one set of host cells grows on said selective medium specified in (B);

(D) allowing at least one interaction, if any, to occur;

(E) selecting for said interaction by transferring said host cells or progeny of said host cells to a selective medium that allows identification of said host cells upon activation of the readout system;

(F) identifying host cells that contain interacting molecules that activate said readout system on said selective medium;

(G) identifying at least one member of said pair or complex of interacting molecules; wherein said host cells are not yeast cells.

Furthermore, in a second aspect the present invention relates to a method for the identification of at least one member of a pair or complex of interacting molecules from a pool of potentially interacting molecules, comprising:

(A) providing at least one set of host cells, each set containing at least one genetic element comprising a selectable marker, said selectable marker being different between different sets of host cells, said genetic elements each comprising genetic information specifying one of said potentially interacting molecules, said host cells further carrying a readout system that is activated upon the presence of auto-activating molecules;

(B) selecting against host cells expressing a molecule able to auto-activate the readout system by transferring at least one set of host cells or progeny of at least one set of host cells to at least one selective medium which allows growth of said host cells in the presence of said selectable marker different for each set of host cells and visual differentiation between those cells whose readout system has been activated from those host cells whose readout system has not been activated;

(C) combining in host cells at least two different genetic elements, wherein at least one set of host cells grows on said selective medium specified in (B);

(D) allowing at least one interaction, if any, to occur;

(E) selecting for said interaction by transferring said host cells or progeny of said host cells to a selective medium that allows identification of said host cells upon activation of the readout system;

(F) identifying host cells that contain interacting molecules that activate said readout system on said selective medium;

(G) identifying at least one member of said pair or complex of interacting molecules Furthermore, in a third aspect the invention relates to a method for the identification of at least one member of a pair or complex of interacting molecules from a pool of potentially interacting molecules, comprising:

(A) providing at least one set of host cells, each set containing at least one genetic element comprising a selectable marker, said selectable marker being different between different sets of host cell, said genetic elements each comprising genetic information specifying one of said potentially interacting molecules, said host cells further carrying a readout system that is activated upon the presence of auto-activating molecules;

(B) selecting against host cells expressing a molecule able to auto-activate the readout system by transferring at least one set of host cells or progeny of at least one set of host cells to at least one selective medium which allows growth of said host cells in the presence of said selectable marker different for each set of host cells and which precludes growth of said host cells upon auto-activation of said readout system;

(C) combining in host cells at least two genetic elements, wherein at least one set of host cells grows on said selective medium specified in (B);

(D) allowing at least one interaction, if any, to occur, (E) selecting for said interaction by transferring said host cells or progeny of said host cells to a selective medium that allows identification of said host cells upon activation of the readout system;

(F) identifying host cells that contain interacting molecules that activate said readout system on said selective medium;

(G) identifying at least one member of said pair or complex of interacting molecules;

wherein said host cells are yeast cells, and at least one of the steps (B), (C), (E) or (F) is effected or assisted by automation using regular grid patterns of host cells.

Figure 1:
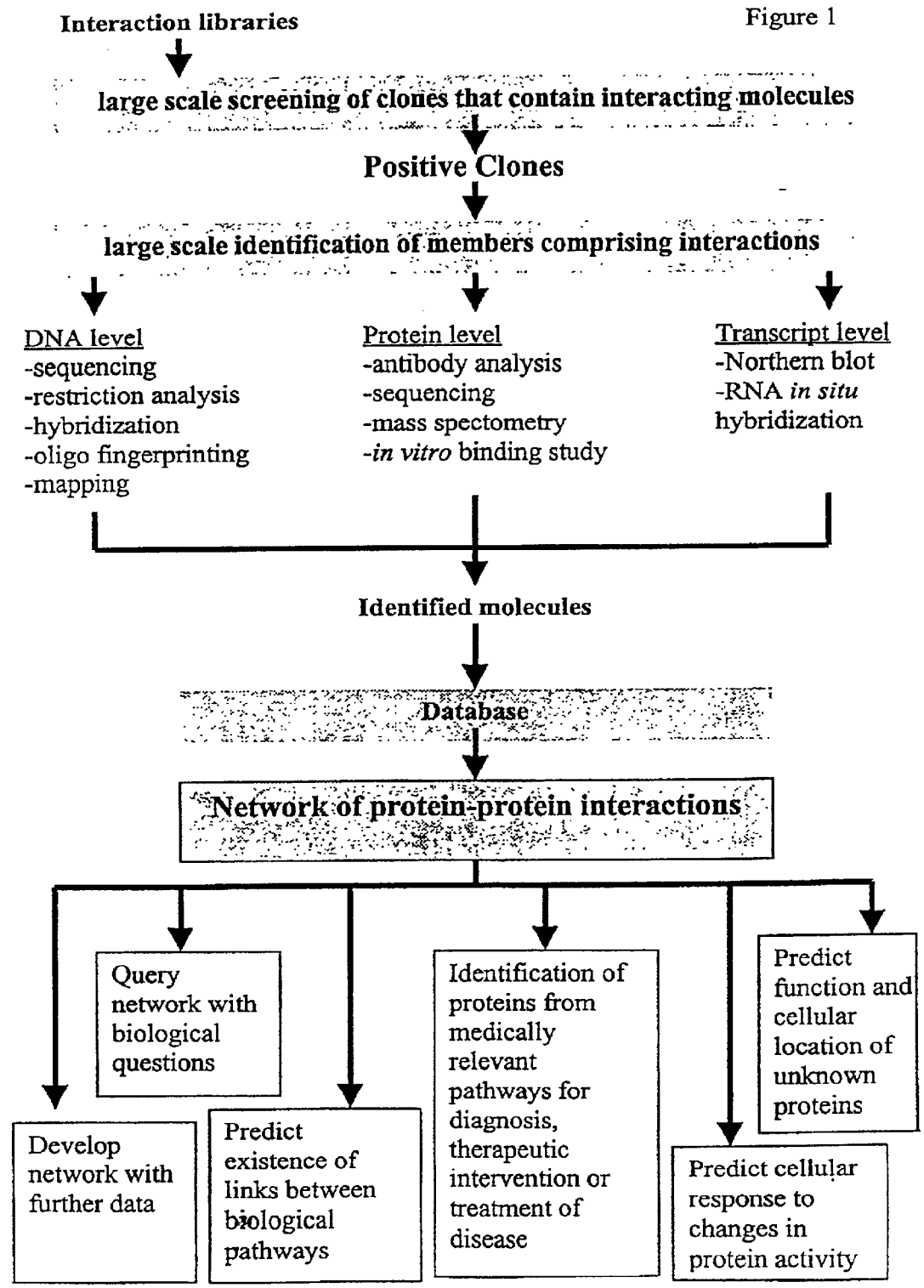
FIG. 1

The applications of an established and exhaustive network of protein—protein interactions. The identity of positive clones and the identity of the members comprising the interactions for the entire interaction library are stored in a database. These data are used to establish a network of protein—protein interactions which can be used for a variety of purposes. For example, to predict the existence of new biological interactions or pathways, or to determine links between biological networks. Furthermore with this method, the function and localisation of previously unknown proteins can be predicted by determining their interaction partners. It also can be used to predict the response of a cell to changes in the expression of particular members of the networks. Finally, these data can be used to identify proteins within a medically relevant pathway which are suitable for therapeutic, diagnosis intervention and for the treatment of disease.

FIG. 2

A scheme and features for a set of data-tables suitable for storing, managing and retrieving data from a large-scale protein—protein interaction screen. The scheme could be implemented in either relational or object-orientated databases. The primary links between table-keys are indicated, as are the suggested fields or elements to be held within each table.

FIG. 3

A process flow representing the experimental and informatic flow during a large-scale protein—protein interaction screen. The figure displays in which part of the experimental steps each table from a the data-base described above is most applicable. Each table forms the underlying data-set from which work-flow management software for that part of the process is based.

FIG. 4

Plasmids Constructed for the Improved 2-Hybrid System.

The plasmid maps of the pBTM118a, b and c DNA binding domain vector series and the pGAD428a, b and c activation domain vector series. Both plasmids contain the unique restriction enzyme sites for Sal I and. Not I which can be used to clone a genetic fragment into the multiple cloning site. The plasmids are maintained in yeast cells by the selectable markers TRP1 and LEU2 respectively. The loss of the plasmids can be selected for by the counterselective markers CAN1 and CYH2 respectively.

Polylinkers used within the multiple cloning site to provide expression of the genetic fragment in one of the three reading frames. (SEQ ID Nos. 1–3)

FIG. 5

The structure of the URA3 readout system carried by the plasmid pLUA. Important features of pLUA include the URA3 gene which is under the transcriptional control of the lexAop-GAL1 promoter, the ADE2 selectable marker that allows yeast ade2-auxotrophs to grow on selective media lacking adenine and the β-lactamase gene (bla) which confers ampicilin resistance in *E. coli*. The pLUA plasmid replicates autonomously both in yeast using the $2\mu$ replication origin and in *E. coli* using the ColE1 origin of replication.

FIG. 6

A schematic overview of one embodiment of the method of the invention. For the parallel analysis of a network of protein—protein interactions using the method of the invention, a library of plasmid constructs that express DNA binding domain and activation domain fusion proteins is provided. These libraries may consist of specific DNA fragments or a multitude of unknown DNA fragments ligated into the improved binding domain and activating domain plasmids of the invention which contain different selectable and counterselectable markers. Both libraries are combined within yeast cells by transformation or interaction mating, and yeast strains that express potentially interacting proteins are selected on selective medium lacking histidine. The selective markers TRP1 and LEU2 maintain the plasmids in the yeast strains grown on selective media, whereas CAN1 and CYH2 specify the counter-selectable markers that select for the loss of each plasmid. HIS3 and lacZ represent selectable markers in the yeast genome, which are expressed upon activation by interacting fusion proteins. The readout system is, in the present case, both growth on medium lacking histidine and the enzymatic activity of β-galactosidase which can be subsequently screened. A colony picking robot is used to pick the resulting yeast colonies into individual wells of 384-well microtiter plates, and the resulting plates are incubated at 30° C. to allow cell growth. The interaction library held in the microtiter plates optionally may be replicated and stored. The interaction library is investigated to detect positive clones that express interacting fusion proteins and discriminate them from false positive clones using the method of the invention. Using a spotting robot, cells are transferred to replica membranes which are subsequently placed onto one of each of the selective media SD-leu-trp-his, SD-leu+CAN and SD-trp+CHX. After incubation on the selective plates, the clones which have grown on the membranes are subjected to a β-Gal assay and a digital image from each membrane is captured with a CCD camera which is then stored on computer. Using digital image processing and analysis clones that express interacting fusion proteins can be identified by considering the pattern of β-Gal activity of these clones grown on the various selective media The individual members comprising the interactions can then be identified by one or more techniques, including PCR, sequencing, hybridisation, oligofingerprinting or antibody reactions.

FIG. 7

A schematic overview of one embodiment of the method of the invention. For the parallel analysis of a network of protein—protein interactions with the method of the invention, two libraries of plasmid constructs that express DNA binding domain or activation domain fusion proteins are provided. These libraries may consist of specific DNA fragments or a multitude of unknown DNA fragments ligated into binding domain and activating domain plasmids which contain the selectable markers TRP1 and LEU2, an doptionally the counterselective markers CAN1 and CYH2 respectively. The libraries are transformed into either Mata or Matα yeast strains containing the URA3 readout system and are subsequently plated onto selective media containing 5-fluoroorotic acid (5-FOA). Only those yeast cells that express fusion proteins unable to auto-activate the URA3 readout system will grow in the presence of 5-FOA. The resulting yeast strains that express only non-auto-activating proteins can then be directly used in an automated interaction mating approach to generate ordered arrays of diploid strains which can be assayed for activation of the lacZ readout system. a) Individual yeast cells that express single fusion proteins unable to activate the URA3 readout system are transferred into wells of a 384-well microtiter plate using a modified picking robot. The yeas strains held in the microtiter plates can optionally be replicated and stored. The microtiter plates contain a growth medium lacking amino acids appropriate to maintain the corresponding plasmids in the yeast strains. The interaction matings are subsequently performed by automatically transferring a Mata and a Matα yeast strain to the same position on a Nylon membrane using automated systems as described by Lehrach et al. (1997). Alternatively, a pipetting or micropipetting system (Schober et al. 1993) can be used to transfer small volumes of individual liquid cultures of a yeast strain onto which a lawn of yeast cells derived from at least one yeast clone of the opposite mating type is sprayed or applied. Yeast strains may be applied singly or as pools of many clones. By both methods ordered arrays of yeast clones are incubated overnight at 30° C. to allow interaction mating to occur. The resulting diploid cells are then analysed in a β-Gal assay as described by Breeden & Nasmyth (1985). b) Yeast strains that grew on selective media containing 5-FOA are pooled and interaction mating between the Mata and Matα strains is made within liquid YPD medium. Those diploid yeast strains that express interacting proteins are selected by plating on selective medium lacking histidine and uracil. The selective markers TRP1 and LEU2 maintain the plasmids in yeast strains grown on selective media HIS3, URA3 and lacZ represent reporter genes in the yeast cells, which are expressed on activation by interacting fusion proteins. The readout system is, in the present case, growth on medium lacking histidine and/or uracil and enzymatic activity of β-galactosidase which can be screened at a later time point. A modified colony picking robot is used to pick the diploid yeast colonies into individual wells of 384-well microtiter plates containing selective medium, and the resulting plates are incubated at 30° C. to allow cell growth. The interaction library optionally may be replicated and stored. Using a spotting robot, diploid cells are transferred to replica membranes which are subsequently placed onto growth medium. Optionally, replica mambranes can be placed on the counterselective media SD–trp+CHX or SD–leu+CAN. The resulting regular arrays of diploid yeast clones are analysed for β-Gal activity as described by Breeden & Nasmyth (1985). In either case a) and b), a digital image from each dried membrane is captured with a CCD camera which is then stored on computer. Using digital image processing and analysis clones that express interacting fusion proteins can be identified by considering the β-Gal activity of these clones spotted in a defined pattern grown the membranes placed on the variious selective media. The individual members comprising the interactions can then be identified by one or more techniques, including PCR, sequencing, hybridisation, oligofingerprinting or antibody reactions.

FIG. 8

Predicted interactions between fusion proteins used to create the defined interaction library. The fusion proteins enclosed with dark rounded boxes are believed to interact as shown. The LexA-HIP1 and GAL4ad-LexA fusion proteins enclosed by thin rectangular boxes have been shown to activate the LacZ readout system without the need for any interacting fusion protein. The two proteins LexA and GAL4ad, and the three fusion proteins GAL4ad-HIPCT, GAL4ad-14-3-3 and LexA-MJD (all unboxed) are believed not to interact with each other or other fusion proteins used in this example.

FIG. 9

Identification of positive clones that contained interacting fusion proteins from false positive clones using the method of the invention. Three different yeast clones each containing pairs of plasmid constructs (positive control: pBTM117c-SIM1 & pGAD427-ARNT; negative control: pBTM117c & pGAD427 and false-positive control: pBTM117c-HIP1 & pGAD427) were transferred by hand to four agar plates each containing a different selective medium (SD-leu-trp, SD-leu-trp-his, SD-leu+CAN and SD-trp+CAN), and incubated for 48 hours at 30° C. The yeast colonies were subsequently transferred to a Nylon membrane and assayed for β-gal activity by the method of Breeden and Nasmyth (1985).

FIG. 10

Digital images of the β-gal assays made from the replica Nylon membranes containing the defined interaction library obtained from the selective media (a) SD-leu-trp-his, (b) SD-trp+CHX and (c) SD–leu+CAN. In each case, The left hand side of each membrane contains control clones and clones from the defined interaction library, and the right hand side contains only clones from the defined interaction library. The two regions marked on the first membrane represent those clones magnified in FIG. 11. The overall size of each membrane is 22×8 cm and contains 6912 spot locations at a spotting pitch of 1.4 mm.

FIG. 11

Magnification of clones from the interaction library taken from the same region of three membranes obtained from the selective media SD-leu-trp-his, SD-trp+CHX and SD-leu+CAN assayed for β-gal activity:

Clones imaged from a region of the right hand side of the membrane containing the defined interaction library. Clones from the defined interaction library that express interacting proteins are ringed and correspond to the microtiter plate addresses 06L22 and 08N24.

Clones imaged from a region of the left hand side of the same membranes containing control clones and clones from the interaction library, where clones around each ink guide-spot are arranged as shown and correspond to: 00 Ink guide spot; 01 False positive control clone that expresses the fusion protein GAL4ad-LexA; 02 False positive clone expressing the fusion protein LexA-HIP1; 03 Positive control clone expressing the interacting fusion proteins LexA-SIM1 & GAL4ad-ARNT; 04 Clone from the defined interaction library. The positive control clone (spot position 03) is ringed.

FIG. 12

A subset of the list of clones identified by computer query of data produced by automated image analysis and quantification of the β-galactosidase activity. Each record represents the 13-galactosidase activity for a given clone grown on three selective media This program queried the data to identify all clones from the interaction library that had activated the reporter gene (score>0) when grown on minimal medium lacking, leucine, trptophan, and histidine (SD-leu-trp-his), yet had not on either of the counterselective media (score on both media equal to 0).

Two positive clones 06L22 and 08N24 characterised by hybridisation are present within the computer file.

FIG. 13

Characterisation by hybridisation of the genetic fragments carried by the clones 06L22 and 08N24. A 1.3 kb, SIM1 and a 1.4 kb ARNT DNA fragment were used as nucleic acid probes for hybridisation to high-density spotted membranes containing DNA from the defined interaction library. These clones were characterised as containing SIM1 and ARNT genetic fragments by hybridisation. The images are of the same region of the membranes as those shown in FIG. 11 a. The spot positions of the clones 06L22 and 08N24 are ringed.

FIG. 14

Identification of the SIM1 and ARNT DNA fragments from the yeast two-hybrid plasmid carried by the clone 06L22 by duplex PCR. Plasmid DNA was isolated from a liquid culture of the clone 06L22 by a QiaPrep (Hilden) procedure and the inserts contained within the plasmids were amplified by PCR using the primer pairs, 5'-TCG TAG ATC TTC GTC AGC AG-3' (SEQ ID No. 4) & 5'-GGA ATT AGC TTG GCT GCA GC-3' (SEQ ID No. 5) for the plasmid pBTM117c and 5'-CGA TGA TGA AGA TAC CCC AC-3' (SEQ ID No. 6) & 5'-GCA CAG TTG AAG TGA ACT TGC-3' (SEQ ID No. 7) for pGAD427. Lane 1 contains a Lamda DNA digestion with BstEII as size marker; Lane 2 contains the duplex PCR reaction from plasmids isolated from clone 06L22; Lanes 3 and contain control PCR amplifications from the plasmids pBTM117c-SIM1 and pGAD427-ARNT respectively.

FIG. 15

Readout system ativation for clones in a regular grid pattern from an interaction library. 23 384-well microtiter plates of the sea urchin interaction library were spotted in a '3×3 duplicate' regular grid pattern around an ink guide-spot on a 222×222 mm porous membrane (Hybond N+, Amersham, UK) using a spotting robot. The membrane was incubated in SD-leu-trp-his medium for 3 days, assayed for lacZ expression using the 13-gal assay as described by Breeden & Nasmyth (1985) and air dried overnight. A digital image was captured using a standard A3 computer scanner.

FIG. 16

Hybridisation of a gene fragment (Probe A) encoding for Protein A to an array of DNA from an interaction library. The probe was labelled radioactively by standard protocols, and hybridisation-positive clones from the interaction library are identified by the automated image analysis system. The position of clone 5K20, from which the gene fragment was isolated, is indicted. Other hybridisation-positive clones also carry this gene-fragment, and by recovery of interacting members from these clones, a protein—protein interaction pathway for Protein A can be uncovered.

FIG. 17

A graphical representation of the hybridisation-positive clones generated by hybridisation of Probe A to a DNA array representing the interaction library.

FIG. 18

A graphical representation of hybridisation- and interaction-positive clones generated by a subsequent hybridisation with probe B (isolated from the clone marked in a grey box). Also shown, are the positions of the hybridisation-positive clones from probe A. Interaction-positive clones that carry both gene fragments are identified as hybridising with both probes.

FIG. 19

A graphical representation of hybridisation- and interaction-positive clones generated by a further hybridisation with probe C isolated from the clone 6D18 (marked by a grey box and "B/C"). Also shown are the hybridisation signals for probes A and B. By considering common hybridisation signals for interaction-positive clones and subsequent DNA sequencing of the inserts carried by these clones, protein—protein interactions can be uncovered. The figure also shows an interaction pathway uncovered between Proteins A, B an C based on these data.

FIG. 20

Automated visual differentiation of yeast cells expressing single fusion proteins able to activate the LacZ readout system. A defined library of L40 ccu yeast clones expressing different fusion proteins cloned in the plasmid pBTM117c was plated onto minimal medium lacking tryptophan, buffered to pH 7.0 with potassium phosphate and containing 2 ug/ml of X-Gal (SD-trp/XGAL). White colonies that have not autoctivated the LacZ reporter gene are automatically recognised and marked with a red horizontal cross. A colony that has turned blue due to expression of a single fusion protein able to auto-activate the LacZ reporter gene is automatically recognised due to its darker colour and the presence of a 'hole'. An arrow indicates this colony. All colonies unsuitable for further analysis and picking (including those too small or touching colonies) are automatically recognised and marked with a blue diagonal cross.

FIG. 21

Results of automated interaction mating to identify diploid yeast strains that express interacting fusion proteins. a) Progeny of the yeast strains x1a and x2a were spotted at positions 1 and 2 on a nylon membrane using a spotting robot such as described by Lehrach et al. (1997). The yeast strains y1α and y2α of the opposite mating type were subsequently spotted on positions 1 and 2 which already contained cells from the strains x1a and x2a. To assist in recognition of the duplicate spotting pattern, ink was spotted in position 2 directly to the right of the spotted yeast clones. b) The membrane was transferred to a YPD agar plate and was incubated at 30° C. overnight to allow interaction mating to occur. c) Diploid yeast cells that had grown on the membrane were subsequently analysed for β-galactosidase activity using the method of Breeden & Nasmyth (1985).

FIG. 22

The two vectors constructed to provide further genetic features to enable the method of invention within a prokaryotic two-hybrid system. The vectors are based on the pBAD series of vectors which provide tight inductive-control of expression of cloned genes using the promoter from the arabinose operon (Guzman et al., 1995 J. Bact. 177: 4141–4130), and can be maintained in the same E. coli cell by virtue of compatible origins of replication.

The plasmid pBAD18-αRNAP expresses under the control of the arabiose promoter, fusion proteins between the α amino terminal domain (NTD) of the α-subunit of RNA polymerase and DNA fragments cloned into the multiple cloning site. The presence of this plasmid in kanamycin sensitive cells can be selected by plating on growth medium supplemented with kanamycin, or for its absence by the counterselective rpsL allele by plating on media supplemented with streptomycin (Murphy et al. 1995).

The plasmid pBAD30-cI expresses under the control of the arabinose promoter, fusion proteins between the λcI protein and DNA fragments cloned into the multiple cloning site. The presence of this plasmid in amplicillin sensitive cells can be selected by plating on growth medium supplemented with amplicillin, or for its absence by the counterselective lacY gene by plating on media supplemented with 2-nitrophenyl-β-D-thiogalactosidase (tONPG) (Murphy et al. 1995). Additionally, the oriT sequence enables unidirectional genetic exchange of the pBAD30-cI plasmid and its derivatives from E. coli cells containing the F' fertility factor to F⁻ strains lacking the fertility factor.

DETAILED DESCRIPTION OF THE INVENTION

Accordingly, in a first aspect the present invention relates to a method for the identification of at least one member of a pair or complex of interacting molecules from a pool of potentially interacting molecules, comprising:

(A) providing at least one set of host cells, each set containing at least one genetic element comprising a selectable marker, said selectable marker being different between different sets of host cells, said genetic elements each comprising genetic information specifying one of said potentially interacting molecules, said host cells further carrying a readout system that is activated upon the presence of auto-activating molecules;

(B) selecting against host cells expressing a molecule able to auto-activate the readout system by transferring at least one set of host cells or progeny of at least one set of host cells to at least one selective medium which allows growth of said host cells in the presence of said selectable marker different for each set of host cells and which precludes growth of said host cells upon auto-activation of said readout system;

(C) combining in host cells at least two genetic elements, wherein at least one set of host cells grows on said selective medium specified in (B);

(D) allowing at least one interaction, if any, to occur;

(E) selecting for said interaction by transferring said host cells or progeny of said host cells to a selective medium that allows identification of said host cells upon activation of the readout system;

(F) identifying host cells that contain interacting molecules that activate said readout system on said selective medium;

(G) identifying at least one member of said pair or complex of interacting molecules; wherein said host cells are not yeast cells.

Furthermore, in a second aspect the present invention relates to a method for the identification of at least one member of a pair or complex of interacting molecules from a pool of potentially interacting molecules, comprising:

(A) providing at least one set of host cells, each set containing at least one genetic element comprising a selectable marker, said selectable marker being different between different sets of host cells, said genetic elements each comprising genetic information specifying one of said potentially interacting molecules, said host cells further carrying a readout system that is activated upon the presence of auto-activating molecules;

(B) selecting against host cells expressing a molecule able to auto-activate the readout system by transferring at least one set of host cells or progeny of at least one set of host cells to at least one selective medium which allows growth of said host cells in the presence of said selectable marker different for each set of host cells and visual differentiation between those cells whose readout system has been activated from those host cells whose readout system has not been activated;

(C) combining in host cells at least two different genetic elements, wherein at least one set of host cells grows on said selective medium specified in (B);

(D) allowing at least one interaction, if any, to occur, (E) selecting for said interaction by transferring said host cells or progeny of said host cells to a selective medium that allows identification of said host cells upon activation of the readout system;

(F) identifying host cells that contain interacting molecules that activate said readout system on said selective medium;

(G) identifying at least one member of said pair or complex of interacting molecules Furthermore, in a third aspect the invention relates to a method for the identification of at least one member of a pair or complex of interacting molecules from a pool of potentially interacting molecules, comprising:

(A) providing at least one set of host cells, each set containing at least one genetic element comprising a selectable marker, said selectable marker being different between different sets of host cell, said genetic elements each comprising genetic information specifying one of said potentially interacting molecules, said host cells further carrying a readout system that is activated upon the presence of auto-activating molecules;

(B) selecting against host cells expressing a molecule able to auto-activate the readout system by transferring at least one set of host cells or progeny of at least one set of host cells to at least one selective medium which allows growth of said host cells in the presence of said selectable marker different for each set of host cells and which precludes growth of said host cells upon auto-activation of said readout system;

(C) combining in host cells at least two genetic elements, wherein at least one set of host cells grows on said selective medium specified in (B);

(D) allowing at least one interaction, if any, to occur;

(E) selecting for said interaction by transferring said host cells or progeny of said host cells to a selective medium that allows identification of said host cells upon activation of the readout system;

(F) identifying host cells that contain interacting molecules that activate said readout system on said selective medium;

(G) identifying at least one member of said pair or complex of interacting molecules;

wherein said host cells are yeast cells, and at least one of the steps (B), (C), (E) or (F) is effected or assisted by automation using regular grid patterns of host cells.

Another aspect of the invention provides a method for detecting formation of complexes including a first test member and a second test member, comprising:

(a) providing host cells containing at least two genetic elements each with different selectable and counter-selectable markers, said genetic elements each comprising a nucleotide sequence specifying one of said test members, said host cells further including a readout system for producing a detectable signal that is activated upon the interaction of said test members;

(b) culturing the host cells under conditions wherein complexes including said first and second test members, if any, will be formed in the cell;

(c) selecting for said complexes by transferring samples of said host cells to:
(i) at least two different selective media, wherein each of said selective media allows growth of said host cells only in the absence of at least one of said counter-selectable markers and in the presence of a selectable marker, and
(ii) a further selective medium that allows identification of said host cells only on the activation of said readout system; and (d) identifying host cells containing said members that:
(i) do not activate said readout system on any of said selective media specified in step (c)(i); but which
(ii) activate the readout system on said selective medium specified in step (c)(ii).

In certain embodiments, the nucleotide sequence for at least one of the first and second members is variegated in the host cell population to provide a library of different nucleotide sequences for said member(s). For instance, the variegated nucleotide sequences can be from a eukaryotic cDNA library, a eukaryotic genomic library, a prokaryotic genomic library, a prokaryotic cDNA library, or a random or semi-random nucleic acid library.

In certain embodiments of the subject assays, the host cell population has at least $10^6$ different combinations of nucleotide sequences for said first and second member, more preferably at least $10^7$ different combinations, and even more preferably at least $10^8$ different combinations.

In certain embodiments, the false positive rate of the subject method is less than 1 per $10^5$ cells, more preferably 1 per $10^6$ cells, and even more preferably 1 per $\mathbf{10^7}$ cells.

In certain embodiments, the readout system is a reporter gene encoding a gene product that gives rise to a detectable signal selected from the group consisting of: color, fluorescence, luminescence, a cell surface tag, cell viability, relief of a cell nutritional requirement, cell growth, and drug resistance.

It shall be understood herein, that where referral is taken to the "method of the invention" or the "invention", respectively, this shall refer to all three aspects of the invention as described above, whereas when referral is taken to a specific aspect of the invention, namely the first second and third aspect, this shall refer to only this aspect of the invention.

As used herein, "recombinant cells" include any cells that have been modified by the introduction of heterologous DNA.

As used herein, the terms "heterologous DNA" or "heterologous nucleic acid" is meant to include DNA that does not occur naturally as part of the genome in which it is present, or DNA which is found in a location or locations in the genome that differs from that in which it occurs in nature, or occurs extra-chromasomally, e.g., as part of a plasmid.

By "protein" or "polypeptide" is meant a sequence of amino acids of any length, constituting all or a part of a naturally-occurring polypeptide or peptide, or constituting a non-naturally-occurring polypeptide or peptide (e.g., a randomly generated peptide sequence or one of an intentionally designed collection of peptide sequences).

The terms "chimeric", "fusion" and "composite" are used to denote a protein, peptide domain or nucleotide sequence or molecule containing at least two component portions which are mutually heterologous in the sense that they are not, otherwise, found directly (covalently) linked in nature.

More specifically, the component portions are not found in the same continuous polypeptide or gene in nature, at least not in the same order or orientation or with the same spacing present in the chimeric protein or composite domain. Such materials contain components derived from at least two different proteins or genes or from at least two non-adjacent portions of the same protein or gene. Composite proteins, and DNA sequences which encode them, are recombinant in the sense that they contain at least two constituent portions which are not otherwise found directly linked (covalently) together in nature.

By a "DNA binding domain" or "DBD" is meant a polypeptide sequence which is capable of directing specific polypeptide binding to a particular DNA sequence (i.e., to a DBD recognition element). The term "domain" in this context is not intended to be limited to a single discrete folding domain. Rather, consideration of a polypeptide as a DBD for use in the bait fusion protein can be made simply by the observation that the polypeptide has a specific DNA binding activity. DNA binding domains, like activation tags, can be derived from proteins ranging from naturally occurring proteins to completely artificial sequences.

The term "activation tag" refers to a polypeptide sequence capable of affecting transcriptional activation, for example assembling or recruiting an active polymerase complex.

A "reporter gene" includes any gene that expresses a detectable gene product, which may be RNA or protein. Reporter genes include coding sequences for which the transcriptional and/or translational product are readily detectable or selectable.

By "operably linked" is meant that a gene and transcriptional regulatory sequence(s) are connected in such a way as to permit expression of the gene in a manner dependent upon factors interacting with the regulatory sequence(s). In the case of the reporter gene, a DNA binding domain (DBD) recognition element may also be operably linked to the reporter gene such that transcription of the reporter gene will be dependent, at least in part, upon formation of bait-fish complexes, e.g., which may be bound to the recognition element in certain embodiments.

The term "potentially interacting molecule(s)" or "test members", as used in accordance with the present invention, relates to nucleic acids, peptides, domains of proteins or proteins that can be formed upon the transcription and/or translation of genetic information, and which may but are not required to be able to interact with one or more other such nucleic acids, peptides or proteins, together forming a pair or complex of interacting molecules. Preferably, said potentially interacting molecules represent nucleic acids, peptides, domains of proteins or proteins which occur in cells from which the genetic information was derived.

The term "regulatory domain" refers to any domain which regulates transcription, and includes both activation and repression domains. The term "activation domain" denotes a domain in a transcription factor which positively regulates (increases) the rate of gene transcription. The term "repression domain" denotes a domain in a transcription factor which negatively regulates (inhibits or decreases) the rate of gene transcription.

The term "transcriptional activator" as used herein refers to a protein or protein complex which is capable of activating expression of a gene. Thus, as used herein, a transcriptional activator can be a single protein or alternatively it can be composed of several units at least some of which are not covalently linked to each other. A transcriptional activator typically has a modular structure, i.e., comprises various domains, such as a DNA binding domain, and one or more transcriptional activation tags.

The term "interact" as used herein is meant to include detectable interactions between molecules. Interactions may be, for example, protein—protein, protein-nucleic acid, drug-protein, or drug-nucleic acid.

By "covalently bonded" it is meant that two domains are joined by covalent bonds, directly or indirectly. That is, the "covalently bonded" proteins or protein moieties may be immediately contiguous or may be separated by stretches of one or more amino acids within the same fusion protein.

By "altering the expression of the reporter gene" is meant a statistically significant increase or decrease in the expression of the reporter gene to the extent required for detection of a change in the assay being employed. It will be appreciated that the degree of change will vary depending upon the type of reporter gene construct or reporter gene expression assay being employed.

By "test protein" or "test polypeptide" is meant all or a portion of one of a pair of m interacting proteins provided as part of the bait or fish fusion proteins.

By "randomly generated" is meant sequences having no predetermined sequence; this is contrasted with "intentionally designed" sequences which have a DNA or protein sequence or motif determined prior to their synthesis.

Preferably, said potentially interacting molecules specified by said genetic information are connected to a further entity that will upon the interaction activate or contribute to the activation of said read out system. It is further preferred that said entity is conserved for each type of genetic element and that different types of genetic elements comprise different entities. It is additionally preferred that said potentially interacting molecule forms, when transcribed as RNA from said genetic element, an RNA transcript fused with RNA specifying said entity. Most preferably, said fused RNA transcript is translated to form a fusion protein comprising said potentially interacting molecule fused to said entity. As will be elaborated further herein below, said entity may be in one type of genetic element a DNA sequence encoding a DNA-binding domain and in a different type of genetic element a transactivating protein domain. Preferably, said genetic elements are vectors such as plasmids. The at least two genetic elements comprised in said host cell preferentially contain genetic information from a library such as a cDNA or genomic library. Thus, the method of the invention allows the screening of a variety of host cells wherein the vector portion of said genetic elements is preferably the same for each type of genetic element whereas the potentially interacting molecules are representatives of a library and, thus, as a rule and in case that the library has not been amplified, may differ in each host cell or in a majority of host cells. In this connection the term "type of genetic element" refers to an element characterised by comprising the same entity, selectable and, optionally, counterselectable markers. The genetic elements specified in the present invention may further and advantageously be equipped with selection markers functional in bacteria such as $E.$ $coli$. The selection markers, for example aphA (Pansegrau et al., 1987) or bla allow the easy separation of said genetic elements upon retransformation into $E.$ $coli$ strains.

Preferably, the interaction according to the invention is a specific interaction. Preferably, the "interaction" of said molecules is characterised by a high binding constant However, the term "interaction" may also refer to a binding between molecules with a lower binding constant which, however, must be sufficient to activate the readout system. The interaction that is detectable by the method of the invention preferably leads to the formation of a functional entity having a biological, physical or chemical activity which was not present in said host cell before said interaction occurred. More preferably, such activity is a detectable activity. Most preferably, such functional entity is a protein.

Said interaction may preferably lead to the formation of a functional transcriptional activator comprising a DNA-binding and a transactivating protein domain and which is capable of activating a responsive moiety driving the activation of said readout system. For example, said moiety may be a promoter. Alternatively for example, said interaction may lead to a detectable fluorescence resonance energy transfer obtained by the interaction of fusion proteins containing, for example, the GFP type a and GFP type b fluorescent proteins (Cubbitt et al., 1995).

The term "growth on selective media" refers to the fact that yeast cells containing one genetic element are placed on selective media that precludes growth of said cells upon auto-activation of said readout system, or the visual differentiation between cells whose readout system has been auto-activated and those cells whose readout system has not been auto-activated. For example, when a ura3 yeast strain which contains a URA3 reporter system and which also contains a plasmid expressing a LexA fusion protein that activates the URA3 reporter system is selected on selective medium containing 5-fluoroorotic acid (5-FOA), the yeast cells cannot grow on this medium because the URA3 reporter system synthesises the enzyme orotidine-5'-phosphate decarboxylase that converts 5-FOA into the toxic compound 5-fluorouracil (Boeke et al., 1984). In contrast, on a selective medium lacking for example, tryptophan and which contains X-Gal, yeast cells that contain plasmids for the expression of LexA fusion proteins that either activate or do not activate the readout system can grow. However, the yeast cells in which the lacZ reporter system is activated will turn blue because the substrate X-Gal is cleaved into the coloured compound 5-bromo-4-chloro-indigo.

The term "growth on selective medium" also refers to the fact that host cells containing two genetic elements expressing interacting molecules which do not activate the readout system on their own, are selected on selective medium. For example, clones that express interacting LexA and GAL4ad fusion proteins which activate a URA3 and HIS3 reporter system can be selected on selective media lacking tryptophan, leucine histidine and uracil. On this selective medium, only those yeast cells that contain interacting LexA and GAL4ad fusion proteins that activate the URA3 and HIS3 readout system can grow.

When in accordance with the present invention host cells are selected on at least one selective medium precluding growth in the presence of a counterselectable marker, it should be noted that each of the selective media would comprise at least one counterselectable compound such as 5-FOA or cycloheximide wherein the counterselectable compound would be different in different selective media; they would further typically lack a compound complementing for an auxotrophic marker or comprise an antibiotic. The compound or antibiotic may be the same for the various selective media. Preferably, at least one is different.

In accordance with the present invention it is envisaged that a counter selection against clones that express a single molecule able to activate the URA3 readout system can be carried out on culture media preferably comprising 5 fluoroorotic acid (5-FOA). By applying this selection step prior to the preferably automated interaction mating, those clones that express auto-activating fusion proteins can be eliminated from a library of clones.

The terms "auto-activate" or "auto-activation" relate to the fact that certain molecules encoded by said genetic elements are able to activate the readout system without the need for an interacting molecule. For example, the single fusion protein LexA-HIP1 is capable of activating the HIS3 and lacZ readout system without any corresponding interacting activation domain fusion protein (Wanker et al., 1997).

The term "preselection", as used in accordance with the present invention, relates to the selection of a set of host cells comprising a genetic element and a readout system for those host cells expressing a single fusion protein unable to auto-activate said readout system. The term "genetic preselection", as used in accordance with the present invention, relates to preselection emptying counterselection which makes use of a readout system comprising a counterselectable gene.

The present invention provides a highly effective method to perform 2H screens in a variety of host cell types. The invention provides a reliable method for the detection of false positive clones that express fusion proteins which are able to activate the readout system without an interaction with a second molecule. Further aspects provide methods to produce pharmaceutical compositions employing large scale 2H methods. Finally, kits are provided that will allow performing the method of the invention.

In applying 2H techniques to the screening for interacting molecules, it is highly desirable to remove as many False Positives Class 1 and Class 2 as referred to above before allowing an interaction, if any, to occur, in order to reduce the total number of false positives that need to be handled in further steps. In the above aspects of the invention, the present invention provides for three methods to achieve such removal of false positives employing preselection. Inclusion of at least one preselection step as a feature of the invention has a number of significant advantages as compared to prior art methods that we addressed in more detail below.

In accordance with the first aspect of the present invention, said removal of false positives is achieved by counterselection of host cells comprising a counterselectable reporter gene wherein said host cells are not yeast cells.

Although genetic preselection has been shown in yeast 2H systems, so far this concept has not been applied to other cellular systems. While counterselectable reporter genes are readily available for, for example, bacterial systems, and although bacterial 2H systems were available (Dove et al., 1997), the use of genetic preselection in bacterial system has not been described explicitly. This is surprising, as bacterial systems are well suited for certain applications in protein—protein interaction screening as is further expanded on below, and genetic preselection can be advantageously applied in large scale 2H screening. For example, Vidal et al. (1996a), although claiming that the system described is applicable to a wide range of cells, no attempt is made to teach how to overcome the specific challenges the implementation of genetic preselection in bacterial 2H screening would pose.

In the second of the aforementioned aspects of the invention, a preselection step for host cells expressing a single molecule unable to activate the readout system employs visual differentiation between host cells whose readout system has been activated and host cells whose readout system has not been activated. In a preferred embodiment of this aspect of the invention, the readout system comprises at least one detectable protein. More preferably, said detectable protein is encoded from at least one of the genes lacZ, gfp, yfp, bfp, cat, luxAB, HPRT or a surface marker gene. Other such genes exist and the person skilled in the art will readily identify other such genes that can be employed according to this embodiment.

With respect to this second aspect of the invention, it is additionally preferred, that said visual differentiation in step (B) is based on a difference between host cells in different activation states of the readout system which can be detected by visual means. It is particularly preferred that said difference between host cells in different activation states that can be detected by visual means is brought about by activation of one of the genes lacZ, gfp, yfp, bfp, CAT, luxAB, or of a surface marker.

Most preferably, said visual means include digital image capture, storage, processing and/or analysis.

Such visual means may incorporate a camera, a sensitive CCD camera that is suitable for luminescent and fluorescent detection, or may be colourimetric detection systems including computer-based scanners or specialised fluorescent, luminescent or colourimetric plate readers such as the Victor II system from Wallace (Finland).

Preselection employing one or more counterselective reporter genes or, alternatively, by visually detecting host cell expressing a single fusion protein able to activate the readout system, can equally be used to remove false positive clones in the 2H system. Using a counterselective reporter gene, however, is in some cases unsatisfactory for a number of reasons, particularly when applied to a large-scale library vs. library screen with the aim of generating protein interaction networks of a eukaryotic system. First, it is known that during counterselection using media containing counterselective compounds such as 5-FOA, many yeast cells that express the counterselective marker may not be killed, but rather remain dormant and become viable when transferred to a medium free from a counterselective compound. This effect can lead to a 'leaky' genetic preselection system which may lead to a significant number of false-positive colonies being found in an interaction library. This is particularly so when a library vs. library screen is conducted, as even a small number of, e.g. False Positives Class 1, each of which will activate the readout system regardless of its partner protein, will make the task of finding a small number of true positives next to impossible. Second, because many yeast colonies from a library of cells are of different sizes, each containing a different number of cells, collecting surviving cells by scraping or washing off colonies from a counterselective plate will skew the representation of particular inserts from a cloned and plated library. Third, for many host-cell types including mammalian systems, counterselective genes are not available or are difficult to enable. Finally, the sensitivity of a counterselective approach is low since fusion proteins that are weak auto-activators of the readout system will cause insufficient reporter gene transcription to cause cell death through counterselection. In contrast, the readout system commonly used to finally assay any protein—protein interaction between two fusion proteins in the 2H system is the significantly more sensitive β-gal assay. Therefore, many single fusion proteins able to auto-activate the counterselective readout system but not sufficiently to cause cell death would cause a detectable signal from the more sensitive β-gal readout system at a later step.

By preselecting against false positive clones using the same readout system as is used to assay for potential interaction between two fusion proteins at later steps in a 2H screen, the amount of false-positive clones passing through the preselection step can potentially be reduced. Furthermore, by allowing all clones that carry a plasmid to grow and using visual differentiation to distinguish false positive clones, false positive clones could be ignored using an automated colony picking system. This would significantly reduce the problem of false positive clones being carried through the preselective step compared to a counterselective system that is 'leaky' since the location of dormant yet viable cells is unknown. Also, it is well known in the art that readout systems exhibiting visual differentiation between activation and non-activation states, such as β-galactosidase, green fluorescent protein, luciferase, secreted alkaline phosphatase and β-glucuronidase, are detectable when expressed in different host-cell types including yeast, bacteria, plant and insect cells. Therefore, systems to preselect for false positive clones would be easier to transfer to other host-cell types if based on these readout systems.

In the third aspect of the present invention, a method is disclosed subjecting yeast host cells to genetic preselection in a yeast 2H screen, wherein at least one of the steps (A), (C), (E) or (F) is effected or assisted by automation using regular grid patterns of host cells. The cumbersome and highly repetitive nature of the experimental steps involved in large scale 2H experiments makes automation of these steps seem an obvious choice. However, although several authors have previously indicated introducing automation to 2H techniques, it has so far not been shown how a high throughput, automated 2H screen could be performed. In the field of molecular biology, there are a host of different ways by which automation may be conducted, e.g. by using pipetting robots, plate readers, automated sequencing machines etc., but most of these have been developed with the aim to automate the handling of large numbers of different molecules rather than large numbers of different cells or clones. A person skilled in the art could therefore not conclude how to perform high throughput 2H screening from the simple proposal to include automation. Vidal et al. (1996) as well as Hurd et al. (1997) merely mention the possibility of automating the 2H systems they propose without substantiating how to implement this feat; Nandabalan et al., (1997) purport to have introduced automation to 2H screens, enabling large throughput, yet the system they have devised represents exclusively high throughput identification of nucleic acid sequences encoding interacting proteins after clones have been manually handled until identification of positives. The key to automation herein lies in the use of regular grid patterns together with suitable devices and procedures, which automatically process said regular grid patterns.

In a preferred embodiment of the method of the present invention said pair or complex of interacting molecules is selected from the group consisting of RNA—RNA, RNA-DNA, RNA-protein, DNA—DNA, DNA-protein, protein—protein, protein-peptide, or peptide—peptide interactions.

Accordingly, the method of the invention is applicable in a wide range of biological interactions. For example, the invention will be useful in identifying peptide-protein or peptide—peptide-interactions by employing synthetic peptide libraries (Yang et al., 1995).

Two applications of interest are the application of a large scale 2H system for the detection of protein—protein interactions involved in medically relevant pathways which may be useful as diagnostic or therapeutic targets for the treatment of disease, and a large scale tri-hybrid system which is one example of said complex of interacting molecules mentioned herein above for the identification of, for example, novel post-transciptional regulators and their binding sites (SenGupta et al., 1996; Putz et al., 1996). In this regard it should be noted that a complex, in accordance with the invention may comprise more than three interacting molecules. Furthermore, such a complex may be composed of biologically or chemically different members. For example, to identify interacting RNA binding proteins and RNA molecules, a plasmid expressing a LexA-HIV-1Rev protein, a plasmid transcribing an RNA sequence in fusion with the responsive element and a plasmid expressing a potentially RNA-interacting protein in fusion with an activation domain may be present in one cell. The plasmids encoding the RNA fusion molecule and the activation domain fusion protein must contain different selectable and counterselectable markers according to the method of the invention. If the RNA fusion molecule interacts with the respective two fusion proteins, the readout system is activated. To test whether the RNA fusion molecule or the activation domain fusion protein interact, the method of the invention is used to investigate the activation of the readout system in the absence of either of these fusion molecules.

In a further preferred embodiment, said genetic elements are plasmids, artificial chromosomes, viruses or other extra-chromosomal elements.

Whereas it is preferred, due to the easy handling, to employ plasmids that specify the genetic elements in accordance with the present invention, the person skilled in the art will be able to devise other systems that carry said genetic elements. Furthermore, the person skilled in the art will be well aware that the preferred genetic element will depend on the host cell system. For example, retroviral vectors might be employed in mammalian host cells.

In another preferred embodiment, said readout system additionally comprises at least one counterselectable gene.

As the biological principle of counterselection is well known in the art, the person skilled in the art may choose from a variety of such counterselectable genes. Preferably, said genes are URA3, LYS2, sacB, CAN1, CYH2, rpsL, or lacY. The person skilled in the art will be able to choose the appropriate marker for a given cell system, e.g. URA3 in a yeast 2H system or sacB in a bacterial system.

Preferably, said selective medium in step (B) of the method of the invention comprises a counterselective compound. More preferably, said counterselective compound is chosen from 5-FOA, canavanine, cycloheximide, sucrose, streptomycin or.tONPG.

In this embodiment, for example, the URA3 gene is incorporated as a component of the readout system. Clones containing only one of said genetic elements are placed on a selective medium comprising 5-FOA. In the case that clones that express a single molecule able to activate the readout system, 5-FOA is converted into the toxic 5-fluorouracil. Accordingly, host cells containing auto-activating molecules will die on the selective medium containing 5-FOA (Le Douarin, 1995, Vidal et al., 1996a). Surviving cells are then collected by scraping or washing off colonies from the surface.

In an additional preferred embodiment, the readout system according to the invention comprises at least one detectable protein. A number of readout systems are known in the art and may, if necessary, be adapted to be useful in the method of the invention.

Most preferably, said detectable protein is that encoded by the genes lacZ, HIS3, URA3, LYS2, sacB, tetA, gfp, yfp, bfp, CAT, luxAB, HPRT or a surface marker, respectively. As is well known in the art, the expression of the 13-gal enzyme in yeast can be used for the formation of a detectable blue colony after incubation in X-Gal solution. Proteins which confer resistance to an antibiotic represent a popular choice for bacterial cell systems and can be detected by selection for growth in the presence of the antibiotic. Expression of fluorescent proteins, as well as the expression of a surface marker and subsequent visualisation with a fluorescently marked antibody, can preferentially be employed in mammalian systems in conjunction with fluorescence assisted cell sorting (FACS) or laser scanning confocal microscopy. Of course, the method of the invention is not restricted for use of only one readout system. On the contrary, if desired, a number of such readout systems may be combined. Said combination of a number of readout systems is, in accordance with the present invention, also comprised by the term "readout system". Such a combination will provide an additional safe guard for the identification of clones containing interacting partners.

Although the 2H system has been developed in yeast, the method of the invention can be carried out in a variety of host systems. Preferred of those are yeast cells, bacterial cells, mammalian cells (Wu et al. 1996), insect cells, plant cells or hybrid cells. Preferably, the bacterial cells are $E.$ $coli$ cells.

It is understood in the art that to identify, detect or assay the variety of different protein—protein interactions that exist in biological systems, it is likely that a variety of host systems will have to be employed. For example, prokaryotic systems have certain advantages over eukaryotic systems including the ease of genetic, laboratory and automated procedures. Additionally, unlike conventional yeast two-hybrid systems, nuclear localisation of fusion proteins is irrelevant for prokaryotic cells and the entry of small molecules into the cell is typically easier than for a yeast cell. However, some protein—protein interactions depend on post-translational modifications such as mRNA splicing or glycosylation that are not available in prokaryotic or yeast cells, respectively. Therefore, in order to uncover many, if not most, protein—protein interactions that exist in biological systems, library vs. library interactions screens will need to be conducted in a variety of host types. The art would benefit from an improved two-hybrid system that can deal with the large numbers of clones and false-positive clones generated while conducting these screens in a variety of host-types. It would be of great advantage if such a system were available that functioned or was conducted in a substantially similar manner regardless of the host-cell type used. Although other methods to conduct large-scale two-hybrid screens claim to be applicable to all types of cells, they are typically geared towards only one cell type, in most cases yeast. For example, Vidal et al (1996a) describes a genetic method to preselect against cells expressing single fusion proteins able to activate the readout system, but no solution is provided as to how a person skilled in the art may conduct this preselection in for example a prokaryotic or mammalian two-hybrid system. Using detectable proteins such as GFP or β-galactosidase that are appropriate for a broad range of host-types as one part of the readout system, a substantially similar procedure and method can be used to visually differentiate against false positive clones in a variety of host-types.

Of course, the genetic elements may be engineered and prepared in one host organism and then, e.g. by employing shuttle vectors, be transferred to a different host organism where it is employed in the method of the invention.

Whereas the person skilled in the art may initiate the identification method of the invention starting from fully transformed or transfected host cells, he may wish to first generate such host cells in accordance with the aim of his research or commercial interest. For example, he may wish to generate a certain type of library first that he intends to screen against a second library already present in said host cells. Alternatively, he may have in mind to generate two or more different libraries that he wants to screen against each other. In this case, he would need to first transform said host cells, simultaneously or successively, with both or all types of genetic elements.

In another preferred embodiment, the method of the present invention comprises transforming, infecting or transfecting at least one set of host cells of said sets of host cells with said genetic element or genetic elements prior to step (D).

In another preferred embodiment, the method of the invention further comprises transforming, infecting or transfecting each set of host cells of said sets of host cells with dais genetic elements prior to step (D).

In another preferred embodiment, the method of the present invention comprises transforming, infecting or transfecting one set of host cells of said sets of host cells with at least one genetic element prior to step (A), selecting against host cells in said one set of host cells expressing a molecule able to auto-activate said readout system as specified in step (B), and transforming, infecting or transfecting said set of host cells with at least one further genetic element prior to step (D).

In another preferred embodiment, said host cells with said genetic elements are generated by cell fusion, conjugation or interaction mating prior to step (D), preferable in step (C).

In a particularly preferred embodiment, said cell fusion, conjugation or interaction mating is affected or assisted by automation. More preferably, said automation is effected by an automated picking, spotting, rearraying, pipetting, micropipetting or cell sorting device. Most preferably, said device is a picking robot, spotting robot, rearraying robot, pipetting system, micropipetting system or fluorescence assisted cell sorting (FACS) system.

Interaction mating is well known as a tool for use in the yeast 2H system to combine genetic elements that express potentially interacting fusion proteins (Bendixen et al., 1994). Although cell fusion, conjugation or interaction mating are efficient in combining genetic material between different cell strains, such an approach would only be of use in a large-scale library vs. library screen if it could be conducted at high-throughput, due to the large number of colonies that needs to be harvested. By utilising automated systems which had been designed to speed the handling of E. coli cells for the analysis of DNA (Lehrach et al., 1997), it is possible to conduct automated and high-throughput interaction mating in bacteria and yeast cells. Pipetting or micropipetting systems could be used for example in the handling of mammalian cells. Alternatively, FACS could be employed to the same task.

Although picking of E. coli clones for DNA analysis using vision-controlled robotic systems such as described in Lehrach et al. (1997) is well known, the large-scale robotic picking of yeast clones was not considered by the skilled person because of the difficulties of dealing with this organism. For example, yeast colonies typically have variable size, shape and colour when growing on solid agar and often grow on an opaque lawn of non-transformants obstructing visual colony recognition. Secondly, a large-amount of cell material is needed to successfully inoculate further cultures compared to E. coli, and finally, ethanol alone cannot be reliably used to sterilise picking tools between picking cycles.

However, for the reliable picking of clones from, for example, a yeast 2H screen, suitable changes to a standard picking robot as described by Lehrach et al. (1997) had to be devised.

First, the illumination of the agar-trays containing plated colonies was changed from the dark-field sub-illumination typically used when picking E. coli clones to dark-field top-illumination to successfully visualise yeast colonies by differentiation from the lawn of non-transformant cells. The existing vision guided motion system (Krishnaswamy & Agapakis 1997) was modified to allow for a larger range of 'blob' size when selecting yeast colonies to pick from the blobs features returned by connectivity algorithms when applied to a digital image of the agar tray containing colonies. Secondly, the clone inoculation routine was re-programmed to ensure that cell material which had dried on the picking pins during the picking routine was initially re-hydrated by 10 seconds of immersion in the wells of a microtiter plate before vigorous pin-motion with the well. This robotic procedure ensured that sufficient cell material was inoculated from each picking pin into an individual well of a microtiter plate. Finally, the picking pins were sterilised after inoculation to allow the picking cycle to be repeated by programming the robot to brush the picking pins in a 0.3% (v/v) solution of hydrogen peroxide, followed by a 70% ethanol rinse from a second wash-bath and finally a heat-gun treatment to evaporate any remaining ethanol from the pins.

The combination at high-throughput of genetic material from all combinations of pairs of cells expressing fusion proteins could also be conducted in a systematic, rather than a random manner. To minimise the number of false positive entering such an automated combination strategy to identify interacting molecules, it would be preferable to conduct the combination with libraries of cells from which false positive cells had been removed or minimised by genetic preselection or visual differentiation as referred to above.

It will be clear to a person skilled in the art that the approach described here will be able to create regular grid patterns of densities greater than 2 to 10, 10 to 100, 100 to 500 or 500 to 1000 clones per square centimetre, depending on the automated system and host cell type used. By way of illustration, these may be created by using a robotic pipetting or piezo dispensing system carrying one clone to a specific location containing another clone, or by using said approaches to contact cells of one mating type to a lawn of at least one clone of another mating type. Said lawn may be applied as a layer of cells suspended in a solid or semi-solid growth medium or may be applied by spraying a thin and uniform layer of cells of one mating type onto the surface where contact with the cell of the alternative mating type is made. Of particular advantage are systems where individual clones can be individually positioned or contacted with other particular clones. This can be enabled for example by individually addressable multi-head dispensing units, or by a transfer head with individually addressable and moveable transfer pins. Such a system can easily be brought forward by a person skilled in the art using the disclosures in this invention using systems such as the rearraying robots as described by Stanton et al (1995) and Lehrach et al (1997), or from those supplied by commercial robot suppliers such as Genetix (UK). It should be recognised that said combination strategy may be conducted on a planar carrier as disclosed herein below. It may also be conducted directly on solid growth agar, or within the wells of microtiter plates.

It may be that for some library vs. library interaction screens, the number of positive clones obtained by making all possible combinations of interaction mating is low. For a systematic clone vs. clone interaction screen of two libraries each of 10,000 fusion proteins, a minimum of $5 \times 10^7$ combinations need to be tested. If it is assumed that any given fusion protein will have approximately 10 possible interaction partners, only around $10^4$ positive clones and hence protein—protein interactions will be detected from such a screen. Because the efficiency of interaction mating is so high (Sherman et al, 1984), in these cases it would be possible to conduct such large-scale interaction screens more efficiently by contacting individual cells from the different libraries using pools of different clones. Clones from a given library would be pooled in numbers of 2 to 10, 10 to 100, 100 to 500 or 500 to 1000, and pools contacted with clones or pools from a second library. Preferable, said pools of clones shall be designed using multidimensional pooling strategies as are commonly known in the art (Barillot et al, 1991; Strauss, et al, 1992; Liu et al. 1995) such that the individual identity of the two clones that contacted and caused activation of the readout system can be subsequently deconvoluted. It is of advantage that most or all false positive clones are removed from the two libraries prior to combination such that said deconvolution can be conducted most efficiently.

It is further preferred in accordance with the present invention that the selectable markers are auxotrophic or antibiotic markers.

It is important to note that some of the markers that are used as a readout system, may also be used as selectable markers. It is further important to note that one and the same marker can not be used as selectable marker and as part of the readout system at the same time.

Most preferably, said auxotrophic or antibiotic markers are selected from LEU2, TRP1, URA3, ADE2, HIS3, LYS2, kan, bla, Zeocin, neomycin, hygromycin, pyromycin or G418.

Planning of experiments may require that the test for interaction need not be done immediately after the provision of host cells and, possibly, the occurrence of the interactions. In such cases, it may be desirable to store the transformed host cells for further use. Accordingly, a further preferred embodiment of the invention relates to a method wherein progeny of host cells obtained in step (C) are transferred to a storage compartment.

In particular in cases where a large number of clones is to be analysed, said transfer to a storage compartment is advantageously effected or assisted by automation. More preferably, said automation is effected by an automated arraying, picking, spotting, pipetting, micropipetting or cell sorting device. Most preferably, said device is an arraying robot, picking robot, spotting robot, automated pipetting or micropipetting system or FACS system. For example, a pipetting, micropipetting or FACS system may be advantageously applied to the transfer of mammalian cells. Other automation or robot systems that reliably transfer progeny of said host cells into predetermined arrays in the storage compartments may also be employed. As the person skilled in the art will realise, the choice of said device will largely depend on the host cell system under investigation.

The host cells may, in this embodiment, be propagated in said storage compartment and provide further progeny for the additional tests. Preferably, replicas of said storage compartment maintaining the array of clones are set up. Said storage compartments comprising the transformed host cells and the appropriate media may be maintained in accordance with conventional cultivation protocols. Alternatively, said storage compartments may comprise an anti-freeze agent and therefore be appropriate for storage in a deep-freezer. This embodiment is particularly useful when the evaluation of potential interacting partners is to be postponed. As is well known in the art, frozen host cells may easily be recovered upon thawing and further tested in accordance with the invention. Most preferably, said anti-freeze agent is glycerol which is preferably present in said media in an amount of 3–25% (vol/vol), or DMSO.

In a further particularly preferred embodiment of the method of the invention, said storage compartment is at least one microtiter plate. Most preferably, said at least one microtiter plate comprises 96, 384, 846 or 1536 wells. Microtiter plates have the particular advantage of providing a pre-fixed array that allows the easy replicating of clones and furthermore the unambiguous identification and assignment of clones throughout the various steps of the experiment. 384, 846 or 1536 well microtiter plates are, due to comparatively small size and large number of compartments, particularly suitable for experiments where large numbers of clones need to be screened, but plates with lower numbers of cells may be required depending on the host cell system.

Depending on the design of the experiment, the host cells may be grown in the storage compartment such as the above microtiter plate to logarithmic or stationary phase. Growth conditions may be established by the person skilled in the art according to conventional procedures. Cell growth is usually performed between 15 and 45 degrees Celsius.

Referring to step (E), in a preferred embodiment of the method of the invention, the transfer of said host cells or progeny of host cells is effected or assisted by automation using a regular grid pattern. More preferably, said automation using a regular grid pattern transfer of said host cells or progeny of host cells is effected by an automated picking, spotting, replicating, pipetting or micropipetting device. Most preferably that device is a picking robot, replicating robot, spotting robot, pipetting system, micropipetting system or fluorescent assisted cell sorting (FACS) system. How such a robot or automated system may be devised and equipped is, for example, described in Lehrach et al. (1997). Other automation or robot systems that reliably transfer progeny of said host cells into predetermined arrays in the storage compartments may also be employed. By using a computer-controlled pipetting system according to the invention, regular grid patterns of high density could be created. According to this embodiment of the invention, planar carriers with a high-density pattern of yeast clones from the defined interaction library contained within 384-well microtiter plates are provided by using a high-throughput spotting robot such as that described by Lehrach et al. (1997). Further, a regular grid pattern of yeast cells expressing fusion proteins at a density greater than 18 clones per square centimetre within 1536-well microtiter plates, which have a well every 2.25 mm in a 32 by 48 well arrangement, a regular grid, is provided. As the person skilled in the art will realise, the choice of said device will largely depend on the host cell system under investigation.

In order to increase the population of host cells available for growth on said selective medium in step (E), it is most advantageous to make multiple transfers that carry additional host cells of the same clone to the same position in said regular grid. Preferably, the number of said multiple transfers is between 2 and 20 times. If said multiple transfer is from a microtiter plate and effected or assisted by automation it is most advantageous to be made from a slightly different position of the microtiter plate well containing said clone.

In a preferred embodiment of the invention, said transfer is made to at least one carrier.

In another preferred embodiment, this at least one carrier is a microtiter plate, and the regular grid pattern is at densities greater than 1, preferably greater than 4, more preferably greater than 10, most preferably greater than 18 clones per centimeter square.

In yet another preferred embodiment, said at least one carrier is a porous support and the the regular grid pattern is at densities in the range of 1 to 10, preferably 10 to 50, more preferably 50 to 100, most preferably greater than 100 clones per centimeter square.

In yet another preferred embodiment, said at least one carrier is a non-porous support and the regular grid pattern is at densities in the range of 1 to 100, preferably 100 to 500, more preferably 500 to 1000, most preferably greater than 1000 clones per centimeter square.

The progeny of said host cells may be transferred to a variety of carriers. It is well known in the art that many enzymatic screens can be conducted at high throughput in microtiter plates. Microtiter plates are robotically handled, filled, incubated and any signal from the enzymatic screen measured. Indeed, this approach forms the basis of most high-throughout screen in the pharmaceutical industry to identify primary hits from large chemical libraries. Each well in such a screen contains identical cells or other biological system, and it is only the small amount of test chemical that differs in each well of the microtiter plate. In contrast, a library of host-cells expressing fusion proteins effectively comprises a different biological system in every well (host-cell expressing two potentially interacting fusion proteins) that must be screened for activity of the readout system. If a screen to identify interacting positive cells that express interacting molecules could be conducted using microtiter plates, then it would be possible to use substantially similar robotic systems to that currently developed for high-throughput enzymatic screens.

A person skilled in the art will recognise, that although the Yeast One Step Yeast Lysis Buffer supplied by Tropix (USA) is a convenient method to lyse cells for a microtiter plate format screen, other methods are appropriate. Other methods to lyse host cells are well known in the art and include lysis of cells stored in a microtiter plate without anti-freeze medium by a freeze-thaw procedure, or by addition of a small amount of toluene/chloroform mixture. Other β-galactosidase substrates equally may be used including X-Gal, and the activity of the reporter gene measured by colourimetric means from the density of the blue-colour produced. Indeed, other readout systems may be utilised that do not depend on cell lysis. For example, secreted enzymes such as secreted alkaline phosphatase, or cell-surface or secreted proteins that may be detected by ELISA assay. Readout systems that do not depend on additional substrates, for example green fluorescent protein, may also be utilised. The method of detection used will depend on the readout system used, and may include a sensitive CCD camera that is suitable for luminescent and fluorescent detection, or may be colourimetric detection systems including computer-based scanners or specialised fluorescent, luminescent or colourimetric plate readers such as the Victor II system from Wallace (Finland). A person skilled in the art would also be able to design a readout system based on radioactive detection using for example a scintillation counter or phosphor storage imaging (Johnston et al., 1990).

This carrier might also be a porous support e.g. a membrane manufactured from nylon, nitro-cellulose, cellulose acetate or PVDF, which membrane would be particularly advantageous for bacterial cells or yeast cells. Said solid support could, for example be a glass slide coated with poly-lysine, which glass slide would be particularly advantageous for mammalian cells. Solid supports can be advantageous, as they allow the highest spotting densities. In general, higher spotting densities are advantageous in large scale screening and, hence, preferred. As the person skilled in the art will realise, the choice of said carrier will largely depend on the host cell system under investigation.

The selective media used for growth of appropriate clones may be in liquid or in solid form. Preferably, said selective media when used in conjunction with a spotting robot and membranes as planar carriers are solidified with agar on which said spotted membranes are subsequently placed. Alternatively, and also preferably, said selective media when in liquid form are held within microtiter plates and said transfer is made by replication.

Referring now to step (F) of the method of the invention, in a preferred embodiment the activation state of the readout system can be analysed by a variety of means. For example, it can be analysed by visual inspection, radioactive, chemiluminescent, fluorescent, photometric, spectrometric, infrared, colourimetric or resonant detection.

More preferably, said identification in step (F) of host cells that express interacting fusion proteins from consideration of the activation state of said readout system of host cells grown on the selective medium as specified in step (F) is effected or assisted by using visual means.

Most preferably, said identification of host cells that express interacting fusion proteins in step (F) from consideration of the activation state of said readout system is effected or assisted by automated digital image capture, storage, analysis or processing. Here, automation stands for the use of electronic devices such as computers in conjunction with complex instruction sets such as software, commercially available or self devised, which performs or assists in performing large numbers of calculations on images converted to a digital format. In this embodiment, positive clones which are preferably arrayed on a planar carrier such as a membrane are identified by comparison of digital images obtained from the carrier after activation of said readout system on said selective media specified in (E).

The analysis of a small number of clones or grids for activity of the readout system can be conducted by manual inspection of the activation state for each individual clone. However, when dealing with the number of clones generated by library vs. library interactions screens, or when analysing regular grid patterns produced at densities presented here, such manual inspection becomes time consuming to the extent of almost being impossible.

According to the invention it is possible to efficiently analyse regular grid patterns of 2H clones using visual means. Thus, when members comprising an interaction are identified, a digital image of the planar carrier is obtained and analysis is effected by digital image capture, storage, processing or analysis using an automated or semi-automated image analysis system, such as described in Lehrach et al. (1997). There are many forms and combinations of steps in handling digital image data that the person skilled in the art would know to apply to this task laid out in the present invention.

Referring to step (G) of the present invention, identification of the at least one member of the pair or complex of interacting molecules may be effected by a variety of means. In a preferred embodiment of the present invention, at least one member of said pair or complex of interacting molecules is characterised by nucleic acid hybridisation, oligonucleotide hybridisation, nucleic acid or protein sequencing, restriction digestion, spectrometry or antibody reactions, determining the genetic information encoding said at least one member. Once the first member of an interaction has been characterised, the second member or further members can also be characterised by any of the above methods. Preferably the identification of at least one member of an interaction is effected by nucleic acid hybridisation, antibody binding or nucleic acid sequencing.

More preferably, said identification of at least one member of said pair or complex interacting molecules is effected using regular grid patterns of said at least one interacting molecules or of said genetic information encoding said at least one member or of said genetic information encoding said at least one member. Yet more preferably, construction of said regular grid patterns in step (G) is effected or assisted by automation. Yet more preferably, said automation in step (G) is effected by an automated spotting, pipetting or micropipetting device. Yet more preferably, said automation in step (G) is implemented by employing a spotting robot, spotting tool, pipetting system or micropipetting system. Yet more preferably, said identification is effected by automated digital image capture, storage, processing and/or analysis. Yet more preferably, said nucleic acid molecules, prior to said identification in step (G), are amplified by PCR or are amplified in a different host cell as a part of said genetic elements, more preferably in bacteria and most preferably in E. coli.

If nucleic acid hybridisation is to be carried out, the nucleic acid molecules comprised in the host cell and encoding for at least one of the interacting molecules is preferably affixed to a planar carrier. As is well known in the art, said planar carrier to which said nucleic acid may be affixed, can be for example a Nylon-, nitrocellulose- or PVDF membrane, glass or silica substrate (DeRisi et al. 1996; Lockhart et al. 1996). Said host cells containing said nucleic acid may be transferred to said planar carrier and subsequently lysed on the carrier and the nucleic acid released through said lysis is affixed to the same position by appropriate treatment. Alternatively, progeny of the host cells may be lysed in a storage compartment and the crude or purified nucleic acid obtained is then transferred and subsequently affixed to said planar carrier. Advantageously, said nucleic acids are amplified by PCR prior to transfer to the planar carrier. Most preferably said nucleic acid is affixed in a regular grid pattern in parallel with additional nucleic acids representing different genetic elements encoding interacting molecules. As is well known in the art, such regular grid patterns may be at densities of between 1 and 50 000 elements per square centimeter and can be made by a variety of methods. Preferably, said regular patterns are constructed using automation or a spotting robot such as described in Lehrach et al. (1997) and Maier et al. (1997) and furnished with defined spotting patterns, barcode reading and data recording abilities. Thus it is possible to correctly and unambiguously return to stored host cells containing said nucleic acid from a given spotted position on the planar carrier. Also preferably, said regular grid patterns may be made by pipetting systems, or by microarraying technologies as described by Shalon et al. (1996), Schober et al (1993) or Lockhart et al. (1996). Identification is, again, advantageously effected by nucleic acid hybridisation.

Once produced, nucleic acids carried on these arrays can be detected using a variety of methods. Preferably, this method is hybridisation using labelled hybridisation probes. However, other detection methods such as mass-spectrometry may be employed. Said labelled hybridisation probes can be labelled with any detectable moiety including radioactive elements, fluorescent and chemiluminescent molecules, or molecules that can be detected via secondary enzymatic or binding assays. Said hybridisation probe can comprise DNA, RNA or PNA molecules, and may consist of a single class of molecule, for example a short oligonucleotide, gene fragment, cDNA clone, genomic fragment or YAC. Also, said hybridisation probe may be a complex mixture of nucleic acids representing the gene-expression state of a given tissue, cell type, or developmental or disease state. Two said complex mixtures of nucleic acids may be used in two separate hybridisation experiments with replica nucleic acid arrays to identify those interactions that are specific or more commonly found in the expression state of a given tissue compared to a reference tissue. The methods of producing said complex mixtures and their application as hybridisation probes to nucleic acid arrays are well known in the art (for example, Gress et al., 1996, Lockhart et al., 1996; De Risi et al., 1996). This approach may be applicable to identify disease specific protein—protein interactions that may be targeted by therapeutic agents directed at said disease-specific protein—protein interaction.

Using a detectable nucleic acid probe of interest, homologous nucleic acids which are affixed on the planar carrier can be identified by hybridisation. From the spotted position of said homologous identified nucleic acid on the planar carrier, the corresponding host cell in the storage compartment can be identified which contains both or all members of the interaction. The for example second member of the interaction can now be identified by any of the above methods. For example, by use of a radioactively labeled Ras probe, homologous nucleic acids on the planar carrier can be identified by hybridisation. The Ras interacting proteins can now be identified from the corresponding host cell that contains both the first genetic element homologous to the Ras probe and the second genetic element encoding for these Ras interacting proteins.

If multiple oligonucleotide hybridisations are carried out on the nucleic acids affixed to the planar carrier, oligo fingerprints of all genetic elements encoding the interacting proteins can be obtained. These oligo fingerprints can be used to identify all members of the interactions or those members that belong to specific gene families, as described in Maier et al. (1997).

If nucleic acid sequencing is used, the nucleic acid molecules that encode the interacting proteins are, prior to the identification in step (G), amplified by PCR or in said genetic elements in host cells and preferably in E. coli. Amplification of said genetic elements is conducted by multiplication of the E. coli cells and isolation of said genetic elements. Methods of identifying the nucleic acids that encode interacting proteins by DNA sequencing and analysis are well known in the art. By amplifying and sequencing the nucleic acids that encode for both or all members of an interaction from the same clone, the identity of both or all members of the interaction can be determined.

If a specific antibody is to be used to determine whether a protein of interest is expressed as a fusion protein within an interaction library, it is advantageous to affix all fusion proteins expressed from the interaction library onto a planar carrier. For example, clones of the interaction library that express fusion proteins can be transferred to a planar carrier using a spotting robot as described in Lehrach et al (1997). The clones are subsequently lysed on the carrier and released proteins are affixed onto the same position. Using, for example, an anti-HIP1-antibody (Wanker et al. 1997), clones from the interaction library that contain HIP1 fusion proteins and an unknown interacting fusion protein can be identified. The unknown member of the interacting pair of molecules can now be characterised from the corresponding host cell by any of the above methods. The antibodies used as probes may be directly detectably labelled. Alternatively, said antibodies may be detected by a secondary probe or antibody which may be specific for the primary antibody. Various alternative embodiments using, for example, tertiary antibodies may be devised by the person skilled in the art on the basis of his common knowledge.

It would be theoretically possible to systematically identify all the members comprising the interactions using the methods described above for all positive clones. However, this would be very laborious, costly, and would cause many identical interactions to be identified repetitively. It is likely that any protein—protein interaction pathways would only be developed stochastically as the relevant interactions were randomly identified during the identification process.

Alternatively, the present invention provides for a method to characterise the positive clones identified in a 2H search in a more focused approach, preferably identifying directly yeast clones that express interactions representing the next step in an interaction network from the knowledge of a first molecule that interacts with a given molecule, and hence reduce the time, amount and cost of identifying the interacting members by, for example, systematic DNA sequencing.

Previously, a focused approach could only be followed within the framework of the standard 2H techniques. For example, starting with a gene of interest, a classic single bait 2H experiment would be conducted to identify clones that activated the readout system. These clones would subsequently be tested to determine if they were positive or false positive clones and the interacting members expressed in the positive clones identified. The gene expressing a protein identified as interacting with the initial bait of interest, would then be sub-cloned and subjected to a second yeast-two hybrid experiment to identify which further proteins it interacted with. A separate 2H experiment would have to be conducted for each separate protein—protein interaction step in the pathway. Each step in such a sequential yeast 2H approach would take over two weeks, and thus to generate complete or even partially complete interaction pathways by such an approach would be very time and cost consuming.

A modified hybridisation approach from the ones known in the art (Lennon, Lehrach, 1991; Ross et al., 1992; Shalon et al., 1996; Lehrach et al., 1997) is provided by the present invention. This approach is advantageous when applied to the identification of interacting members within the yeast two hybrid system. By hybridising a probe representing the gene of interest to a regular grid pattern of the nucleic acids including those that express the interacting members, the identification efforts can be focused only on those positive clones which hybridised to the probe of interest. This is because, as well as expressing the gene of interest, such hybridisation-positive and interaction-positive clones would also express a second, interacting protein encoded by one of the 2H vectors. By isolation of the plasmids carried from these hybridisation-positive clones from a stored copy of the interaction library and subjecting them to further characterization procedures, the identification of proteins that interact with the gene of interest, sequential identification procedures can be focused on. For each step in the protein—protein interaction pathway to be investigated, this approach simply requires nucleic acid hybridisation, plasmid isolation, DNA sequencing and a second hybridisation using the isolated insert. Such a combination of standard procedures may be conducted within a matter of days, and several different pathways may be investigated in parallel by the use of replica nucleic acid arrays. Therefore, the time taken to investigate a given protein—protein interaction pathway is considerably shorter than by alternative approaches.

There are a number of further advantages of this hybridisation approach. Firstly, it provides an internal control as the clone from which the probe was isolated should be a hybridisation-positive clone. Secondly, the hybridisation approach may be used not only to identify those clones expressing interacting fusion proteins of interest, but also to ignore those clones that express fusion protein for which the investigator has no interest. For example, it is known that some proteins (for example heat shock proteins) are especially 'sticky', and generate positive clones in the yeast 2H system that may have little biological relevance. Positive clones expressing such 'fortuitous' interactions may be identified and hence ignored from further analysis by a simple hybridisation to an array representing the DNA encoding the fusion proteins expressed within cells of the interaction library. Finally, if both members of a given interaction have been identified, then it may be that the investigator does not wish to waste further resources on re-isolating the same interaction. Identifying those clones from the interaction library that are hybridisation-positive for both members of a previously identified interaction will enable the investigator to ignore these clones for further work. These embodiments have the advantage of saving the investigator both cost and time. By careful selection of the hybridisation probe and focusing only on hybridisation-positive clones, the investigator can successively narrow his search to those clones which carry coding regions, thereby avoiding isolation of large numbers of short peptide fragments caused by translation of 5' or 3' regions of genes.

The focused hybridisation approach to identifying interactions based on hybridisation will rapidly identify many interactions making up a protein—protein interaction pathway. Indeed, by identifying most interactions that make up several different protein—protein interaction pathways, it will be extremely probable that two or more pathways will be found to have a particular protein in common. Such pathways can then be combined and hence form part of a network of protein—protein interactions. Therefore, because this approach can efficiently investigate several different protein—protein pathways in parallel, it is highly suitable to the generation of a network of protein—protein interactions.

In a further preferred embodiment, the present invention provides for a method further comprising:

(H) providing at least one of said genetic elements in step (A), which additionally comprises or comprise a counterselectable marker, wherein said counterselectable markers are different for each type of genetic element;

(I) selecting for interaction by transferring host cells or progeny of host cells, which transfer is optionally effected or assisted by automation in a regular grid pattern, in step (E) to
 (i) at least one selective medium that allows growth of host cells only in the absence of a counterselectable marker specified in (H) and in the presence of a selectable marker, and
 (ii) a further selective medium that allows identification of host cells upon activation of the readout system;

(J) identifying host cells in step (F) that contain interacting molecules that:
 (iii) do not activate said readout system on said at least one selective medium specified in (i), and
 (iv) activate said readout system on said selective medium specified in (ii).

In a more preferred embodiment, said genetic element that additionally comprises a counterselectable marker further specifies an activation domain fusion protein.

As referred to above, false positive clones have proven to dramatically reduce the overall usefulness of the 2H system. For example, by inclusion of a marker counterselecting for the absence of a genetic element that specifies one of a pair of the potentially interacting partners, clones that will grow and therefore only carry the second genetic element specifying the second partner can now be tested for the activation of the readout system. If the clone containing only the fusion protein encoded by the second genetic element activates the readout system in the absence of the other genetic element, then it will be classified as a false positive. Thus, only clones that activate the readout system in the presence of both or all genetic elements, but do not activate the read out system when one of the genetic elements is lost are classified as positives. In order to save time and effort, preferably only the plasmid encoding the activation domain is removed, as the fusion protein comprising the DNA binding domain is more likely to have auto-activating properties.

In a further preferred embodiment, the present invention provides for a method further comprising:

(K) providing at least two of said genetic elements in step (A), which additionally comprise different counterselectable markers;

(L) selecting for interaction by transferring host cells or progeny of host cells in step (E) to (v) at least one selective medium, wherein said selective medium precludes growth of host cells in the presence of the first counterselectable marker of the counterselectable markers specified in (K) and allows growth in the presence of a first selectable marker, (vi) at least one selective medium, wherein said selective medium precludes growth of host cells in the presence of the second counterselectable marker of the counterselectable markers specified in (K) and allows growth in the presence of a second selectable marker;

(vii) a further selective medium that allows identification of said host cells upon activation of the readout system; and (M) identifying host cells that contain molecules that:

(viii) do not activate said readout system on said at least one selective medium specified in (v); and (ix) do not activate said readout system on said at least one selective medium specified in (vi); and (x) activate said readout system on said selective medium specified in (vii).

In a more preferred embodiment, said at least two genetic elements that additionally comprise a counterselectable marker further specify a DNA binding domain fusion protein and an activation domain fusion protein, respectively.

Yet more preferably, said counterselectable marker or counterselectable markers of step (H) or (K) are selected from the group of URA3, LYS2, sacB, CAN1, CYH2, rpsL, or lacY.

Additionally preferred is an embodiment, wherein the transfer of host cells or progeny of host cells in step (I) or (L) is effected or assisted by automation. More preferably, said automation in step (I) or (L) is effected by an automated replicating, picking, spotting, pipetting or micropipetting or cell sorting device. Most preferably, said automation in step (I) or (L) is implemented by employing a replicating robot, picking robot, spotting robot, spotting tool, automated pipetting, micropipetting system, or fluorescent assisted cell sorting (FACS) system.

Herein, the same test is also applied to the first genetic element, counterselecting for the absence of the second genetic element. When employing the present invention according to this embodiment, only clones that activate the readout system in the presence of both or all genetic elements, but do not activate the read out system when either of the genetic elements is lost are classified as positives. By removing both genetic elements, a maximum number of false positives can be identified. This becomes particularly useful with growing total numbers of clones.

The use of the counterselectable system described in this invention compared to the prior art has the advantage that only one strain which expresses the potentially interacting fusion proteins is generated and must be analysed. In contrast, to detect false positive clones using the state of the art yeast 2H system, plasmids that encode fish proteins usually need to be isolated and retransformed into yeast cells harboring plasmids that encode unrelated bait proteins. Further, the enormous number of false positive clones that would be isolated when using the classical 2H system on a large scale, yet are discriminated by the method of this invention no longer precludes an effective high through-put analysis of clones. In the long run, it is expected that the method of the present invention is especially advantageous for a high throughput analysis of a large number of clones containing interacting molecules since many specific interactions and the individual members of these interactions can be identified in a parallel and automated approach.

A significant advantage of the method of invention over existing yeast two-hybrid systems is the scale at which such identification of interactions and interaction members can be made. Preferably, the method of invention screens library vs. library interactions using arrayed interaction libraries. Hence, in one preferred embodiment of the present invention, said genetic information specifying one of said potentially interacting molecules is different for each host cell in a set of host cells or a majority of host cells in a set of host cells.

In a particularly preferred embodiment, said genetic information specifying one of said potentially interacting molecules is identical in not more than 10%, preferably not more than 5%, more preferably not more than 2%, most preferably not more than 1% of host cells in a set of host cells.

The present invention also relates to a method for the production of a pharmaceutical composition comprising formulation of said at least one member of said pair or complex of interacting molecules identified by the method of the invention in a pharmaceutically acceptable form. Said pharmaceutical composition comprises at least one of the aforementioned compounds identified by the method of the invention, either alone or in combination, and optionally a pharmaceutically acceptable carrier or excipient. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by conventional methods. These pharmaceutical compositions can be administered to subject in need thereof at a suitable dose. Administration of the suitable compositions may be effected by different ways, e.g., by intravenous, intraperitoneal, subcutaneous, intramuscular, topical or intradermal administration. The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Dosages will vary but a preferred dosage for intravenous administration of DNA is from approximately 106 to 1022 copies of the nucleic acid molecule. Proteins or peptides may be administered in the range of 0 μl ng to 10 mg per kg of body weight. The compositions of the invention may be administered locally or systematically. Administration will generally be parenterally, e.g., intravenously; DNA may also be administered directly to the target site, e.g., by biolistic delivery to an internal or external target site or by catheter to a site in an artery.

The present invention further relates to a method for the production of a pharmaceutical composition comprising formulating an inhibitor of the interaction of the at least one member of said pair or complex of interacting molecules identified by the method of the invention with another molecule, preferably also identified by the method of the invention, in a pharmaceutically acceptable form. The inhibitor may be identified according to conventional protocols. Additionally, molecules that inhibit existing protein—protein interactions can be isolated with the yeast 2H system using the URA3 readout system. Yeast cells that express interacting GAL4ad and LexA fusion proteins which activate the URA3 readout system are unable to grow on selective medium containing 5-FOA. However, when an additional molecule is present in these cells which disrupts the interaction of the fusion proteins the URA3 readout system is not activated and the yeast cells can grow on selective medium containing 5-FOA. Using this method potential inhibitors of a protein—protein interaction can be isolated from a library comprising these inhibitors. Systems corresponding to the URA3 system may be devised by the person skilled in the art on the basis of the teachings of the present invention and are also comprised thereby.

Also, the present invention relates to a method for the production of a pharmaceutical composition comprising identifying a further molecule in a cascade of interacting molecules, of which the at least one member of interacting molecules identified by any of the above methods is a part of or identifying an inhibitor of said further molecule. Once at least one member of the interacting molecules has been identified, it is reasonable to expect that said member is a part of a biological cascade. Identification of additional members of said cascade can be effected either by applying the method of the present invention or by applying conventional methods. Also, inhibitors of said further members can be identified and can be formulated into pharmaceutical compositions.

Moreover, the invention relates to a kit comprising:
(N) Host cells, comprising a readout system which allows host cells to be counterselected against auto-activation of said readout system; and
(O) at least one genetic element comprising a selectable marker, a counterselectable marker and genetic information encoding an activation domain or a DNA binding domain, which activation domain and DNA binding domain are together able to activate said readout system;
wherein said host cells are not yeast cells.

In a preferred embodiment, said kit comprises bacterial cells.

Such kits could be used to carry out the first aspect of the invention.

Futhermore, the invention relates to a Kit comprising:
(P) Host cells comprising a readout system which allows host cells to be visually differentiated upon activation of said readout system; and
(O) at least one genetic element comprising a selectable marker and genetic information encoding an activation domain or a DNA binding domain, which activation domain and DNA binding domain are together able to activate said readout system;

In a preferred embodiment, said kit comprises bacterial cells or mammalian cells.

Such kits could be used to carry out the second aspect of the invention.

These kits could be used, for example, for the rapid identification of inhibitors of interactions or pathways of interactions, for the identification of pathways that toxic substances act on, or, concomitantly, detoxifying agents and for the identification of interaction pathways.

(R) The invention further relates to a method for the identification of at least one member of a pair or complex of interacting molecules, comprising:
(S) providing at least two sets of host cells each containing at least one genetic element with a selectable marker different for each set of host cells, said genetic elements each comprising genetic information specifying one of said molecules, said host cells further carrying a readout system that is activated upon the presence of autoactivating molecules;
(T) screening or selecting against molecules that auto-activate said readout system by transferring progeny of at least one set of host cells to:
(U) selecting for said interaction by transferring progeny in a regular grid pattern effected by automation to:
(xi) a selective medium which allows growth of said host cells in the presence of said selectable marker different for each set of host cells and which precludes growth of said host cells upon auto-activation of said readout system; or, and/or
(xii) a selective medium which allows growth of all of said host cells and visual differentiation between those cells whose readout system has been auto-activated and those whose readout system has not been auto-activated;
(R) combining in host cells said genetic elements from at least two different sets of host cells, wherein at least one set of host cells grows on said selective medium specified in (xi) or does not auto-activate said readout system on said selective medium specified in (xii);
(S) allowing at least one interaction, if any, to occur;
(T) identifying host cells obtained in step (c) containing interacting molecules that activate said readout system:
(U) identifying at least one member of said pair of interacting molecules.

Preferably, the data obtained by using the method of the present invention can be accessed through the use of software tools or graphical interfaces that enable to easily query the established interaction network with a biological question or to develop the established network by the addition of further data. A computer-based system provides a robust and efficient solution for handling the large amount of protein—protein interaction data produced by the method of the invention.

Figure 2:
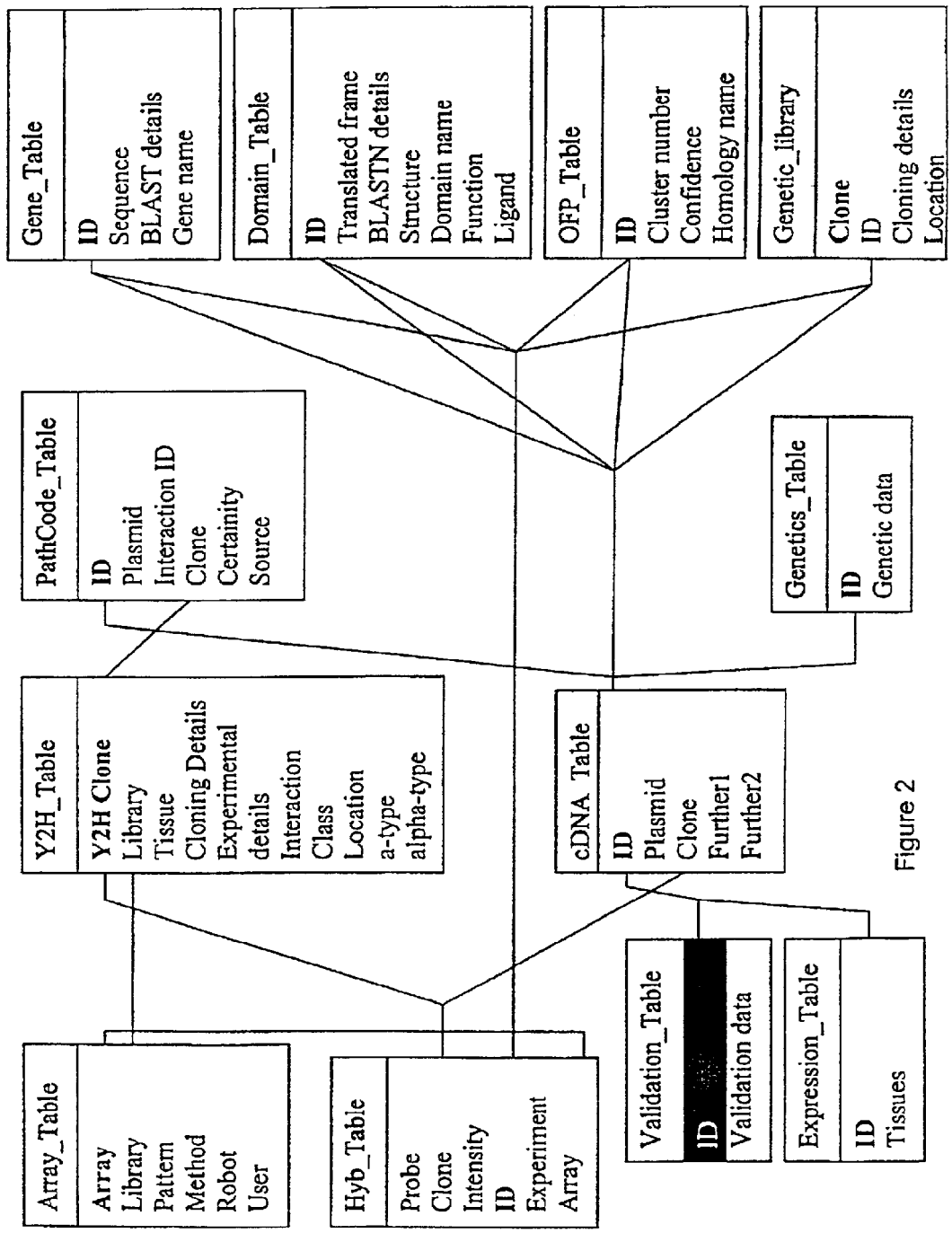
Figure 3:
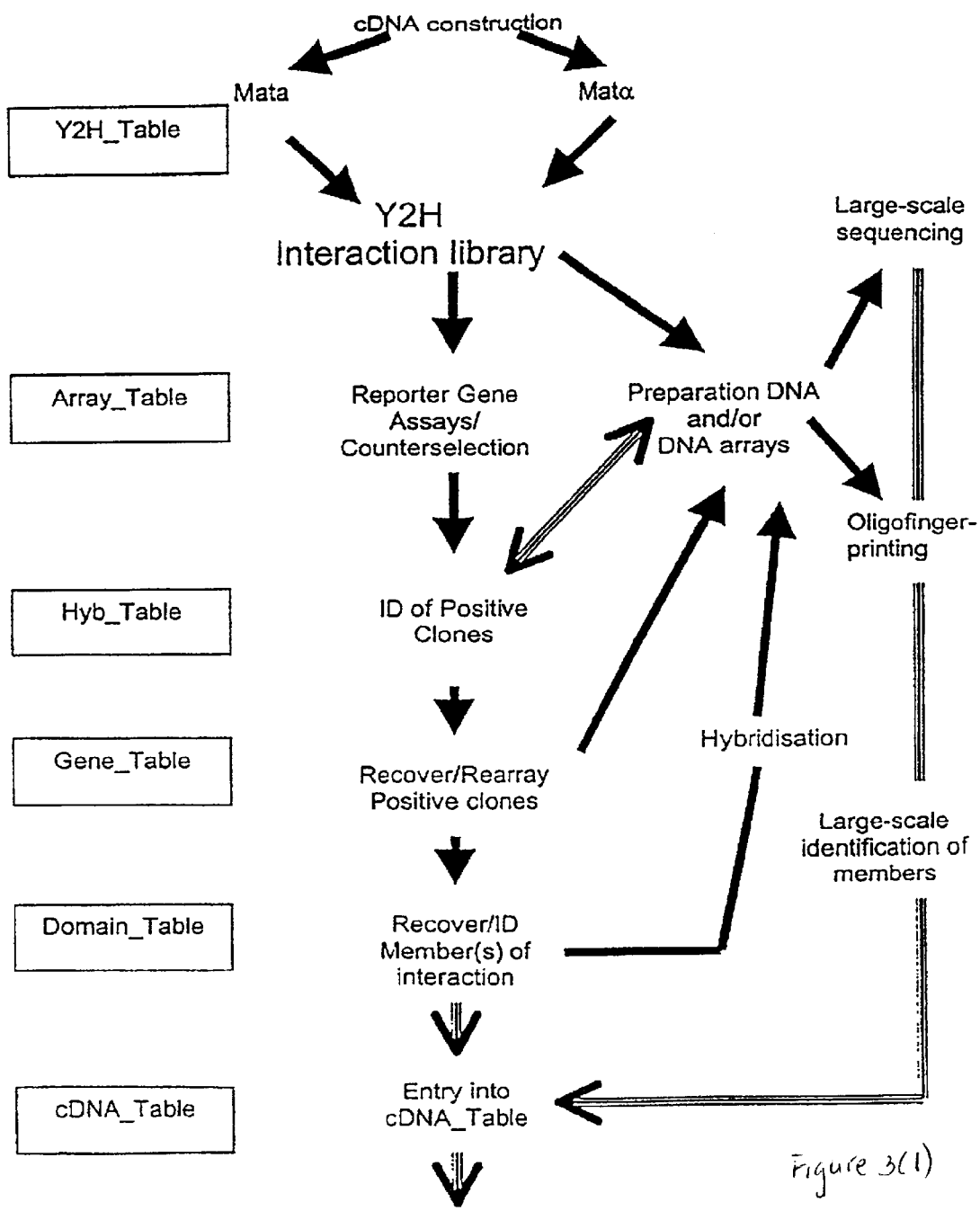
Figure 3:
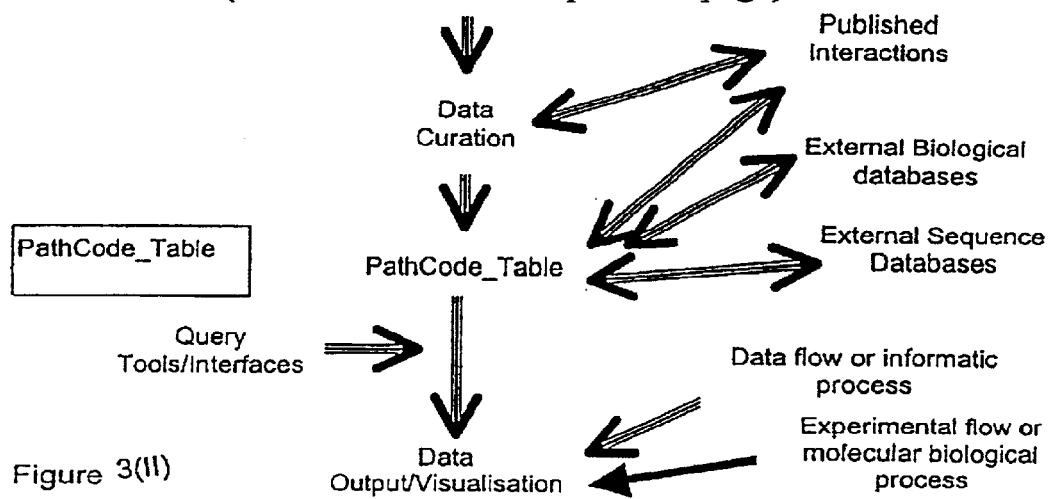

Such a solution would include the features of simple data-entry procedures, efficient use of memory and disk space for storage and data-processing, the ability to communicate and utilise with different data-bases and/or computers across intra or internets, interfaces to allow querying of the data-base by an investigator and visual display of the results of the query. Relational or object orientated data-bases, with data-parsing and display programs supporting said data-base are possible embodiments to implement said solution. As way of example, FIG. 2 displays a scheme and features for a set of data-tables suitable for managing such interaction data that could be implemented in either relational or object-orientated data-bases. The primary links between table-keys are indicated, as are the suggested fields or elements to be held within each table. It would be possible that certain elements of a table may be expanded into an additional table holding further data. Likewise, it would be possible that certain tables may be expanded into an additional data-base to hold and manage further data. Said additional data-base may be held on the same, or remote computers. Elements of the table may be recorded in numerical, descriptive of fixed format as may be appropriate for the data, and to provide efficient querying, it is of advantage that where appropriate, elements are recorded in controlled vocabulary. FIG. 3 displays in what part of the work process during an interaction experiment each table is most relevant and where it forms the underlying data-set from which work-flow management software for that part of the process is based.

Other computer-based methods of generating visual representations of specific interactions, partial or complete protein—protein interaction networks can be employed to automatically calculate and display the required interactions most efficiently. As is well known in the art, computer data-bases are a valuable resource for large-scale biological and molecular biological research.

An established computer data-base of protein interactions has many useful applications. For example, it may be used to predict the existence of new biological interactions or pathways, or to determine links between biological networks. Furthermore with this method, the function and localisation of previously unknown proteins can be predicted by determining their interaction partners. It also can be used to predict the response of a cell to changes in the expression of particular members of the networks without making a molecular, cellular or animal experiment. Finally, these data can be used to identify proteins or interactions between proteins within a medically relevant pathway, which are suitable for therapeutic intervention, diagnosis or the treatment of a disease (FIG. 1).

In summary, a significant advantage of the method of invention over existing 2H systems is the ease of removal of false positives from sets of host cells designed for 2H screening experiments. A further advantage lies in the scale at which such identification of interactions and interaction members can be made. Due to the ease of automating the method of the invention at different stages, fast and reliable screening of large numbers of clones will be possible.

EXEMPLIFICATION

Example 1

Figure 4:
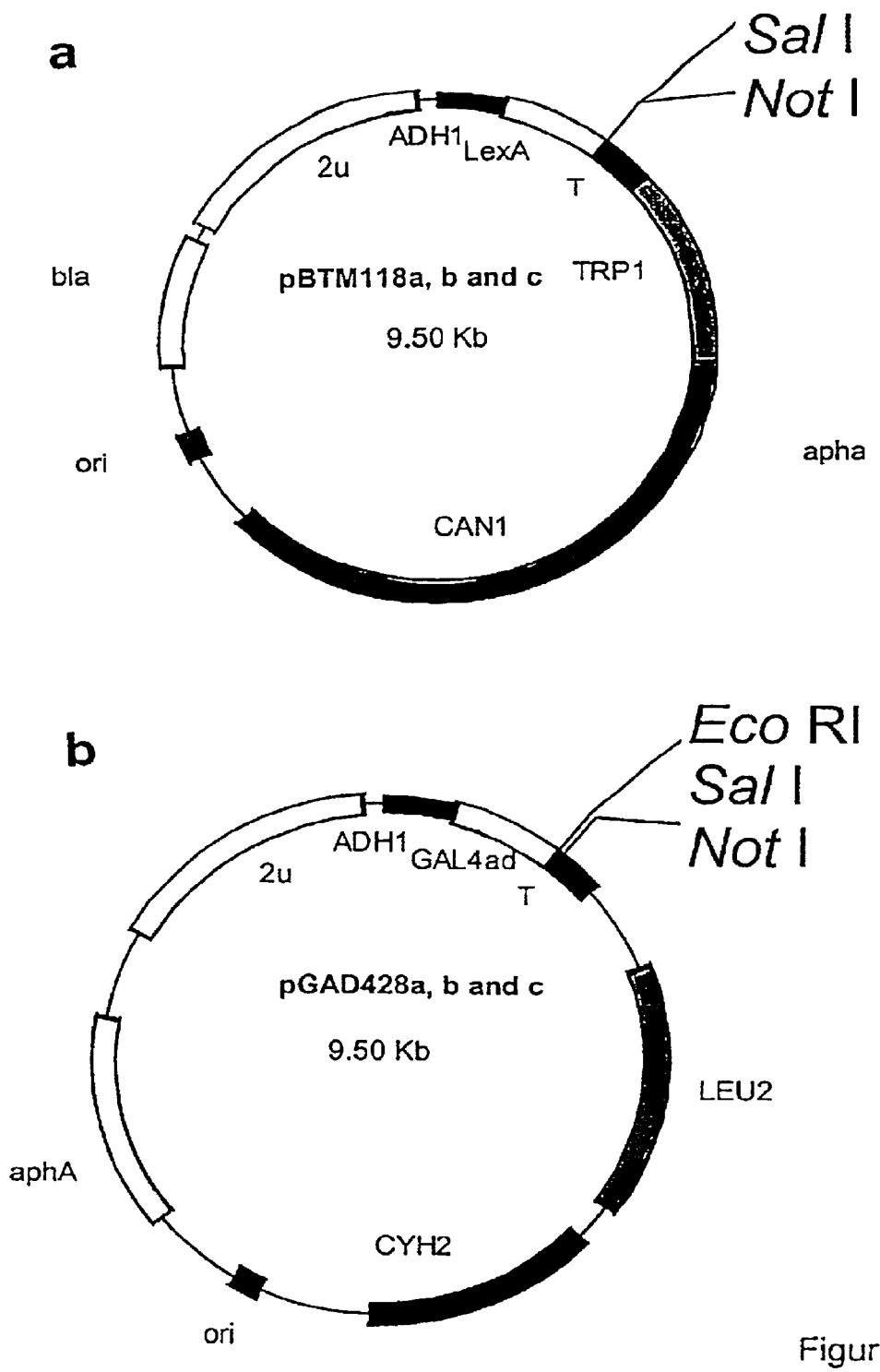

Construction of Vectors Yeast Strains and Readout System for an Improved Yeast Two-Hybrid System 1.1 Construction of Vectors The plasmids constructed for an improved yeast two-hybrid system pBTM118 a, b and c and pGAD428 a, b and c are shown in FIG. 4. Both sets of vectors can be used for the construction of hybrid (fusion) proteins. The vectors contain the unique restriction sites Sal I and Not I located in the multiple cloning site (MCS) region at the 3'-end of the open reading frame for either the lexA coding sequence or the GAL4ad sequence FIG. 4b).

With both sets of plasmids fusion proteins are expressed at high levels in yeast host cells from the constitutive ADH1 promoter (P) and the transcription is terminated at the ADH1 transcription termination signal (T). The two-hybrid plasmids shown in FIG. 4a are shuttle vectors that replicate autonomously in both E. coli and S. cerevisiae.

The three plasmids pBTM118 a, b and c are used to generate fusions of the LexA protein (amino acids 1–220) and a protein of interest cloned into the MCS in the correct orientation and reading frame. The plasmids pBTM118 a, b and c are derived from pBTM117c (Wanker et al., 1997) by insertion of the adapters shown in Table 1 into the restriction sites Sal I and Not I to generate the improved vectors with three different reading frames.

The plasmids pBTM118 a, b and c carry the wild type yeast CAN1 gene for counterselection, which confers sensitivity to canavanine in transformed yeast cells (Hoffmann, 1985). The plasmids also contain the selectable marker TRP1, that allows yeast trp1-auxotrophs to grow on selective synthetic medium without tryptophan, and the selectable marker bla which confers ampicillin resistance in E. coli.

The plasmids pGAD428 a, b and c are used to generate fusion proteins that contain the GAL4 activation domain (amino acids 768–881) operatively linked to a protein of interest. The plasmids pGAD428 a, b and c carry the wild type yeast CYH2 gene, which confers sensitivity to cycloheximide in transformed cells (Kaeufer et al., 1983), the selectable marker LEU2, that allows yeast leu2-auxotrophs to grow on selective synthetic medium without leucine, and the bacterial marker aphA (Pansegrau et al., 1987) which confers kanamycin resistance in E. coli. The plasmids pGAD428a, b and c were created from pGAD427 by ligation of the adapters shown in Table 1 into the MCS to construct the improved vectors with three different reading frames.

For the construction of pGAD427 a 1.2 kb Dde I fragment containing the aphA gene was isolated from pFG101u (Pansegrau et al., 1987) and was subcloned into the Pvu I site of the pGAD426 using the oligonucleotide adapters 5'-GTCGCGATC-3' and 5'-TAAGATCGCGACAT-3' (SEQ ID No. 8). The plasmid pGAD426 was generated by insertion of a 1.2 kb Eco RV CYH2 gene fragment, which was isolated from the pAS2-1 (Clonetech) into the Pvu II site of pGAD425 (Han and Collicelli, 1995).

1.2 Construction of Yeast Strains

To allow for the improved yeast two-hybrid system, three Saccharomyces cerevisiae strains L40 cc, L40 ccu and L40 ccuα were created. The S. cerevisiae. L40 cc was created by site specific knock-out of the CYH2 and CAN1 genes of L40 (Hollenberg et al., Mol. Cell. Biol. 15: 3813–3822), and L40 ccu created by site specific knock-out of the URA3 gene of L40 cc (Current Protocols in Molecular Biology, Eds. Ausubel et al. John Wiley & Sons: 1992) The strain L40 ccuα was created by conducting a mating-type switch of the strain L40 ccu by standard procedures (Ray BL, White Cl, Haber JE (1991)). The genotype of the L40 cc strain is: Mata his3Δ200 trp1-901 leu2-3,112 ade2 LYS2::(lexAop)$_4$-HIS3 URA3::(lexAop)$_8$-lacZ GAL4 can1 cyh2, The genotype of the L40 ccu strain is: Mata his3Δ200 trp1-901 leu2-3,112 ade2 LYS2::(lexAop)$_4$-HIS3 ura3::(lexAop)$_8$-lacZ GAL4 can1 cyh2, and that of L40 ccuα is Matα his3Δ200 trp1-901 leu2-3,112 ade2 LYS2::(lexAop)$_4$-HIS3 ura3::(lexAop)$_8$-lacZ GAL4 can1 cyh2.

1.3 Readout System

FIG. 5 shows the URA3 readout system carried by the plasmid pLUA. This URA3 readout system under the control of a bacterial LexAop upstream activation sequence (UAS) can be used within the yeast 2-hybrid system both as a counter selective reporter gene and as a positive selection reporter gene to eliminate false positive clones. The plasmid contains the features of the UAS$_{lexAop}$-URA3 readout system, the selectable marker ADE2 that allows yeast ade2-auxotrophs to grow on selective media without adenine and the bla gene which confers amplicillin resistance in *E. coli*. The plasmid pLUA is a shuttle vector that replicates autonomously in *E. coli* and yeast.

For the construction of pLUA a 1.5 kb Sac II/Ca I UAS$_{lexAop}$-URA3 fragment was isolated from pBS-lexURA and ligated together with a 2.4 kb Sac I/Cla I ADE2 fragment into Cla I digested pGAD425Δ. pBS-lexURA was generated by ligating URA3 fragment together with a UAS$_{lexAop}$ fragment into pBluescript SK+. The URA3 and UAS$_{lexAop}$ fragments were obtained by PCR using genomic DNA from *S. cerevisiae* strain L40c using standard procedures and anchor primers which gave rise to complementary overhangs between the two consecutive fragments which were subsequently anealed to generate the chimeric sequence (see, for example, Current Protocolls in Molecular Biology, Eds. Ausubel et al. John Wiley & Sons: 1992). The ADE2 gene was isolated by PCR using genomic DNA from SEY6210α. pGAD425A was generated by deleting of an 1.2 kb Sph I fragment from pGAD425 (Han and Colicelli, 1995) and religation of the vector.

1.4 Generation of a Defined Interaction Library

Figure 6I:
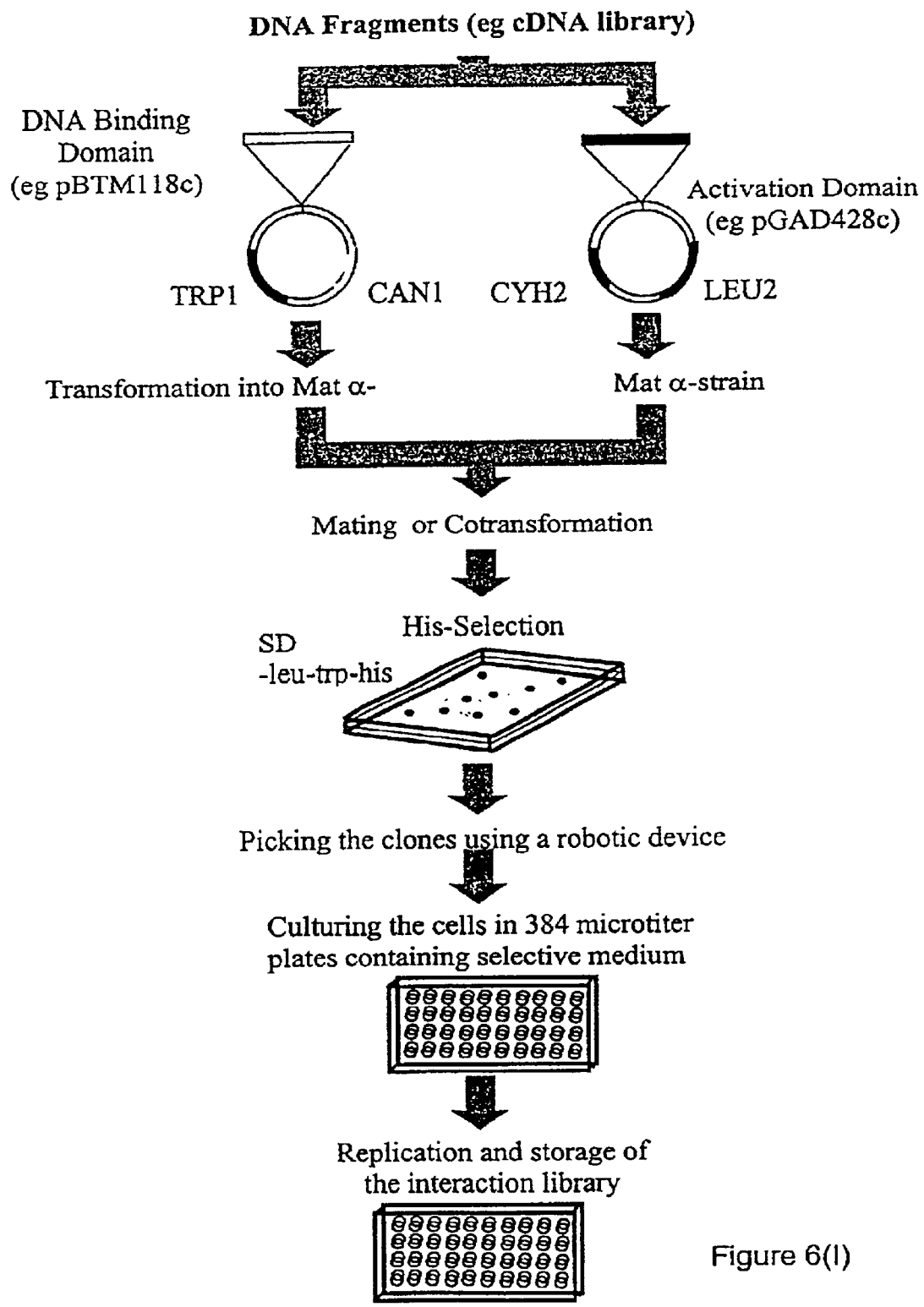
Figure 7I:
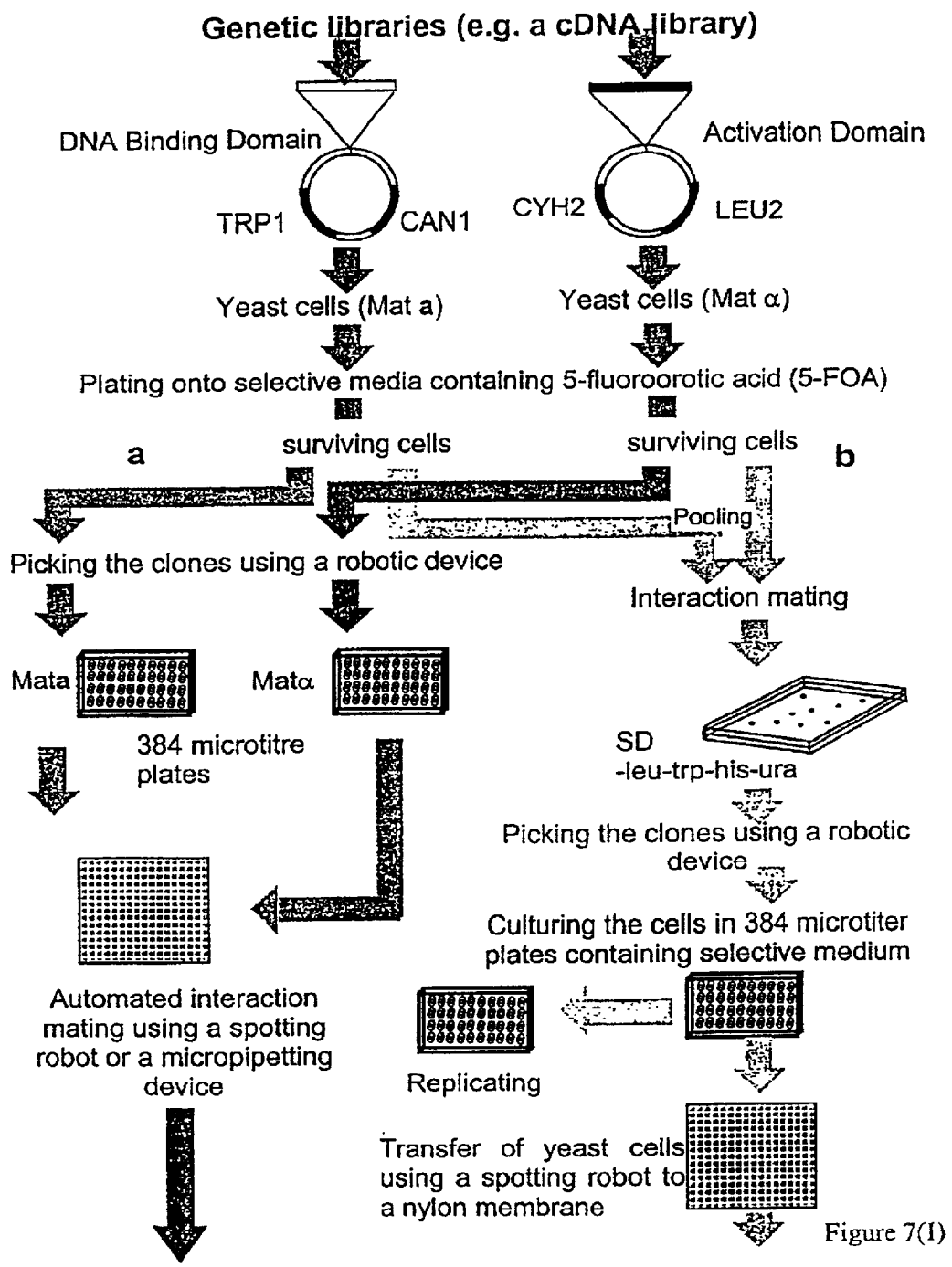

To determine if the invention could be used in an improved two-hybrid system for yeast, as shown in FIG. 6 or FIG. 7, a defined interaction library of plamids that express various LexA and GAL4ad fusion proteins of interest was constructed using the vectors and strains described in sections 1.1 and 1.2. The orientation of the inserted fragments was determined by restriction analysis and the reading frame was checked by sequencing. The generated constructs and the original plasmids described above are listed in Table 2. The construction of pBTM117c-HD1.6, —HD3.6 and —SIM1 was described elsewhere (Wanker et al., 1997; Probst et al., 1997). pBTM117c-HIP1 and pGAD427-HIP1 were obtained by ligation of a 1.2 kb Sal I HIP1 fragment isolated from pGAD-HIP1 (Wanker et al., 1997) into pBTM117c and pGAD427, respectively. pBTM117c-MJD was created by inserting a 1.1 kb Sal I/Not I MJD1 fragment (Kawagushi et al., 1994) into pBTM117c, and pGAD427-14-3-3 was generated by inserting a 1.0 kb EcoRI/NotI fragment of pGAD 10-14-3-3 into pGAD427. For the construction of pGAD427-HIPCT, a 0.5 kb Eco RI HIP1 fragment isolated from pGAD-HIPCT (Wanker et al., 1997) was ligated into pGAD427. pGAD427-lexA and pGAD427-ARNT were generated by insertion of a 1.2 kb Sal I/Not digested lexA PCR fragment and a 1.4 kb Sal I/Not I ARNT fragment into pGAD427 respectively.

It was shown that the fusion proteins LexA-SIM1 and GAL4ad-ARNT specifically interact with each other in the yeast two-hybrid system (Probst et al., 1997), because when both hybrids were coexpressed in *Saccharomyces cerevisiae* containing two integrated reporter constructs, the yeast HIS3 gene and the bacterial lacZ gene, which both contained binding sites for the LexA protein in the promoter region, the interaction between these two fusion proteins led to the transcription of the reporter genes. The fusion proteins by themselves were not able to activate transcription because GAL4ad-ARNT lacks a DNA binding domain and LexA-SIM1 an activation domain (Probst et al., 1997). In contrast it was shown recently that the fusion proteins LexA-HIP1 and GAL4ad-LexA are capable of activating the HIS3 and lacZ reporter genes without interacting with a specific GAL4ad or LexA fusion protein respectively. Thus, the yeast clones expressing the LexA-HIP1 protein have to be designated as false positives, because false positives are defined here as clones where a GAL4ad fusion protein or a LexA fusion protein alone without the respective partner protein activates the transcription of the reporter genes without the need for any interacting partner protein.

Figure 8:
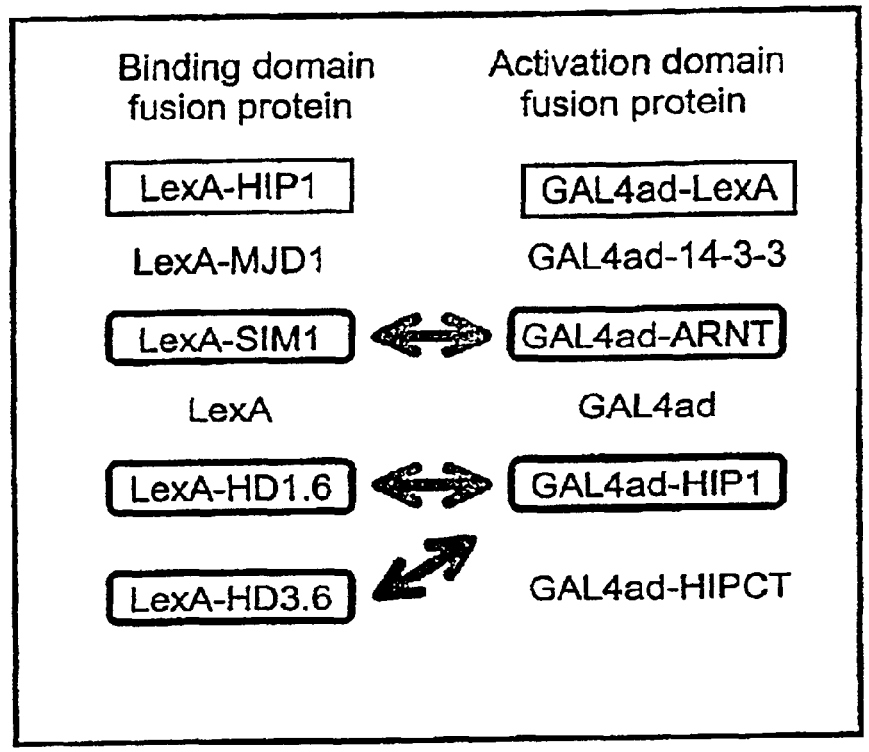

The predicted protein—protein interactions of these fusion proteins are shown in FIG. 8. It was shown that the fusion proteins LexA-SIM1 & GAL4ad-ARNT, LexA-HD1.6 & GAL4ad-HIP1 and LexA-HD3.6 & GAL4ad-HIP1 specifically interact with each other in the yeast two-hybrid system because they only activate the reporter genes HIS3 and lacZ when both proteins are present in one cell (Probst et al. 1997; Wanker et al. 1997). In contrast, it was demonstrated that the LexA-HIP1 and GAL4ad-LexA fusion proteins are capable of activating the reporter genes without the need for any interacting fusion protein. The proteins LexA and GAL4ad and the fusion proteins LexA-MJD and GAL4ad-14-3-3 which are also present in the defined interaction library are unable to activate the reporter genes either alone or when present in the same cell with any other fusion proteins comprising the library.

Example 2

Figure 9:
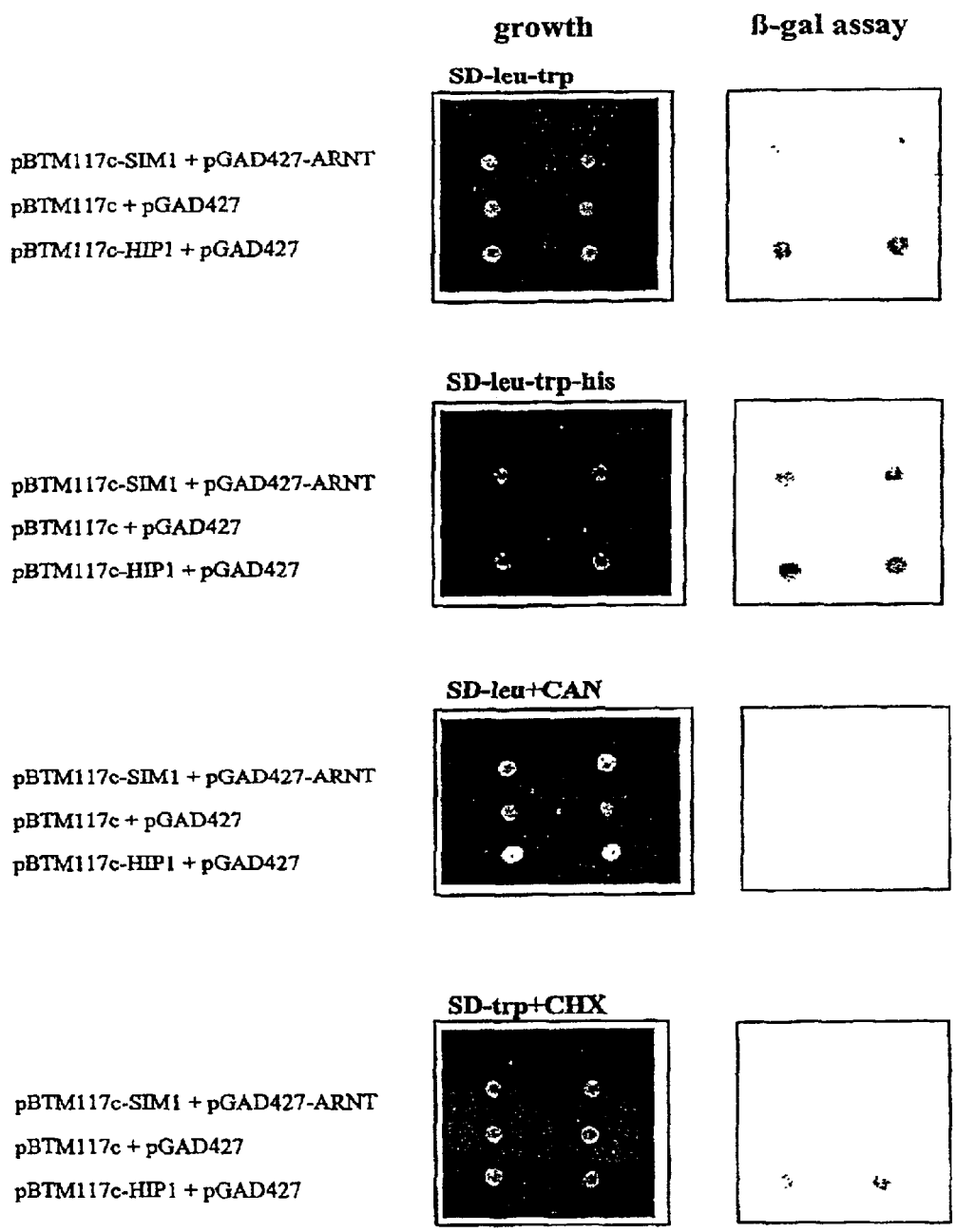

Detection of Clones Expressing Known Interacting Proteins from False Positives Using the Improved Two-Hybrid System Pairs of the yeast two-hybrid plasmids pBTM117cSIM1 & pGAD427-ARNT, pBTM117c & pGAD427 and pBTM117c-HIP1 & pGAD427 were transformed into the yeast strain L40 cc, and Trp+Leu+ transformants that contained at least one of each of the two plasmids were selected on SD-leu-trp plates. Two transformants from each transformation were investigated for the presence of protein—protein interactions by testing the ability of the yeast cells to grow on SD-leu-trp, SD-leu-trp-his, SD-leu+CAN and SD-trp+CHX plates and by the β-galactosidase membrane assay (Breeden and Nasmyth, 1985). FIG. 9 shows that the yeast strains cells harboring both the plasmids pBTM117c-SIM1 & GAD427-ARNT or pBTM117c-HIP1 & pGAD427 grow on SD-leu-trp-his plates and turned blue after incubation in X-Gal solution, indicating that the HIS3 and lacZ reporter genes are activated in these strains. In comparison, the yeast strain harboring both the negative control plasmids pBTM117c & pGAD427 was not able to grow on this medium and also showed no lacZ activity. After selection of the yeast strains harboring the different combinations of the two-hybrid plasmids on SD-leu+CAN and SD-trp+CHX the resulting strains were also analyzed by the β-galactosidase assay. After incubating the membrane containing all three strains on SD-trp+CHX medium only progeny of the yeast strain that originally harbored both the plasmids pBTM117c-HIP1 & pGAD427 yet which had lost the pGAD427 plasmid through counterselection turned blue after incubating in X-Gal solution. This result indicates that this clone is a false positive, because although showing a lacZ+ phenotype when grown on SD-leu-trp-his medium, the LexA-HIP1 fusion protein was also capable of activating the HIS3 and lacZ genes on SD-trp+CAN medium without the need for any interacting fusion protein. In comparison, the yeast strain harboring both the plasmids pBTM117c-SIM1 & pGAD427-ARNT is a positive clone that expresses interacting LexA and GAL4ad fusion proteins, because both the LexA and the Gal4ad fusion proteins are necessary for the activation of the reporter genes. If either of the plasmids pBTM117c-SIM1 or pGAD427-ARNT is lost from the strain by counterselection on SD-trp+CHX or SD-leu+CAN, respectively, the resulting cells are no longer able to activate the lacZ reporter gene and do not turn blue after incubation in X-Gal solution. With the membranes from the SD-leu+CAN plate false positive clones expressing an auto-activating GAL4ad-LexA fusion protein were also detected by the β-galactosidase assay.

Example 3

Generation of Regular Grid Patterns of Host Cells Expressing Potentially Interacting Fusion Proteins 3.1 Generation of a Regular Grid Pattern of Clones from an Interaction Library in Microtiter Plates Using Automation To generate the well defined interaction library, the constructs for the expression of the fusion proteins shown in FIG. 8 were pooled and 3 μg of the mixture was co-transformed into yeast strain L40 cc by the method of Schiestel & Gietz (1989). The yeast cells co-transformed with the constructs described in Table 2 were plated onto large 24×24 cm agar trays (Genetix, UK) containing minimal medium lacking tryptophan leucine and histidine (SD-leu-trp-his). The agar trays were poured using an agar-autoclave and pump (Integra, Switzerland) to minimise tray-to-tray variation in agar colour and depth. To maximise the efficiency of automated picking, the transformation mixture were plated such that between 200 and 2000 colonies per agar tray were obtained after incubation at 30° C. for 4 to 7 days.

Suitable changes to the hardware and software of a standard picking robot designed for the picking of *E. coli* cells, as described by Lehrach et al. (1997) were made to account for the specific requirements of yeast cells. The illumination of agar-trays containing plated colonies was changed from the dark-field sub-illumination to dark-field top-illumination to differentiate yeast colonies from the lawn of non-transformed cells. The existing vision guided motion system (Krishnaswamy & Agapakis 1997) was modified to allow for a larger range of 'blob' size when selecting yeast colonies to pick from the blob-feature-table returned by connectivity algorithms when applied to a digital image of the agar tray containing colonies. The clone inoculation routine was re-programmed to ensure that cell material which had dried on the picking pins during the picking routine was initially re-hydrated by 10 seconds of immersion in the wells of a microtiter plate before vigorous pin-motion within the well. This robotic procedure ensured that sufficient cell material was inoculated from each picking pin into an individual well of a microtiter plate. The picking pins were sterilised after inoculation to allow the picking cycle to be repeated by programming the robot to brush the picking pins in a 0.3% (v/v) solution of hydrogen peroxide, followed by a 700% ethanol rinse from a second wash-bath and finally drying by use of a heat-gun to evaporate any remaining ethanol from the pins. Furthermore, an algorithm to automatically correct for height variation in the agar was incorporated by referencing the surface height of the agar in three corners and from these points automatically estimating the surface plane of the agar. The robot was further programmed to automatically adjust both the imaging and picking heights according to the agar surface height such that when a pin was extended into a colony, it removed cells only from the top surface of the colony and did not penetrate the whole colony into the growth medium. Finally, we incorporated additional selection criteria that would reliably sort between blue and white colonies. Although the robot provided a method to select only those 'blobs' (colonies) within a range of average grey scales (eg, >80 for white colonies), this proved unreliable since the actual value of average grey scale required to make a correct discrimination varied across the agar-tray due to slight variation in intensity of the illumination. Therefore, a new method was implemented that automatically modified this discrimination value based on the average illumination of a region of the agar-tray as measured by the camera on a frame-to-frame basis. Often, a 'blue' colony that activated the readout system was not uniformly blue across the its whole area, but only the centre would be blue and the surrounding cell material was white. In such cases, the connectivity algorithms would detect two 'blobs'—one (the blue centre) lying directly on the other (the white surrounding) and although the former would be ignored since it was blue, the latter would be selected as its average grey-scale was greater than the discrimination value. Such cases were successfully selected against by ignoring any colonies that had 'holes' using a 'number of holes' function of the image analysis program, which flags those blobs which have a second blob within their boundary.

Using these modifications to a laboratory picking robot, individual yeast colonies were automatically picked from the agar-trays into individual wells of a sterile 384-well microtiter plate (Genetix, UK) containing sterile liquid minimal medium lacking leucine and trptophan (SD-leu-trp) and containing 7% (v/v) glycerol. The resulting microtiter plates were incubated at 30° C. for 36 hours, the settled colonies were dispersed by vigorous mixing using a 384-well plastic replicating tool (Genetix, UK) and then incubated for a further 2 to 4 days. A picking success of over 90% wells containing a growing yeast culture was achieved. After growth of yeast strains within the microtiter plates, each plate was labelled with a unique number and barcode. Each plate was also replicated to create two additional copies using a sterile 384-pin plastic replicator (Genetix, UK) to transfer a small amount of cell material from each well into pre-labelled 384-well microtiter plates and pre-filled with SD-leu-trp-his/7% glycerol liquid medium. The replicated plates were incubated at 30° C. for 3 days with a cell dispersal step after 36 hours, subsequently frozen and stored at −70° C. together with the original picked microtiter plates of the interaction library.

In this manner, a regular grid pattern of yeast cells expressing potentially interacting yeast clones was generated using a robotic and automated picking system. 384-well microtiter plates have a well every 4.5 mm in a 16 by 24 well arrangement. Therefore, for each 384-well microtiter plate a regular grid pattern at a density greater that 4 clones per square centimetre was automatically created.

3.2 Creation of Regular Grid Patters of Increased Density

To generate arrays with higher densities, a computer-controlled 96-well pipetting system (Opal-Jena) with automatic plate-stacking, tip washing, liquid waste and accurate x-y positioning of the microtiter plate currently accessed by the tips was employed. The yeast two hybrid cells that had settled in the bottom of the wells of the arrayed interaction library as described above were re-suspended, and a stack of these 384-well plates were placed into the input stacker of the pipetting system. The system was programmed to take a single 384-well microtiter plate containing the arrayed yeast two-hybrid clones and parallel aspirate 10 μl of culture medium and cells into each of the 96 pipette tips from 96 wells of the 384-well plate. The inter-tip spacing of the 96 tips was 9 mm and the wells of the 384-well microtiter plate were 4.5 mm so that cells were removed from only every other well along each dimension of the 384-well plate. 8 μl of the 96 aspirated samples contained in the tips were then pipetted in parallel into one set of wells of a sterile 1536-well microtiter plate (Greiner, Germany). Since the inter-well spacing of this 1536-well microtiter plate is 2.25 mm, yeast cells were deposited into only 1 every 4 wells along each dimension of the 1536-well plate. The remaining 2 µl of culture medium and cells was aspirated to waste before sterilising each 96 tips in parallel. Sterilisation was conducted by twice aspirating and washing to waste 50 µl of 0.3% (v/v) hydrogen peroxide stored in a first replenishable wash-bath on the system, and then aspirating and washing to waste 50 µl sterile distilled water stored in a second replenishable wash-bath.

This plate-to-plate pipetting cycle was repeated 3 further times, each time aspirating a different set of 96-clones from the 384-well array of yeast 2-hybrid clones into a different set of 96wells in the 1536-well microtiter plate by moving the microtiter plates relative to the 96-tips using the accurate x-y positioning of the system. When all clones of the first 384-well microtiter plate had been sampled and arrayed into the 1536-well plate, the first 384-well microtiter plate was automatically exchanged for the next 384-well microtiter plate, and the yeast 2-hybrid clones arrayed in this second 384-well plate were similarly arrayed into the 1536-well plate. When the yeast 2-hybrid clones contained within four 384-well microtiter plates had been automatically arrayed in the first 1536-well plate, filling all wells, the 1536-well plate was automatically exchanged for a second sterile 1536-well plate stored in the second stacking unit of the pipetting system. The whole process was repeated until all yeast 2-hybrid clones of the interaction library had been automatically transferred form 384-well to 1536-well microtiter plates.

In this manner, a regular grid pattern of yeast cells expressing potentially interacting yeast clones using a computer-controlled pipetting system was generated. 1536-well microtiter plates have a well every 2.25 mm in a 32 by 48 well arrangement. Therefore, for each 1536-well microtiter plate we automatically created a regular grid pattern at a density greater than 19 clones per square centimetre.

3.3 Generation of a Regular Grid Pattern of Clones from an Interaction Library on Porous Carriers Using Automation A high-throughput spotting robot such as that described by Lehrach et al. (1997) was used to construct porous planar carriers with a high-density regular grid-pattern of yeast clones from the defined interaction library contained within 384-well microtiter plates. The robot recorded the position of individual clones in the high-density grid-pattern by the use of a pre-defined duplicate spotting pattern and the barcode of the microtiter plate. Individually numbered membrane sheets sized 222×80 mm (Hybond N+, Amersham UK) were pre-soaked in SD-leu-trp-his medium, carefully laid on a sheet of 3 mm filter paper (Whatmann) pre-soaked in the same medium and placed in the bed of the robot. The interaction library was automatically arrayed as replica copies onto the membranes using a 384-pin spotting tool affixed to the robot. Five different microtiter plates from the first copy of the interaction library were replica spotted in a '3×3 duplicate' pattern around a central ink guide-spot onto 10 nylon membranes —corresponding to approximately 1900 clones spotted at a density of approximately 40 spots per cm$^2$. On each replica membrane three different control clones were spotted, each from a microtiter plate that contained the same control clone in every well. One control clone expressed the fusion proteins LexA-SIM1 & GAL4ad-ARNT, a second control clone the fusion protein LexA-HIP1, while a third expressed fusion protein GAL4ad-LexA, and all were spotted in order to test the selection, counterselection and the β-gal assay features of the method. To ensure the number of yeast cells on each spot was sufficient for those membranes which were to be placed on the counterselection media plates, the robot was programmed to spot onto each spot position 5 times from a slightly different position within the wells of the microtiter plates. The robot created a data-file in which the spotting pattern produced and the barcode that had been automatically read from each microtiter plate was recorded.

Each membrane was carefully laid onto approximately 300 ml of solid agar media in 24×24 cm agar-trays. Six membranes were transferred to SD-leu-trp is media and two each of the remaining membranes were transferred to either SD-trp+CHX or SD-leu+CAN media The yeast colonies were allowed to grow on the surface of the membrane by incubation at 30° C. for 3 days.

3.4 Generation of a Regular Grid Pattern of Clones from an Interaction Library on Non-Porous Carriers Using Automation The plasmid pGNG1 (MoBiTec, Germany) carries a green fluorescent protein variant under the control of a LexA operator. This variant, GFPuv, is up to 16 times brighter that the wild-type variant isolated from *Aequora Victoria* (Ausubel et al., 1995; Short protocols in molecular biology, 3$^{rd}$ ed. John. Wiley & Sons, New York, N.Y.). The yeast 2 um origin of replication and the auxotrophic marker URA3 maintains the plasmid in ura3 mutant yeast strains. This plasmid should act as a readout system to detect single fusion proteins or interacting fusion proteins able to activate the readout system in the method of invention described herein. As is known in the art, green fluorescent proteins and its variants are considered suitable reporter genes in most host-cell types. Therefore, it would be possible for a person skilled in the art to incorporate this gene within other host-cell types and interaction systems as disclosed in this invention.

The yeast strain L40 ccu was transformed with the plasmid pGNG1 (MoBiTec, Germany) using the method of Schistel & Gietz (1989), and a resulting stable transformant clone cultured in minimal medium lacking uracil and subsequently used to generate two further yeast clones, each containing two genetic elements. The first strain, GNGp, was generated by co-transformation of a mixture of the plasmids pBTM117c-SIM1 and pGAD427-ARNT co-transformed into L40 ccu already carrying the reporter plasmid pGNG1. The second strain, GNGn, was generated by co-transformation of a mixture of the plasmids pBTM117c-MJD and pGAD427-14-3-3 co-transformed into L40 ccu already carrying the reporter plasmid pGNG1. In both cases, the transformations were conducted using the method of Schistel & Gietz (1989), and transformants were selected by plating on minimal media lacking uracil, trp-tophan and leucine.

Individual colonies from the two transformations were picked into individual wells of 384-well microtiter plates as described in section 3.1 except that the microtiter plates contained liquid minimal medium lacking uracil, tryptophan and leucine. One microtiter plate was created that contained individual colonies of the GNGp yeast strain, and another carrying colonies of GNGn. Using a spotting robot (Lehrach et al., 1997) fitted with high precision spotting tool carrying 16 pins in a 4×4 pattern, the clones were arrayed onto poly-lysine coated glass-slide (Sigma, US). The clones were spotted at a spacing of 440 um, with a spot diameter of approximately 300 um generating a density of over 490 clones per square centimetre. To increase the amount of cell material depositied at each spot, the robot was programmed to spot onto each spot position 10 times from a slightly different position within the wells of the microtiter plates. It is well known in the art that piezo-ink-jet micropipetting systems (Kietzmann et al., 1997, Schober et al., 1993) can create regular grid pattern of clones at an even greater density. Indeed, grid densities of over 1600: spots per quare centimeter have been achieved with such systems.

The fluorescent readout system of cells in the regular grid pattern of cells was then visualised using a sensitive CCD camera (LAS1000, Fuji, Japan). Appropriate excitation light was provided and an emission filter appropriate for the emission spectrum of $GFP_{uv}$ was fitted to the lens. Other imaging systems could be utilised to investigate the regular grid pattern of clones. For example, laser-scanning systems including laser scanning confocal microscopes would be preferred when imaging very high density regular grid patterns, or for those formed from a small number of host cells deposited at each position.

It was shown that the fusion proteins LexA-SIM1 and GAL4ad-ARNT can interact and activate a readout system under control of the LexA operator. Since the $GNG_{uv}$ reporter gene is under the control of a LexA operator, a cell carrying the pGNG1 plasmid and expressing these fusion proteins should fluoresce under UV light. In contrast, the fusion proteins LexA-MJD and GAL4-14-3-3 were shown unable to activate the same readout system. Image analysis of the digital image of the regular grid pattern of yeast cells, demonstrated that indeed, the GNGp yeast strain did fluoresce while the GNGn did not.

As an alternative to pGNG1 a person skilled in the art could subclone an improved GFP mutant as described in Anderson et al. (1996). *Replacement of the URA coding sequence in pLUA* (section) with GFP is performed by using appropriate anchor primer to amplify the GFP mutant. Using the appropriate growth media the analysis can be performed as described above.

Example 4

Detection of the Readout System in a Regular Grid Pattern 4.1 Detection of Readout System Activation in a Regular Grid Pattern of Clones from an Interaction Library on Planar Carriers Using Digital Image Capture, Processing and Analysis Two membranes from each of the selective media described in section 3.3 were assayed for lacZ expression using the β-gal assay as described by Breeden & Nasmyth (1985) and air dried overnight For each membrane, a 24-bit digital BMP (bitmap) image of the β-gal assay was captured using a standard A3 computer scanner, and the images were stored on computer. The yeast strain used to create the defined interaction library was an ade2 auxotrophic mutant, and those colonies that grew yet did not activate the readout system were pink in colour when mature. Since image analysis programs used for the analysis of DNA grids use single channel (grey-scale) images, it was necessary to convert this colour image to an 8-bit grey-scale image. However, the pink colour of colonies not expressing the β-gal reporter gene, when converted to grey-scale, would lower the contrast between positive and negative activation states of the readout system. Therefore, the pink-red colours of the image were re-mapped to light yellow before processing the remapped 24-bit colour image to a colour-inverted 8-bit grey-scale TIF (tagged image file format) using the software Photo Magic (Micrografix, USA). One non-inverted 8-bit grey-scale image of the defined interaction library that was grown on membranes placed on each of the 3 selective media and subsequently assayed for β-gal activity is shown in FIG. 10.

Individual clones of the interaction library can be identified and their position on the high-density spotted filter converted to specific wells in the microtiter plates using an automated image analysis system as described by Lehrach et al. (1997). Here, the basic grid and node position of each clone is determined through an iterative sampling scheme proposed by Geman & Geman (1984). Once the node positions have been determined, the average grey-scale value of a pixel mask appropriately sized for the average colony diameter is recorded from the image for every colony on the filter. From these intensity data, global and block-specific background corrections are made, giving greater weight to the local block-specific background. Each colony is then classified into one of four β-galactosidase activities by appropriate binning values of the background-corrected intensities.

Positive clones that expressed interacting fusion proteins were detected from false positive clones by considering the activity of β-galactosidase of clones grown on spotted membranes laid on the various selective media Positive clones should activate the lacZ reporter gene on SD-leu-trp-his media and turn blue on incubation with X-Gal solution, but not on either of the two counterselective media False positive clones should activate the reporter gene and turn blue on incubation with X-Gal solution on at least one counterselective media as well as on the SD-leu-trp-his medium.

Figure 11:
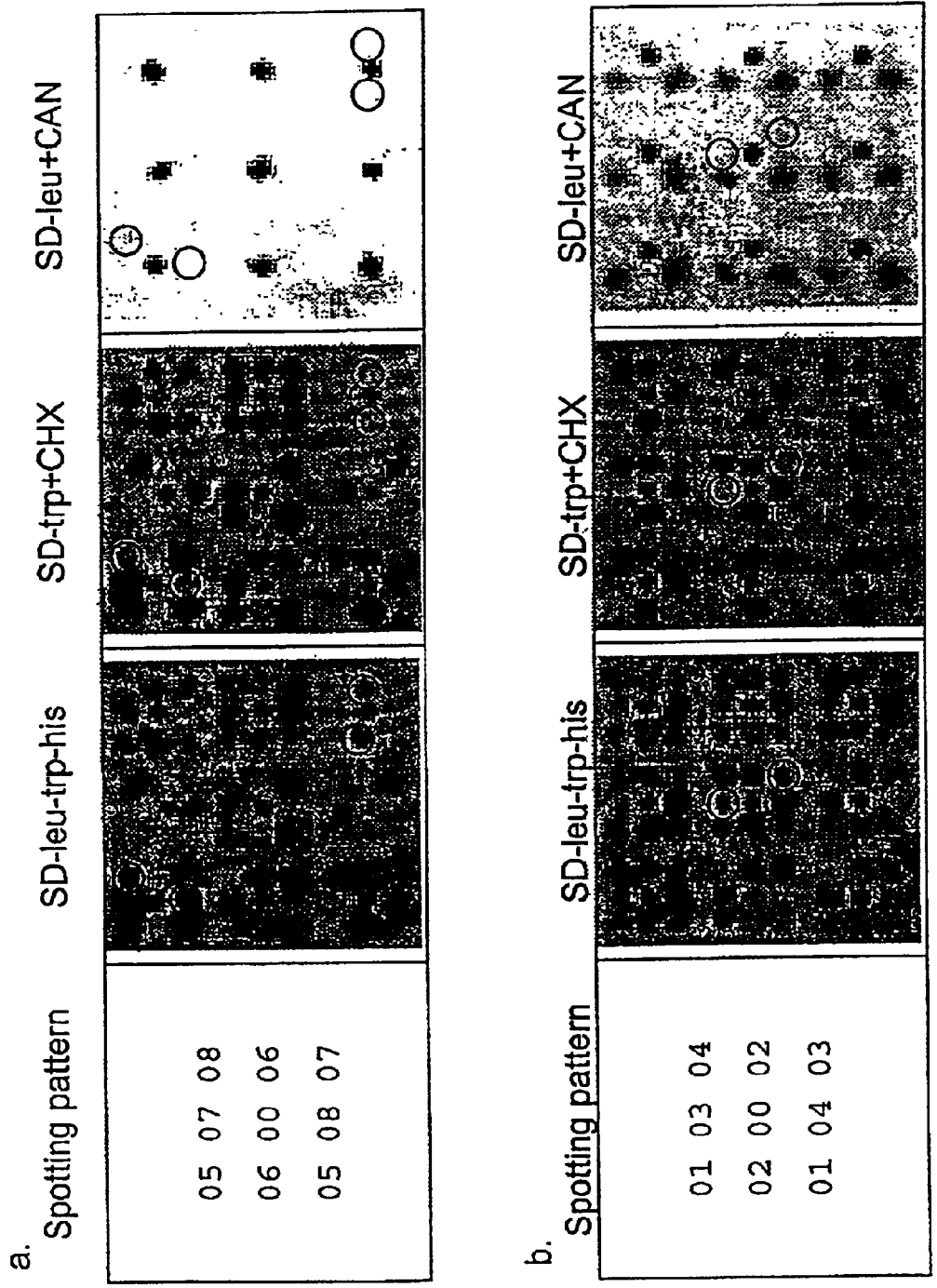

FIG. 11 shows magnified images of a β-gal assay of clones grown on the membranes which had been placed on the three selective media. Within the magnified region of the membranes shown in FIG. 11a, two clones were detected as positive clones that express interacting fusion proteins since they activated the lacZ reporter gene on SD-leu-trp-his media, but not on either of the two counterselective media, and whose spotted positions are circled. The two clones were identified by their microtiter plate address within the interaction library as 06L22 and 08N24 respectively. All other clones spotted within this region of the membrane were detected as false positive since they express β-galactosidase on SD-trp+CHX medium as well as on SD-leu-trp-his medium.

Expression of the LacZ reporter gene for the three control clones spotted onto the same membranes confirm these results. The positive control clone that expresses the interacting fusion proteins LexA-SIM1 & GAL4ad-ARNT should show a LacZ+phenotype when grown on SD-leu-trp-his medium, but LacZ– when grown on either of the counterselective media. This control clone was spotted at position 03 in the region of the membranes shown in FIG. 11b, of which one example is circled. The pattern of β-gal activity for this positive control clone on the three selective media is as predicted. The false positive control clone that expresses the fusion protein LexA-HIP1 and the false positive clone that expresses the fusion protein GAL4ad-LexA are spotted at positions 02 and 01 respectively. Both false positive control clones show a LacZ+ phenotype when grown on SD-leu-trp-his media, but are detected as false positive clones by the method of the invention since they also show a LacZ+phenotype on SD-leu+CAN or SD-trp+CHX media, respectively. The clones spotted at position 04 are from the defined interaction library, and from their LacZ+phenotype when grown on SD-leu+CAN media are predicted to be false positive clones.

The image analysis system described above was used to automatically identify those individual clones on each high-density regular grid pattern that had activated the LacZ readout system. This was conducted for each of the membranes grown on the three selective media, and the intensity of β-galactosidase activity for each clone grown on the three media was automatically recorded by the program using a scale from 0 to 3 (no activity, weak activity, medium activity, high activity). These data for all clones on a given membrane were saved in a computer file, and the β-galactosidase activity for a given clone was related to its activity when grown on the other two selective media using a computer program. This program was used to query and identify all clones from the interaction library that had activated the reporter gene when grown on SD-leu-trp-his (score greater than 0), yet had not on either of the counterselective media (score on both media equal to 0). FIG. 12a shows a subset of these clones identified using this data-query procedure, and FIG. 12b shows that the two clones 06L22 and 08N24 are found within this automatically identified data-set of positive clones.

4.2 Detection of Readout System Activation in a Regular Grid Pattern of Clones from an Interaction library in microtiter plates using digital image capture, processing and analysis.

The interaction library comprising the yeast cells as described in section 3.1 were screened in microtiter plate format to identify those cells that express interacting fusion proteins. First, microtiter plates containing the interaction library were removed from frozen storage and thawed to room temperature. Second, each plate was replicated and labelled as described in section 3.1 to create additional copies for screening, each into 3 separate selective media Cells were transferred into 384-well microtiter plates pre-filled with 40 ul of the liquid selective media SD-leu-trp, SD-leu+Can or SD-trp+CHX. Third, after growth for 4 days at 30° C., 10 ul of Yeast One Step Yeast Lysis Buffer containing Galacton-Star and Sapphire II (Tropix, US) was added, the cells were dispersed using a plastic replication tool, and the plates incubated for 40 min at 37° C. Finally, a digital image of six plates was obtained in parallel using a LAS1000 CCD camera (Fuji, Japan), by placing the plates side-by-side in a two by three arrangement. The β-galactisidase substrate, Galacton-Star in combination with Sapphire II (Tropix, US) generates detectable luminescent light on activation of the β-gal reporter gene in the yeast-cells, and an exposure time of 5 minutes was used to collect sufficient signal. The grey-scale digital images were captured, saved on computer and subsequently analysed using the image analysis system described in section 4.1. However, in this case, the position of each clone was far simpler to determine due to the lower density of the regular grid pattern of clones in the microtiter plate. Second, the size of the pixel mask used to measure the average pixel intensity was approximately that of the size of the microtiter plate well. Positive clones in the six microtiter plates were identified by image analysis of the digital images from clones grown in the three selective media, and these data processed by the computer program as described in section 4.1.

Example 5

Identification of Individual Members of the Interaction

The interaction library constructed for this example was composed of known fusion proteins with predicted interactions as shown in FIG. 8. A real positive clone from this defined interaction library is therefore expected to express the interacting fusion protein-pairs LexA-SIM1 & GAL4ad-ARNT, LexA-HD1.6 & GAL4ad-HIP1 or LexA-HD3.6 & GAL4ad-HIP1 and hence contain the corresponding pairs of plasmid constructs pBTM117c-SIM1 & pGAD427-ARNT, pBTM117c-HD1.6 & pGAD427-HIP1 or pBTM117c-HD3.6 & pGAD427-HIP1, respectively. The identification of individual members that comprise an interaction between fusion proteins that are expressed within a single cell can be made by a variety of means as outlined in FIG. 1, FIG. 6 and FIG. 7. Three independent methods, nucleic acid hybridisation, PCR and DNA sequencing were used to identify the individual plasmid constructs that expressed the interacting fusion proteins in the positive clones 06L22 and 08N24.

Figure 13:
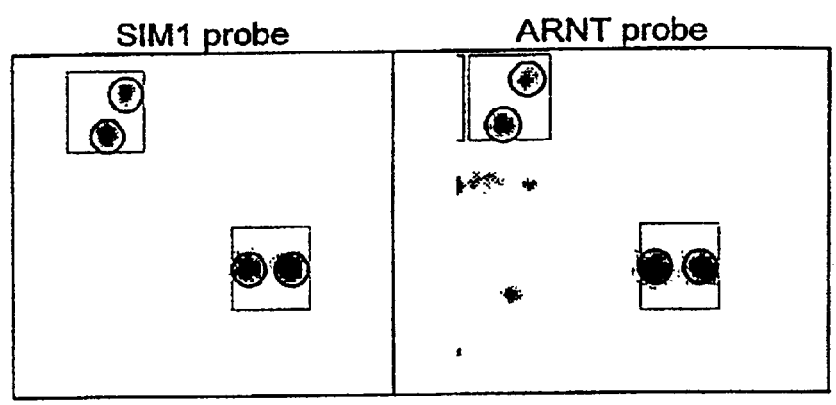

5.1 Identification of Individual Members of the Interaction by Nucleic Acid Hybridisation The four membranes which had been placed on the SD-leu-trp-his medium and had not been used to assay β-gal activity were processed according to the procedure described in Larin & Lehrach (1990) in order to affix the DNA contained within the clones of the interaction library onto the surface of the membrane. A 1.1 kb DNA fragment of SIM1 and a 1.3 kb DNA fragment of ARNT were radioactively labeled by standard random priming procedures for use as a hybridisation probe (Feinberg & Vogelstein, 1983). Each probe was heat denatured for 10 min at 95° C. and hybridised overnight at 65° C. in 15 ml of 5% SDS/0.5M sodium phosphate (pH 7.2)/1 mM EDTA with a high-density spotted membrane with DNA from the interaction library affixed to it as prepared above. The membranes were washed once in 40 mM sodium phosphate/0.1% SDS for 20 min at room temperature and once for 20 min at 65° C. before wrapping each membrane in Saran wrap and exposing it overnight to a phosphor-storage screens (Molecular Dynamics, USA). A digital image of each hybridised membrane was obtained by scanning the phosphor-storage screen using a phosphor-imager (Molecular Dynamics, USA). The digital image was stored on computer and was analyzed using the image analysis system for the analysis of DNA arrays as described in Lehrach et al., 1997 which marked positive hybridisation signals with square blocks. FIG. 13 shows a magnified region of each hybridised membrane corresponding to that shown in FIG. 11a containing the clones 06L22 and 08N24, the spotting position of which are circled. These clones were predicted to express either the interacting fusion protein-pairs LexA-SIM1 & GAL4adARNT, LexA-HD1.6 & GAL4ad-HIP1 or LexA-HD3.6 & GAL4ad-HIP1, and hybridisation with the specific SIM1 and ARNT probes have shown that both clones contain the plasmid constructs pBTN117c-SIM1 and pGAD427-ARNT.

Figure 14:
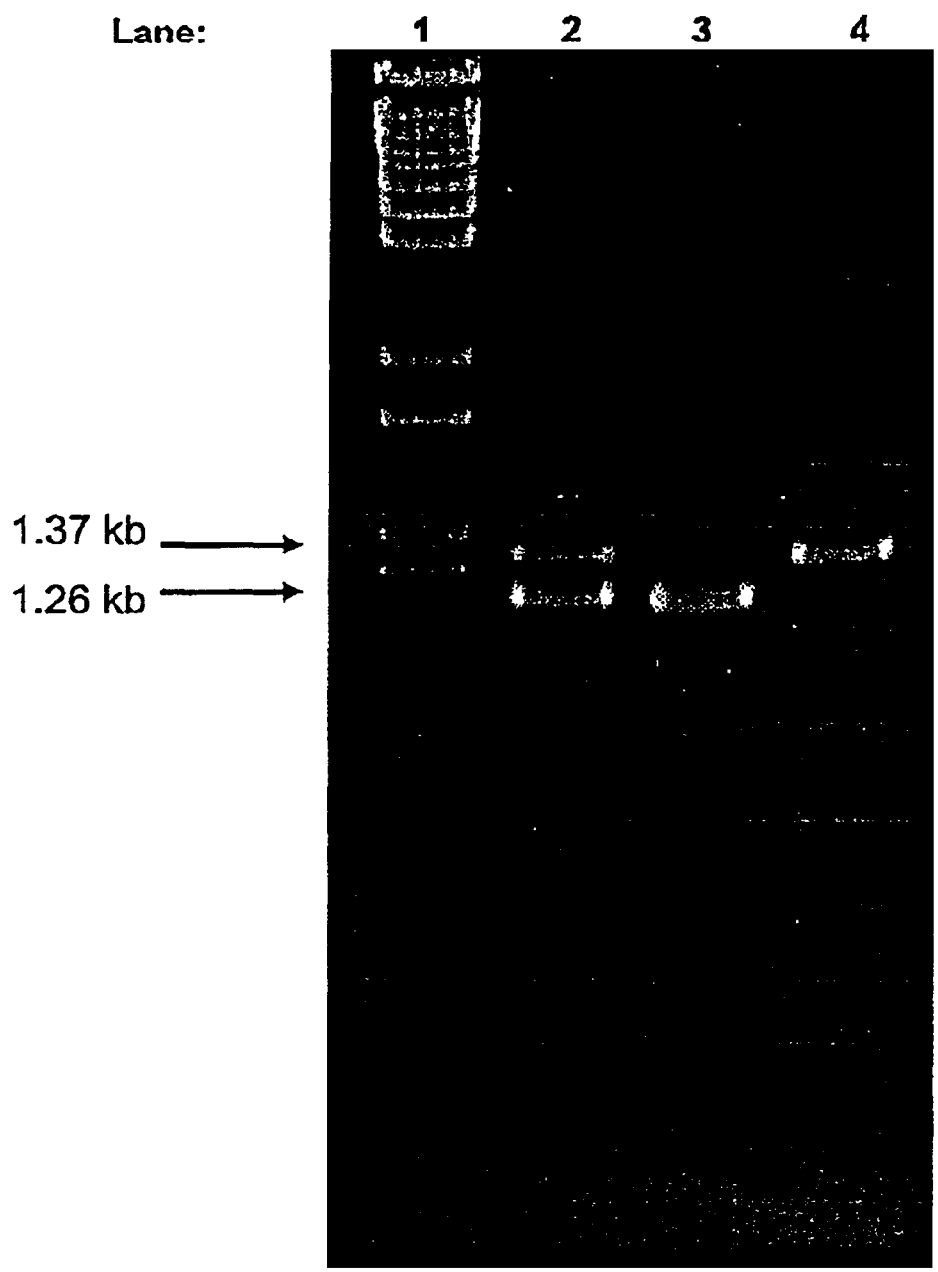

5.2 Identification of the Individual Members of the Interaction by Nucleic Acid Amplification and Sequencing The individual clone 06L22 was recovered from the frozen plates of the original interaction library and inoculated into SD-leu-trp-his liquid medium. This culture was allowed to grow for 3 days at 30° C. and the corresponding plasmids contained in the clone were isolated using a QiaPrep (Qiagen, Hilden) procedure. Duplex PCR was used to simultaneously amplify the inserts contained within the plasmid constructs using primer-pairs specific for either the pBTM117 or pGAD427 plasmids. The presence of the SIM1 and ARNT inserts was confirmed for clone 06L22 by electrophoresis of the amplified PCR products against separate control amplifications of the inserts from plasmids pBTM117c-SIM1 and pGAD427-ARNT as size markers (FIG. 14).

PCR of the individual inserts from individual plasmids carried by clone 06L22 was conducted as above except by using only the respective primer pair for the required plasmid. The individual inserts were also amplified directly from the yeast culture using a Whole Cell Yeast PCR Kit (Bio 101, USA). The pairs of inserts isolated from clone 06L22 either by amplification from the extracted plasmid DNA or by direct PCR of the yeast clone were subjected to DNA sequencing by standard protocols.

The 1.26 Kb inserts amplified using the primers specific to plasmid pBTM117 were confirmed as the expected fragment of the SIM1 gene by comparison of the known sequence for this gene (Probst et al., 1997). Likewise, the 1.37 Kb inserts amplified using the primers specific to the pGAD427 plasmid were confirmed as the expected fragment of the ARNT gene.

Example 6

Detection and Identification of Interacting Proteins Using a Large-Scale and Automated Application of the Improved 2-Hybrid System A scheme utilizing the method of the invention within a large-scale and automated approach for the parallel detection of clones that express interacting fusion proteins and the identification of members comprising the interactions is shown in FIG. 6. Yeast clones from an 'interaction library' that express interacting proteins are identified on a large-scale by the use of visual inspection or digital image processing and analysis of high-density gridded membranes on which their β-galactosidase activity has been assayed after growth on various selective media. Automated methods as described in earlier examples are used to effect the production of the interaction library and high-density spotted membranes, and the analysis of digital images of the β-gal assay and hybridisation images.

6.1 Generation of an Interaction Library for a Higher Eukaryote

A random-primed and size selected (1–1.5 Kb) cDNA library of 40-hour post fertilisation Sea Urchin embryos (*Strongylocentrotus purpuratus*) cloned into the Not 1/Sal 1 sites of pSport1 by standard procedures (Life Technologies, USA) was obtained as a gift from A.Poustka 100 ng of this library, representing, the estimated 6000 different transcripts expressed at this developmental stage (Davidson, 1986), was transformed into electro-competent *E. coli* cells by standard electroporation techniques. Recombinant clones were selected by plating the transformation mixture on 2×YT/100 μg/ml amplicillin contained in 24×24 cm agar-trays (Genetix, UK). After growth for 18 hours at 37° C., the resulting recombinant colonies (estimated to be 20,000 per tray) were washed from the 5 trays using 50 ml of LB liquid media for each tray. The amplified cDNA library cloned into pSport was isolated from this wash mixture by a QiaPrep (Qiagen, Germany) plasmid extraction procedure. Approximately 1 μg of the library inserts were then isolated from the plasmid DNA by Not 1/Sal 1 digestion and size selected (1–1.5 Kb) by agarose gel purification using standard procedures.

Two pools representing all three reading frames of the two vector series pGAD428 and pBTM118 were prepared by Not 1/Sal 1 digestion and pooling of 1 μg each of vectors pGAD428 a, b & c and pBTM118 a, b & c respectively. The insert mixture that was isolated as above was split into two equal fractions and 300 ng was ligated with 50 ng of each prepared vector-series pool. Following ligation, each reaction was then separately transformed into electro-competent *E. coli* cells, and recombinant clones for each library were selected on five 24×24 cm plates using kanamycin or ampicillin for the pGAD428 or pBTM118 libraries respectively. Approximately 500 μg of the pBTM118 and 500 μg of the pGAD428 libraries was extracted from the two sets of *E. coli* transformants by washing off the plated cells and a subsequent QiaPrep plasmid extraction of the wash mixture as described above.

To generate the interaction library, molar-equivalent amounts of the DNA binding and activation domain libraries were pooled, and 20 μg of this mixture was co-transformed into the yeast strain L40 cc by the method of Gietz et al. (1992). The resulting transformation mix was plated on a single 24×24 cm agar tray. The agar-trays were prepared as described in section 1.3.1. A total of twenty transformations were prepared and plated onto separate agar trays yielding an average of 1500 yeast colonies per tray after 7 days of incubation at 30° C.

6.2 Creation of a Regular Grid-Pattern of an Interaction Library in Microtiter Plates To create a regular grid-pattern of the interaction library, the agar-trays containing yeast colonies were placed in the modified laboratory picking robot and individual clones were automatically picked as described in section 3.1. A total of 30 384-well microtiter plates were generated and represented an interaction library of greater than 10,000 clones for the study organism. After growth of yeast clones in the wells of the microtiter plate, the library was replicated to generate 3 further copies, labelled and all copies were stored at −70° C. to provide for analysis at a later date as described in section 3.1.

6.3 Creation of a Regular Grid-Pattern of an Interaction Library on Planar Carriers To provide for efficient analysis of the interaction library, the clones comprising it were arrayed at high density on 222×222 mm porous membranes (Hybond N+, Amersham, UK) using the method described in section 3.3. A total of twenty replica membranes, each arrayed in a '3×3 duplicate' regular grid-pattern of clones using 23 384-well microtiter plates from a thawed copy of the stored interaction library were produced. On each replica membrane, one microtiter plate was aditionally arrayed in position 24 containing 8 different control clones representing known positive, negative and false positive clones. This pattern corresponded to over 9000 yeast two-hybrid clones spotted at a density of approximately 40 clones cm$^{-2}$. To ensure the number of yeast cells on each spot was sufficient for the four membranes which were to be placed on the counterselection media plates, the robot was programmed to spot onto each spot position 5 times from a slightly different position within the wells of the microtiter plates. The robot created a data-file in which the spotting pattern produced and the barcode that had been automatically read from each microtiter plate was recorded.

Each membrane was carefully laid onto approximately 300 ml of solid agar media in 24×24 cm agar-trays. Fourteen membranes were transferred to SD-leu-trp-his media and three each of the membranes which had been spotted five times were transferred to either SD-trp+CHX or SD-leu+CAN media. The yeast colonies were allowed to grow on the surface of the membrane by incubation at 30° C. for 3 days.

Figure 15:
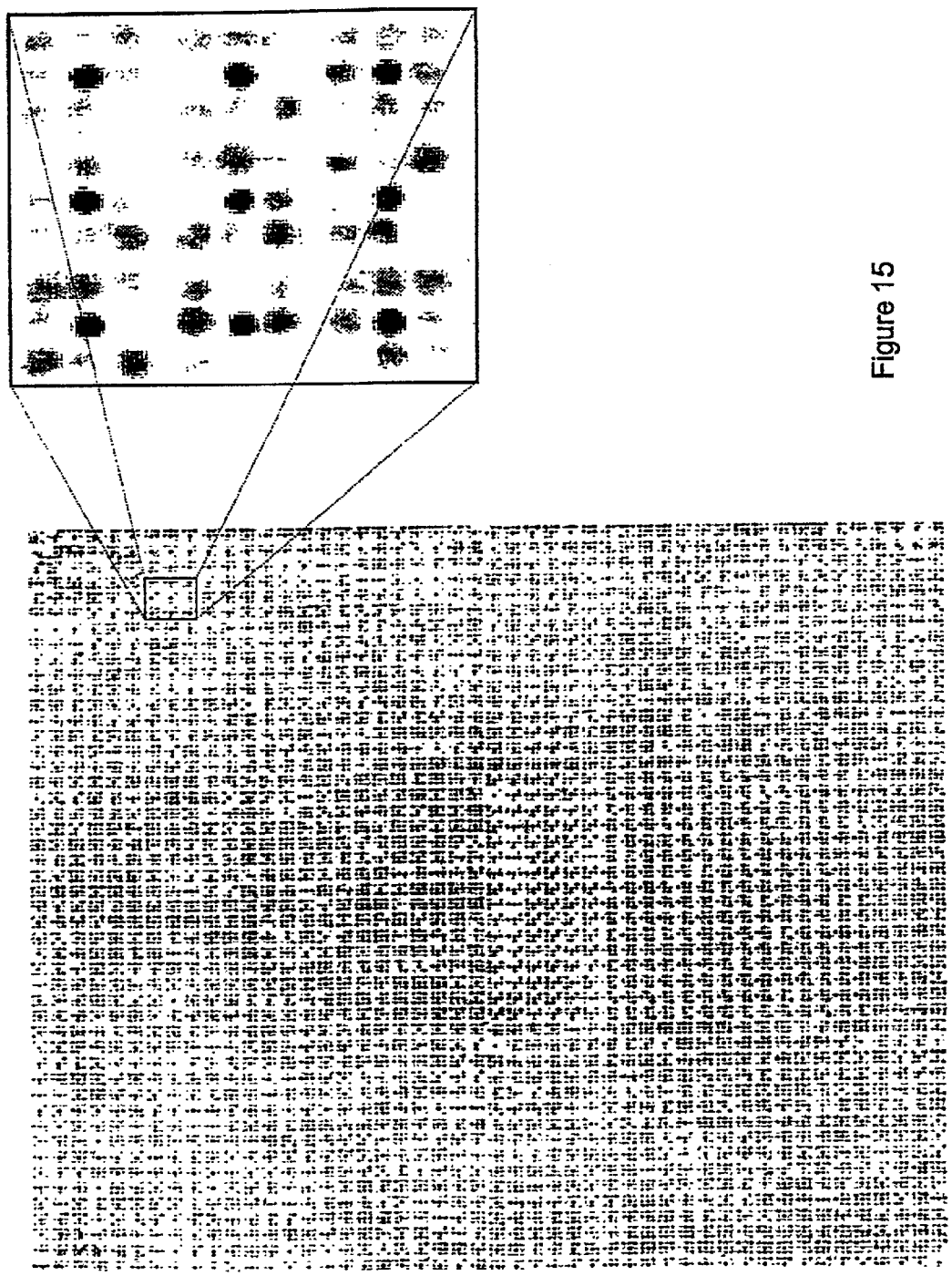

6.4 Detection of the Readout System in a Regular Grid Pattern and Analysis Using Digital Image Analysis to Identify Positive Clones To provide for the efficient identification of individual clones that expressed interacting fusion proteins, the activation state of the individual clones grown on the porous carriers was examined in a highly parallel manner. The replica arrays of the interaction library grown on the six membranes placed on the counterselective media, plus three further membranes which were placed on SD-leu-trp-his medium as described above, were assayed for lacZ activity, a digital image of each was captured and image-processed as described in section 1.4.1. FIG. 15 shows an grey-scale image of readout system activation for individual clones from the interaction library arrayed in a regular grid-pattern on a membrane filter and grown on SD-leu-trp-his medium.

The activation state of the readout system for each individual clone in the regular grid-pattern grown on the three selective media was recorded from each digital image using the image analysis system described in section 4.1. These data were collected for the interaction library grown on three replica-membranes for each of the selective media SD-leu-his, SD-leu+CAN & SD-trp+CHX, and was related together for each individual clone using the computer program shown in FIG. 12a.

This program was used to query these data and identify those clones that had activated the readout system when grown on two out of three SD-leu-trp-his replica membranes, but not when grown on any of the two sets of three replica membranes placed on the two counterselective media SD-leu+CAN or SD-trp+CHX. The data-base correctly identified the eight different control clones each arrayed in 48 wells of the 24' microtiter plate. A total of 7539 clones from the interaction library arrayed in 23 384-well microtiter plates were thus identified as positive clones— clones that only activated the readout system when both plasmids (and hence fusion proteins) were expressed in the cell. 3983 clones were identified as false-positive clones as they also activated the readout system when grown on SD-trp+CHX medium—the growth medium that eliminated the plasmid expressing the activation domain fusion protein. 113 clones were identified as false positive clones by activating the readout system when grown on SD-leu+CAN medium—the growth medium that eliminated the plasmid expressing the DNA binding fusion protein. These data were automatically made available to a table of the relational database holding information on each clone of the interaction library as described in Example 7.

This relatively high number of false-positive clones identified following SD-trp+CHX selection can be explained since on elimination of the activation domain plasmid, the DNA-binding domain fusion protein is tested for its ability to activate the readout system without any partner protein. It is known that many transcripts expressed in early Sea Urchin embryos are transcription factors, and that fragments of transcription factors can commonly cause false positives in the yeast two-hybrid system when expressed as the DNA-binding domain fusion protein. Therefore, these results demonstrate that the above method can efficiently eliminate large-numbers of false positive clones from a large-scale library vs. library screen interaction screen.

6.5 Identification of the Individual Members of the Interaction by Nucleic Acid Amplification and Sequencing A total of 96 positive clones were randomly selected from the database and recovered from a frozen copy of the interaction library clones stored in 384-well microtiter plates. The DNA sequences cloned into the pGAD428 and pBTM118 vectors carried by each clone were directly amplified as described in section 5.2 except that the direct PCR reactions were conducted in 96-well microtiter plates using a high-thoughput water-bath thermocycling machine (Maier et al., 1994).

Standard sequencing approaches were employed to characterise the nucleic acids encoding the DNA-binding domain fusion proteins of the positive clones following pBTM428-specific 96-well PCR as described above. Similarly, the sequence of the insert encoding for the activation-domain fusion protein following pGAD118-specific PCR was determined. Sequence comparison of these insets against published DNA sequences using standard sequence comparison tools (e.g. BAST), identified that one interaction involved two previously unidentified gene fragments that were expressed by the positive-clone located in plate 5, well K20. From the predicted protein sequence these two genes were designated Protein A and Protein B.

6.6 Identification of Individual Members of the Interaction by Nucleic Acid Hybridisation Regular grid patterns of the nucleic acids encoding the fusion proteins from the interaction library were constructed. The membranes which had been placed on the SD-leu-trp-his medium and had not been used to assay β-gal activity were processed according to the procedure described in Larin & Lehrach (1990) in order to affix the DNA contained within the clones of the interaction library onto the surface of the membrane. The DNA fragment that encoded Protein A isolated as above, was radioactively labelled by the method of Feinberg & Vogelstein (1983). This labelled probe was hybridised to an array with DNA from the interaction library affixed to it, and the array washed and detected as 5.1.

The number and identity of hybridisation-positive clones was determined for each hybridisation using the automated image analysis system described in Lehrach et al., (1997). Seven clones from the interaction library were identified as hybridisation-positive for the probe encoding Protein A.

Figure 16:
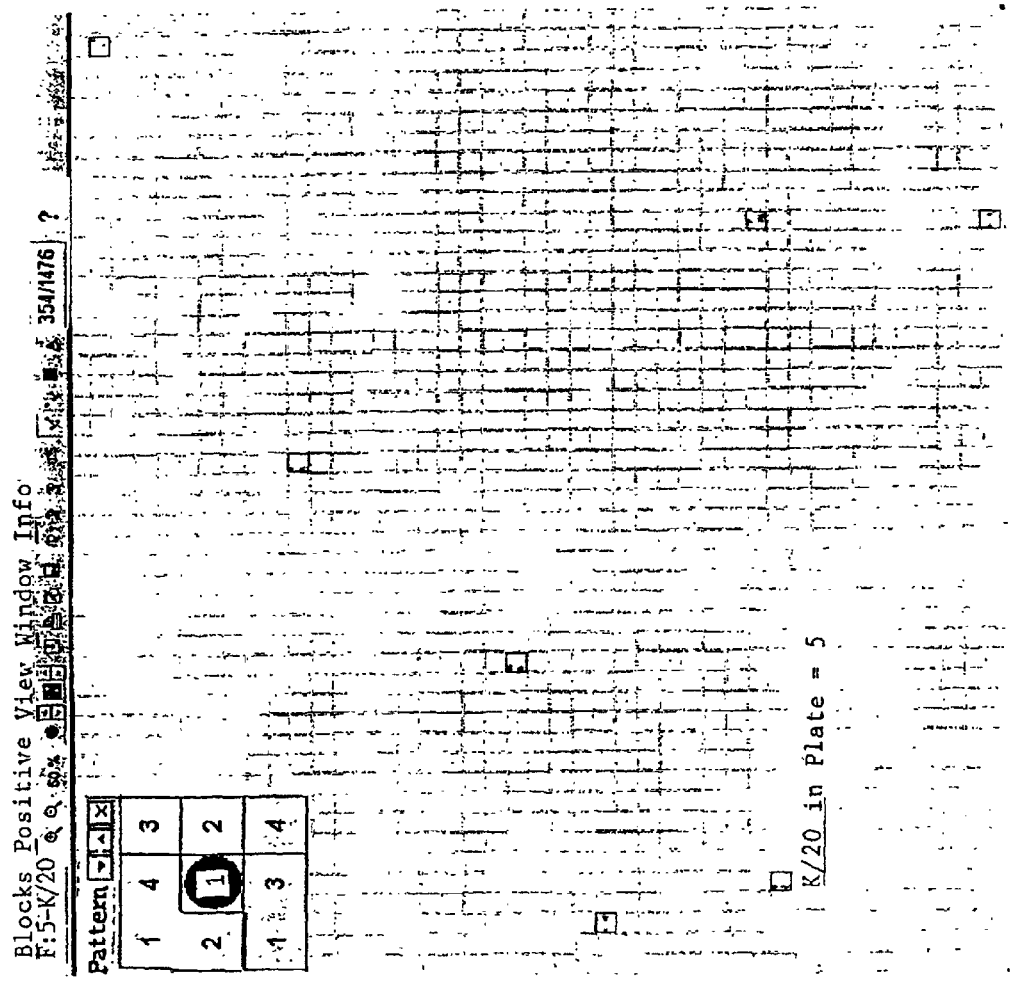
Figure 17:
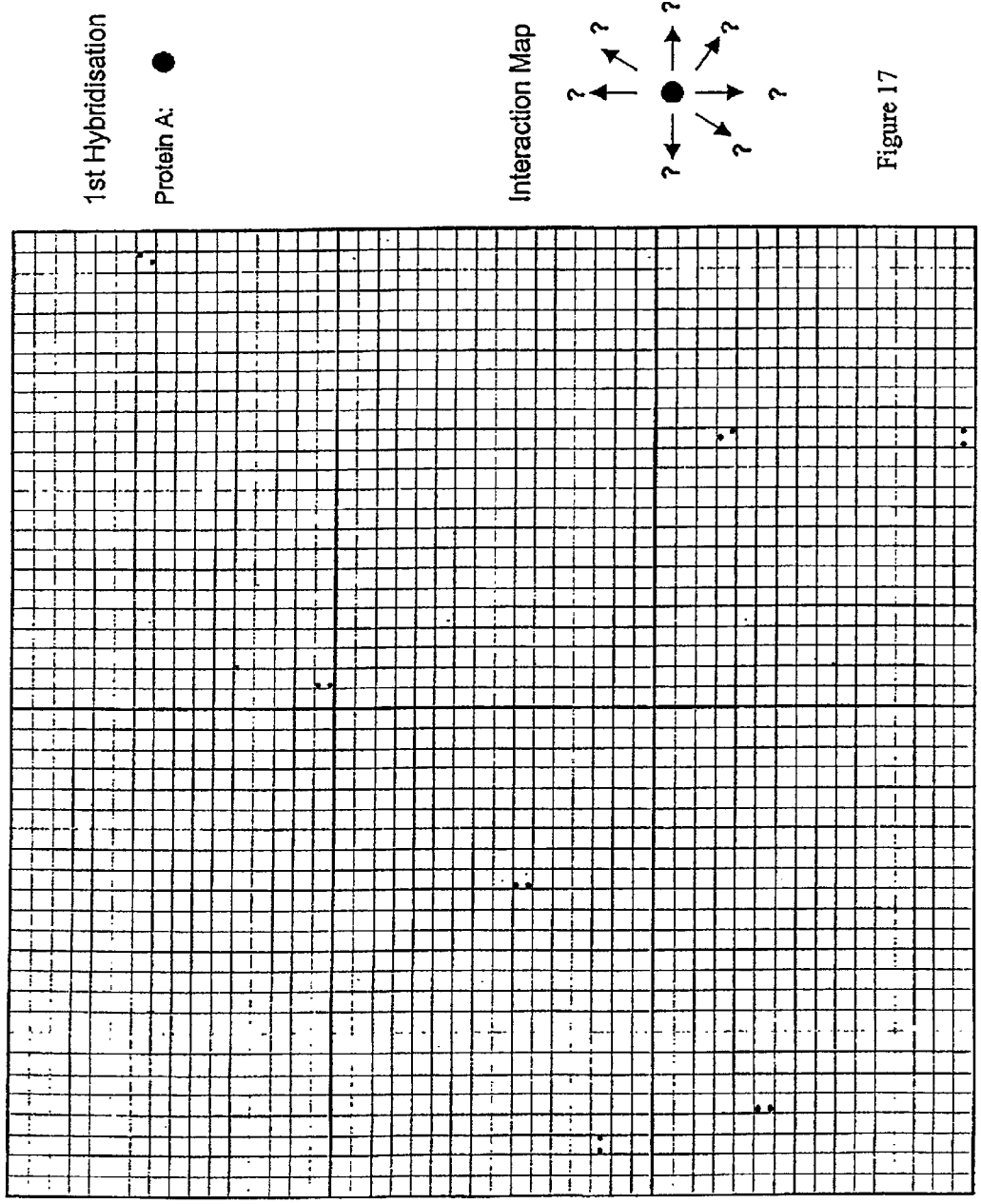

FIG. 16 shows a digital image of a DNA array hybridised with the gene fragment encoding Protein A with the hybridisation-positive clones identified and marked by the automated image analysis system, and FIG. 17 represents a graphical representation of the positives found by this analysis. The database described in Example 7 was used to refer to the list of clones generated by the image analysis program and identify those hybridisation-positive clones that were interaction-positive clones and hence eliminate any false positive clones from further analysis. As expected, a hybridisation-positive clone was the clone 5K20 from which the probe corresponding to Protein A was obtained.

Figure 18:
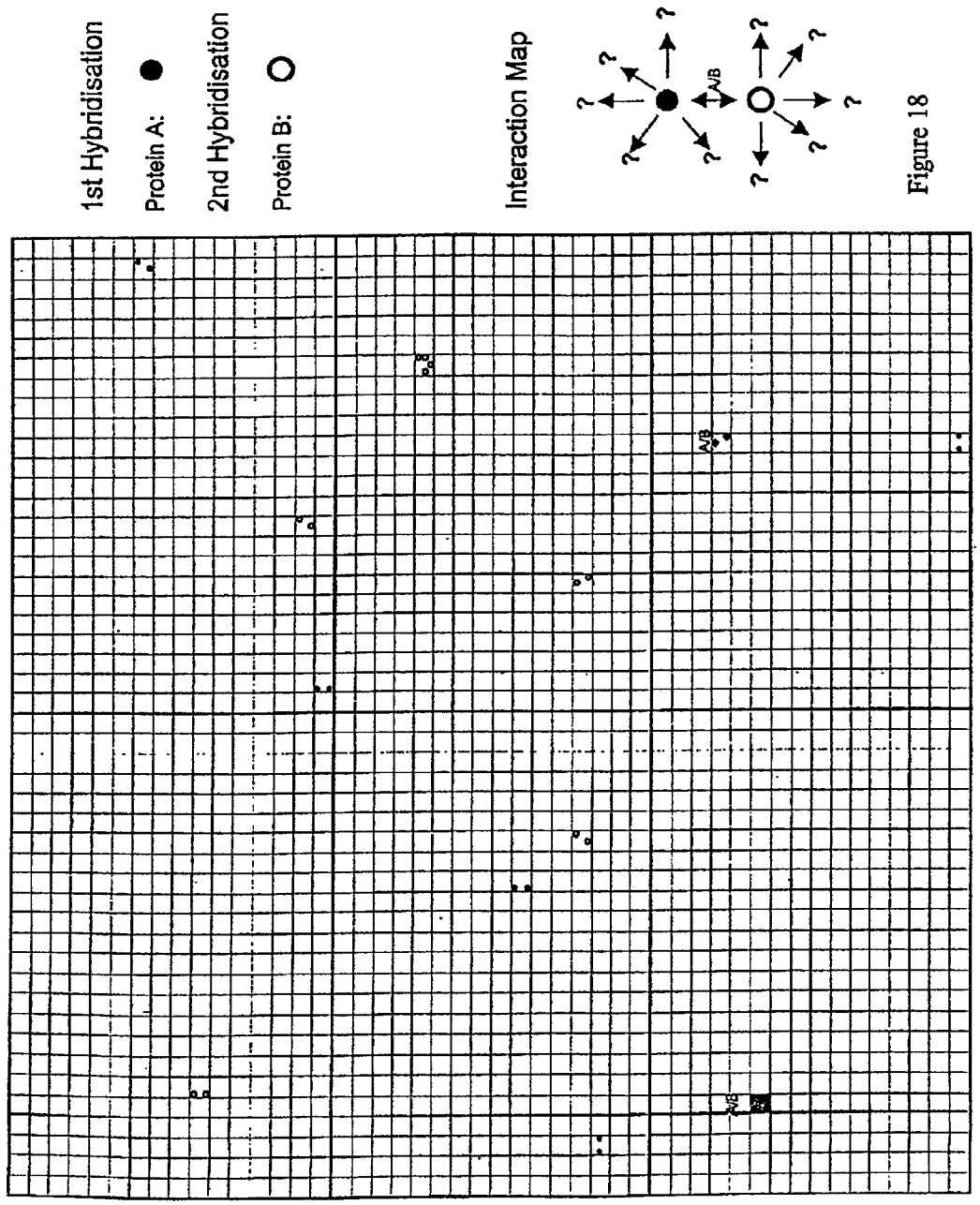

To extend the interaction pathway from Protein A, a second filter was hybridised with a radioactive labelled probe generated from the fragment coding for Protein B. Analysis of the hybridisation signals with the database described in Example 7 resulted in the identification of eight interaction-positive clones that carried the gene fragment encoding for Protein B. FIG. 18 shows a graphical representation of the hybridisation-positive and interaction-positive clones identified with probe B (open circles) and probe A (red circles). Two clones (5K20 and 3L 11 marked by "A/B") gave a hybridisation signal with both probe A and Probe B, indicating that both these positive clones expressed the same interacting fusion proteins.

To further extend the interaction pathways of proteins A and B, the DNA binding and activation domain plasmids were extracted from one interaction-positive clone that gave a hybridisation signal only with probe B (clone 6D18). DNA sequencing of the inserts carried by these genetic elements confirmed the presence of a gene fragment encoding for Protein B in the DNA binding domain plasmid. Sequence analysis showed that the activation domain plasmid carried a fragment for another unknown gene coding for Protein C.

Figure 19:
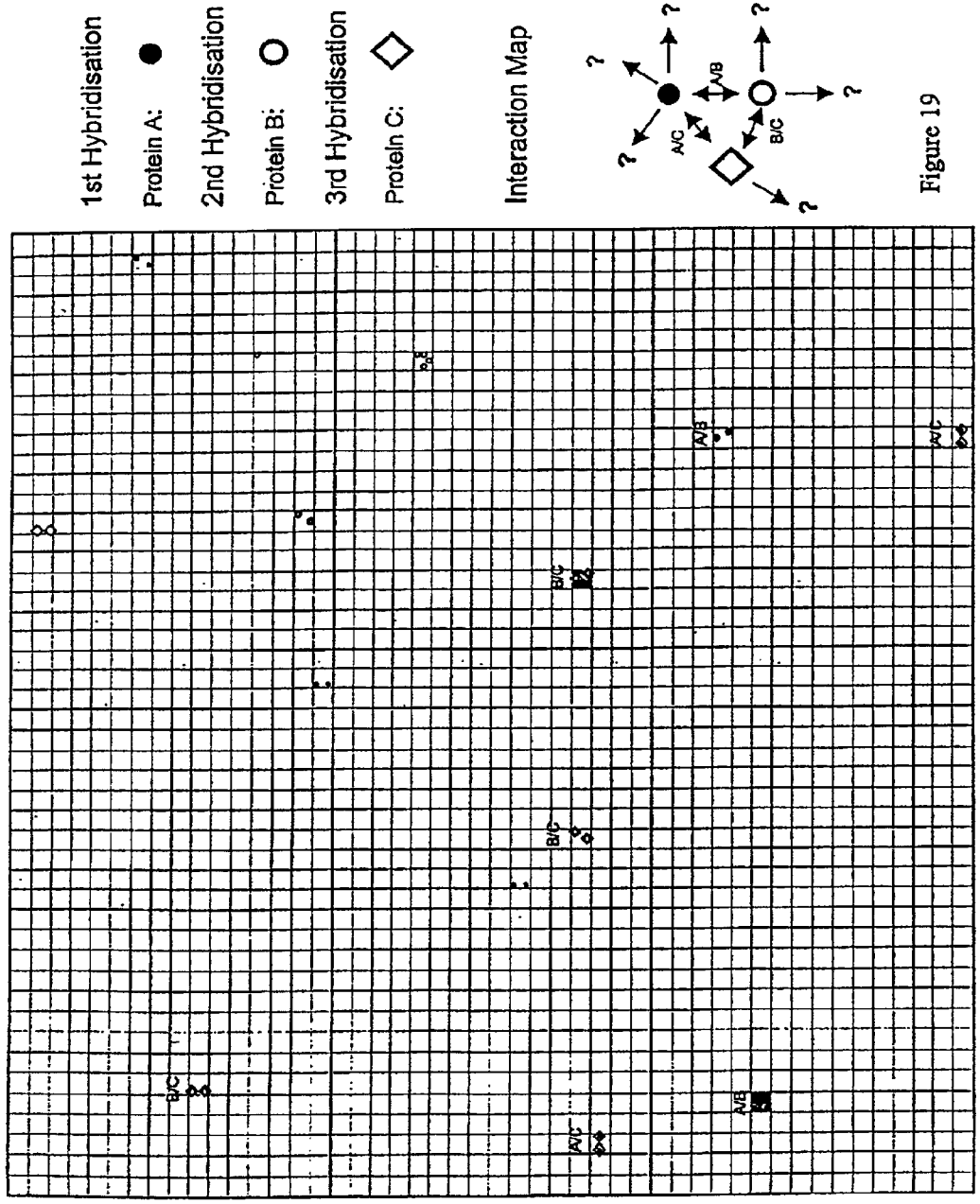

This gene fragment was used as a probe to another array and the data analysed as above. FIG. 19 shows the results of this hybridisation (marked with diamonds), together with that from the previous two hybridisations. A total of six interaction-positive clones were identified as carrying genetic elements encoding for Protein C. Three of these interaction-positive clones were previously shown to hybridise with probe B (4G19; 1D7; 6D18) and two clones to hybridise with probe A (1C22; 3A11). A graphical view of the interactions identified by these three simple hybridisations is outlined in FIG. 19. Question marks represent possible further steps in the network which could be further investigated by a similar investigation of the genetic elements carried by the remaining hybridisation-positive clones for probes A, B or C. Indeed, by following this focused hybridisation approach, 14 different protein—protein interactions were identified by a total of nine hybridisations and subsequent sequencing of the inserts encoding the interacting members. All these data were entered into the data-base described in Example 7.

6.7 Automated Rearraying of Positive Clones

The 3443 positive clones identified as described above were distributed across all 23 microtiter plates of the interaction library. To greatly facilitate further analysis of positive clones, it was advantageous to individually physically isolate clones and to generate a second, re-arrayed regular grid-pattern of positive clones, preferably within a further set of 384-well plates.

Existing rearraying robots such as described by Stanton et al, (1996), Lehrach et al., (1997) or those sold by commercial sources (Genetix, UK) system failed to provide a satisfactory inoculate when transferring yeast cells from individual wells of a source ('mother') 384-well plate containing the original interaction library in wells of a new, sterile 384-well destination ('daughter') plate containing growth medium. Therefore, the existing transfer pins were replaced by straight 2 mm diameter pins that terminated in a flat end. Secondly, the inoculation procedure was modified to maximise the amount of dried cell material carried on the pin that was transferred into the new well within the daughter plate as described for automated picking of yeast colonies in section 3.1. The pins were sterilised between rearraying cycles by a 0.3% hydrogen peroxide wash-bath, 70% ethanol wash-bath and heat-drying procedure as described in section 3.1.

The list of positive clones, together with their plate-well location was generated from the data-base described in Example 7 and automatically loaded as a computer file onto the rearraying robot. The robot automatically took the mother plate containing the first positive yeast two-hybrid clone by reference to the data file and read and recorded the barcode of the plate. Individual and sequential pins of the 96-pin rearraying head were positioned above and lowered into the required wells from this first plate, and the mother plate was automatically exchanged when all positive clones had been sampled. When all 96-pins had been used to collect inoculates of positive clones, the head was automatically moved over to the first 384-well daughter plate containing SD-leu-trp/7% glycerol and inoculated all 96-pins in the first set of wells as described above. A data output file was then updated which related the new plate-well location of a given positive clone in the re-arrayed library to its old plate-well location in the original interaction library. All pins were then sterilised as described, and the cycle completed until all positives clones had been transferred from the interaction library to a new plate-well location comprising the re-arrayed library. The data output file was then transferred to the central computer database to append a table in the data-base described in Example 7 to record the correct location of a given positive clone in the re-arrayed interaction library. The resulting clones in the daughter plates were replicated into two further copies and stored at −70° C. as described in section 3.1.

Example 7

Generation of a Data-Base of Interactions

Central to the scheme (FIG. 2) is a data-table holding relevant information on each member of an interaction—the cDNA-Table—where a separate record in the table represents each member of an interaction, and members are indicated to form interactions by sharing the same clone name. It is advantageous to structure the core data-table in this way for several reasons. First, the same core table can be used to hold data on cDNAs from different kinds of genetic libraries (for example, standard cDNA or genomic libraries) which can be generated during a global analysis using various genomic techniques, not just interaction data Secondly, each of the members of an interaction, or genetic fragments may be further characterised by a number of ways for different sets of data. Of direct relevance to protein—protein interaction for a given genetic fragment in the cDNA_Table is first, the Gene_Table, which provides a direct relationship to the fragment's DNA sequence, nucleotide homology match (for example through BLAST searching) and the corresponding gene name. Second, the Domain_Table provides facility to directly access data of the fragment's in-frame translation, amino acid homology match (for example through BLASTN searching) and any 2 or 3-dimensional structural information which may be known or can be predicted. As is commonly known in molecular biology, there are many ways in which a given genetic fragment may be characterised, and this data-base structure provides the facility to relate from the central cDNA_Table to any other table holding data describing said characterisation as may be appropriate. For example, those holding data on genetic, expression, target validation, protein biochemistry or library construction information. Of particular relevance to the method of invention, is the relationship of a given cDNA fragment to a table holding information on oligofingerpriting data Said oligofingerpriting data can be used to identify each member of an interaction in a highly parallel manner and includes fields for data such as cluster number, confidence of cluster membership and predicted gene homology for that cluster (Maire et al., 1994). Third, such a data-base structure will more easily enable tertiary or higher order interactions to be incorporated within the same data table. This is in contrast to a structure in which interactions rather than members of an interaction were the basic object or record in a data table, and for each higher order interaction a new data-table would be needed or an existing data-table modified.

In the case of a yeast two-hybrid interaction screen one related table would be the Y2H_Table. Said table may include information for a given clone pertaining to cloning and experimental details of its creation, the tissue and library from which it was derived, its physical location to enable easy access for further studies, whether it was derived from the mating of given Mata and Matα strains. Importantly, the Y2H_Table holds information pertaining to the interaction class of the clone—where said interaction class is defined as whether the clone was a positive clone, negative clone, or a false positive with respect to either the activation domain (AD) or biding domain (BD) fusion protein. The value for said interaction class is easily derived for a large number of clones by the method of invention described in earlier examples.

To assist any focused approach to identifying members comprising the interactions, the Hyb Table is provided. This table relates for a given clone, the hybridisation intensity obtained with a given probe in a hybridisation experiment using a given high-density array. Said high-density array to he related to tables holding data from the spotting robot such as the defined spotting pattern used, the method by which the array was produced and the identity of the library and clones arrayed on said array. The incorporation of these tables within a user interface will enable this embodiment of the method of invention to be easily conducted by displaying to the user the physical location of a given positive yeast two hybrid clone that hybridised to a given probe. Said two-hybrid clone can then be recovered, the members comprising the interaction isolated by PCR and sequenced. Said sequenced members of an interaction then provide data to be entered into the cDNA_Table and other related tables on further analysis. Said member to then be used as a second hybridisation probe onto an array to identify the next step in an interacting pathway by the same procedure.

On collection of a substantial number of interacting members within the cDNA_Table, these data can be curated by manual and/or expert systems to update a definitive data table for example the PathCode_Table. Said definitive database to hold the highest quality information on interactions from the cDNA_Table, where said highest quality information on interactions to be those from the cDNA Table that pass a level of 'certainty' as specified to the curator and/or expert system. To assist in the decision-making process, all relevant data especially that of the translated frame of the cDNA and corresponding protein domain is related from other tables and presented in a usable form to the curator and/or expert system. This presentation allows for easy recognition and exclusion or correction of basic errors in the data such as poor quality sequencing, or incorrectly cloned cDNA fragments. These may include contaminating fragments which can be identified as originating from an organism which is different to that of the cDNA library.

A given cDNA is entered into the PathCode_Table only once for each interaction in which it is found, together with a record for the corresponding interacting cDNA (or cDNAs for multimer complexes). However, where a cDNA has different interactions, for example with different proteins or where different protein domains of the cDNA interacts with different proteins, then in each case a different record for the cDNA is created. These different records are linked by a common and unique 'Interaction ID'. A given interaction is represented thus only once in the PathCode_Table, and is related to previous tables in the data-base by the host-cell clone that represents the interaction and the ID of each cDNA in the interaction. Said host-cell that represents the interaction is selected by consideration and curation of all host-cells and the interacting fragments representing said interaction held in the cDNA_Table.

A set of criteria can be implemented to assist in said curation and selection, and to derive a measure of confidence for the interaction. As way of example, such criteria may have decreasing information value and include: First, if a given interaction is observed in both directions of the experiment ie proteinA-AD interacting with proteinB-BD, and proteinB-BD interacting with proteinA-DB. Second, if different examples of the same interaction are observed. Where different examples of the same interaction are defined as protein fragments of substantially different length and position (for example greater than 10% different) but from the same underlying protein domain and are also found to interact Third, if the same examples of the same interaction are observed, for example by multiple cloning of the same fragments where the same fragments are of substantially the same length and position from the same underlying protein domain. Fourth, that the protein domains that interact may have biological relevance. That is, similar domains or genes are known to interact from public literature, or it is known that both genes are expressed or likely to be expressed in the same cellular location. This criterion can also be used as an internal quality control of the library cloning, interaction experiment and subsequent identification of interacting members since every interaction experiment should identify a certain set of published 'house-keeping interactions', and the identification of such interactions can be used as quality measure for the overall interaction experiment One criterion of particular importance, is the optional validation of a given interaction by secondary experiments. For example, cDNA fragments representing the interacting proteins may be subcloned, and additional interaction experiments be conducted. Said additional interaction experiments may include testing each protein for interaction against a set of unrelated proteins to investigate the specificity of said interaction. Said testing may be conducted using the same interaction method that identified the interaction, for example the yeast two-hybrid, but preferable it is an independent method. Favoured, is where a given interaction is biochemically validated using methods including tissue co-northern, cellular co-localisation or co-precipitation studies.

All these criteria are considered by the curator and/or expert system to assist in the decision on which cDNA fragments and their interactions are entered into the PathCode_Table. Other interactions known or published in scientific literature may also be entered into this data-base during the curation procedure, and hence a field in the table represents the source of this interaction being internal or an external reference. The PathCode table has relational links to secondary or external data-bases holding data on nucleotide and protein sequences, and biochemical, structural, biological or bibliographical information. These data, representing the complete relationships between all tables and data-bases can be queried by using simple user interfaces, designed for example using Java, or by more complicated commands such as those provided by SQL. Possible queries include those to locate from these data interactions, pathways or networks for a given nucleotide or amino acid sequence or motif, or for a given 3-dimensional structure or motif. Secondly, for highly established networks, these data may be queried to identify a given pathway between two given points. It may be that some queries are more efficiently conducted using a substantially different design of the PathCode_Table—for example by representing a given interaction as the underlying record rather than a given member of an interaction. A person skilled in the art would be able to transfer data from one table design to another using standard data-parsing systems to enable said more efficient conduction of queries.

The result of these queries is displayed using graphical methods to enable the investigator to interpret these data most efficiently. Said graphical methods to include elements activated by mouse clicks such as hotlinks to seamlessly link these data with other data sources, or to query and display further levels of interactions. Computer-based methods of generating visual representations of specific interactions, partial or complete protein—protein interaction networks can be employed to automatically calculate and display the required interactions most efficiently. Both finding the network paths and calculating the optimal display of the found paths can be based on algorithms well known in the art of mathematical graph theory. For example, algorithms similar to those which have been employed to display other biological relationships such as genetic pedigrees and phylogenetic relationships.

An established computer data-base of protein interactions has many useful applications. For example, it may be used to predict the existence of new biological interactions or pathways, or to determine links between biological networks. Furthermore with this method, the function and localisation of previously unknown proteins can be predicted by determining their interaction partners. It also can be used to predict the response of a cell to changes in the expression of particular members of the networks without making a molecular, cellular or animal experiment Finally, these data can be used to identify proteins or interactions between proteins within a medically relevant pathway, which are suitable for therapeutic intervention, diagnosis or the treatment of a disease.

Example 8

Preselection Against False Positive Clones and the Automated Creation of a Regular Grid-Pattern of Yeast Cells Expressing a Fusion Protein 8.1 Genetic Pre-Selection of False Positive Clones Three mating type-a yeast strains were constructed by co-transformation using the method of Schiestel & Gietz (1989) into L40 ccu, of the plasmid pLUA containing the URA3 readout system, and either the pBTM117c, pBTM117c-SIM1 or pBTM117c-HIP1 plasmids respectively. Transformants that contained both the pLUA plasmid and one of the DNA binding domain plasmid were selected on SD-trp-ade medium. Three mating type-α yeast strains were similarly constructed by cotransformation into L40ccuα of pLUA, and either the pGAD427, pGAD427-ARNT or pGAD427-LexA plasmids respectively. Transformants that contained both the pLUA and one of the activation domain plasmids were selected on SD-leu-ade medium. The yeast strains thus obtained are listed in Table 3.

The yeast strains x1a, x2a and x3a were replica plated onto the selective media SD-trp-ade, SD-trp-ade containing 0.2% 5-FOA and SD-trp-ade-ura, while the yeast strains y1α, y2α and y3α were replica plated onto the selective media SD-leu-ade, SD-leu-ade containing 0.2% 5-FOA and SD-leu-ade-ura. Table 4 shows that the two yeast strains x3a and y3α which expressed the fusion proteins LexA-HIP1 and GAL4ad-LexA respectively were unable to grow on their respective media containing 5-FOA yet were able to grow on their respective media lacking uracil. In contrast, all other yeast strains that contained plasmids that expressed fusion proteins that were alone unable to activate the readout system could grow on their respective media containing 5-FOA, but could not grow on selective media lacking uracil. This indicates that it is possible to eliminate yeast clones that express single fusion proteins which auto-activate the readout system, by selection on media containing 5-FOA. Thus, the URA3 readout system successfully eliminated clones containing auto-activating fusion proteins prior to interaction mating.

8.2 Creation of a Regular Grid Pattern of Genetically Pre-Selected Yeast Cells Expressing a Fusion Protein Two defined libraries of clones that express fusion proteins were created. First, the yeast strain L40 ccu was transformed with the plasmid pLUA and a resulting stable transformant colony cultured in minimal medium lacking adenine. Cells from this culture were rendered competent and transformed with 3 μg pooled mixture of all six pBTM117c constructs shown in Table 2. Second, the yeast strain L40 ccuα was transformed with the plasmid pLUA and a resulting stable transformant colony cultured in minimal medium lacking adenine. Cells from this culture were rendered competent and transformed with 3 μg pooled mixture of all six pGAD427 constructs shown in Table 2. In all cases, competent cells were prepared and transformations conducted using the method of Schiestel & Gietz (1989).

The two transformation mixes were incubated at 30° C. for 2 hours in 10 ml of YPD liquid medium before plating onto large 24×24 cm agar trays (Genetix, UK). The Mata cells containing the pBTM117c fusion library were plated onto minimal medium lacking tryptophan and adenine but containing 0.2% 5-FOA (SD-trp-ade+FOA), while the Matα cells containing the pGAD427 fusion library were plated onto minimal medium lacking leucine and adenine but containing 0.2% 5-FOA (SD-leu-ade+FOA). The agar trays were poured using an agar-autoclave and pump (Integra, Switzerland) to minimise tray-to-tray variation in agar colour and depth. After plating, the colonies were grown by incubating the trays at 30° C. for 4 to 7 days resulting in approximately 1500 colonies per tray.

Mata clones containing the plasmid pBTM117c-HIP1 and Matα strains containing the plasmid pGAD427-LexA expressed the fusion proteins LexA-HIP1 and GAL4ad-Lexa respectively. These fusion proteins were shown to activate the URA3 readout system without any interacting fusion protein. Therefore, cells carrying these plasmids should be unable to grow on selective media containing 5-FOA. Hence, only those yeast clones expressing a single fusion protein unable to activate the URA3 reporter gene will form colonies on be picked by the modified robotic system.

Using the modified laboratory picking robot, individual yeast colonies were automatically picked from the agar-trays into individual wells of a sterile 384-well microtiter plates, as described in section 1.3.1 except that the Mata yeast strains were picked into microtiter plates containing the growth medium SD-trp-ade and 7% (v/v) glycerol, while the Matα yeast strains were picked into microtiter plates containing the growth medium SD-leu-ade and 70/o (v/v) glycerol. The resulting microtiter plates were incubated at 30° C. for 4 days with a cell-dispersal step after 36 hours section 3.1. After incubation, each plate was replicated to create two additional copies into labelled 384-well microtiter plates and pre-filled with the liquid growth medium containing 7% glycerol as was appropriate for the yeast strain. The replicated plates were incubated at 30° C. for 4 days with a cell dispersion step conducted after 36 hours as above, subsequently frozen and stored at −70° C. together with the original picked microtiter plates of the libraries of cells expressing fusion proteins.

It will be clear that higher density regular grid-patterns of such an interaction library can be easily generated by a person skilled in the art from these microtiter plates of diploid yeast cells by following the methods disclosed in sections 3.2, 3.3 and 3.4 of this invention.

8.3 Visual Differentiation Against False Positives for an Improved Yeast Two-Hybrid System Six yeast strains were generated by transforming each of the pBTM117c plasmid constructs described in Table 2 into L40 ccu by the method of Schiestel & Gietz (1989). Each strain was plated on selective growth medium lacking tryptophan, buffered to pH 7.0 with potassium phosphate and containing 2 ug/ml of the β-galactosidase substrate X-Gal (SD trp/XGAL). Six further strains were similarly constructed by transforming each of the pGAD427 plasmid constructs described in Table 2 into L40 ccuα. These strains were plated on selective growth medium lacking leucine, buffered to pH 7.0 with potassium phosphate and containing 2 ug/ml of X-Gal (SD-leu/XGAL). After incubation at 30° C. for 7 days, the strains were inspected for growth and blue colour. Table 5 shows that although all yeast strains were able to grow on the selective media, only the L40 ccu strain expressing the fusion protein LexA-HIP1 and the L40 ccuα strain expressing the fusion protein GAL4ad-LexA turned blue. In contrast, all other yeast strains that contained plasmids that expressed fusion proteins unable to activate the readout system alone could grow on the selective media, but did not turn blue. It was found that for the fusion proteins described here, the blue-colour generated by auto-activation of the β-galactosidase readout system developed faster than any pink-colour of other clones due to the ade2 mutation. However, the blue colour may develop slower than the pink colour for some fusion proteins that may affect the reliability of visual differentiation using automated systems with grey-scale vision systems. Therefore, a person skilled in the art will be able to incorporate colour recognition systems, colour filters or construct a yeast strain that does not develop the pink colour. For example, using a strain carrying the wild-type ADE2 gene, or the complementary mutation ade3.

8.4 Using Automation to Visually Discriminate False-Positive Yeast Clones and the Creation of a Regular Grid Pattern of Cells Two defined fusion protein libraries were generated. Six pBTM117c constructs shown in Table 2 were pooled and 3 μg of the mixture was co-transformed into the yeast strain L40 ccu. The resulting transformants were selected by plating the mixture onto five large 24×24 cm agar-tray (Genetix, UK) containing minimal medium lacking tryptophan, buffered to pH 7.0 with potassium phosphate and containing 2 ug/ml of X-Gal (SD-trp/XGAL). Second, the six pGAD427 constructs shown in Table 5 were pooled and 3 μg of the mixture was co-transformed into the yeast strain L40 ccuα. The resulting transformants were selected by plating the mixture onto five large 24×24 cm agar-tray (Genetix, UK) containing minimal medium lacking leucine, buffered to pH 7.0 with potassium phosphate and containing 2 ug/ml of X-Gal (SD-leu/XGAL). These agar-trays were poured using an agar-autoclave and pump (Integra, Switzerland) to minimise tray-to-tray variation in agar colour and depth. The agar-trays were incubated for 7 days to allow the yeast clones to grow and the blue colour of clones able to activate the β-galactosidase reporter gene to develop. In all cases, competent cells were prepared and transformations conducted using the method of Schiestel & Gietz (1989).

Using the modified laboratory picking robot, individual yeast colonies were automatically picked from the agar-trays into individual wells of a sterile 384-well microtiter plates, as described in section 3.1 except that the Mata yeast strains were picked into microtiter plates containing the growth medium SD-trp and 7% (v/v) glycerol, while the Matα yeast strains were picked into microtiter plates containing the growth medium SD-leu and 7% (v/v) glycerol.

Figure 20:
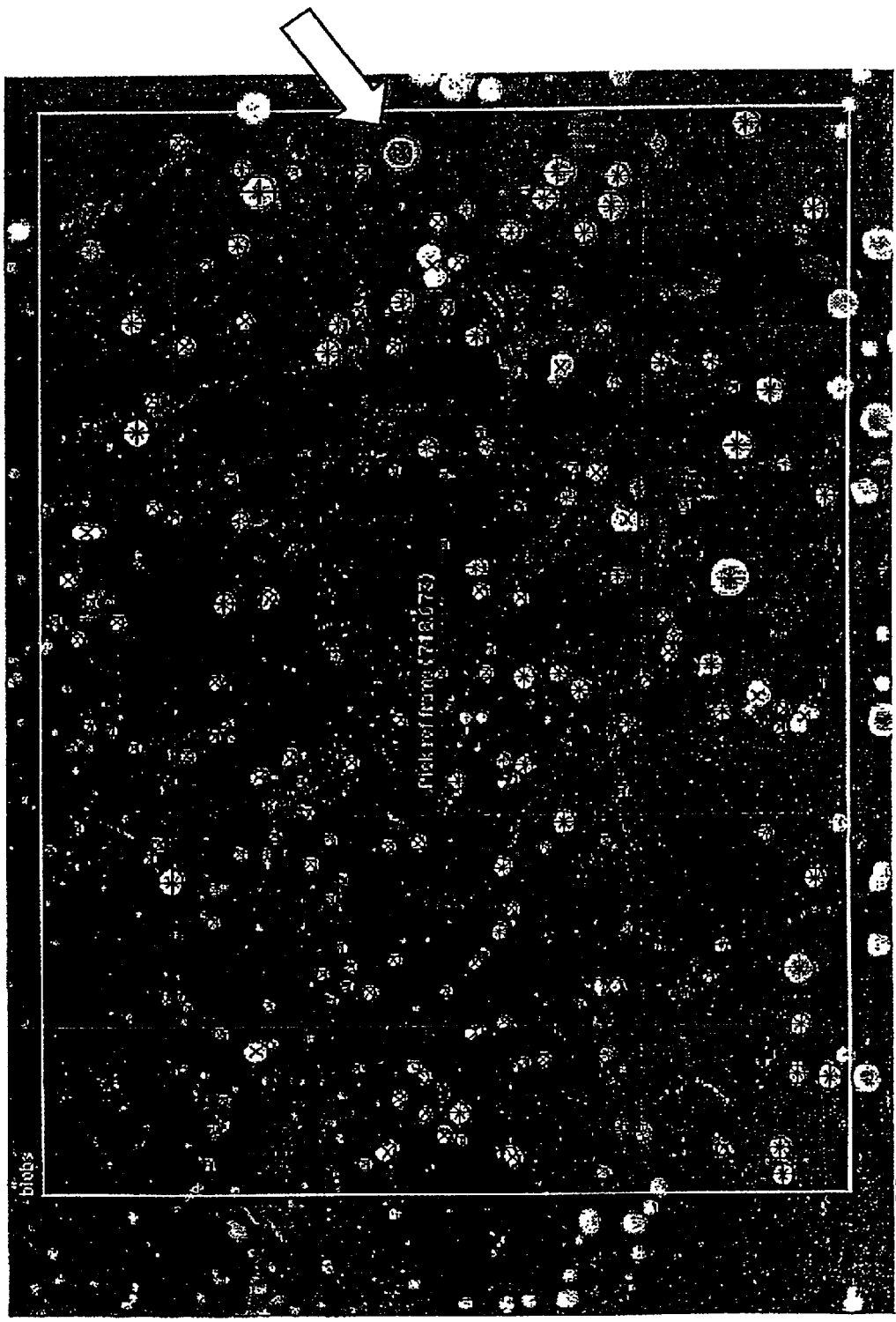

Automated visual differentiation was made by using the blue-white sorting parameters described in section 3.1. The robot was programmed to pick only white colonies into microtiter plates and ignore all colonies that had turned blue on activation of the β-galactosidase reporter gene. FIG. 20 displays automated visual discrimination of false positive clones using the modified picking system described above. The resulting microtiter plates were incubated at 30C for 4 days with a cell-dispersal step after 36 hours section 3.1. After incubation, each plate was replicated to create two additional copies into labelled 384-well microtiter plates and pre-filled with the liquid growth medium containing 7% glycerol as was appropriate for the yeast strain. The replicated plates were incubated at 30° C. for 4 days with a cell dispersion step conducted after 36 hours as above, subsequently frozen and stored at −70° C. together with the original picked microtiter plates of the libraries of cells expressing fusion proteins.

It will be clear that higher density regular grid-patterns of such an interaction library can be easily generated by a person skilled in the art from these microtiter plates of diploid yeast cells by following the methods disclosed in sections 3.2, 3.3 and 3.4 of this invention.

Only those colonies that expressed the fusion protein LexA-HIP1 or the GAL4ad-LexA should be able to activate the LacZ gene and hence turn blue when grown on the selective medium. Therefore, blue colonies from the Matα library would be expected to carry the pBTM117c-HIP1 construct while white colonies would carry other pBTM117c plasmid constructs. Likewise, blue colonies from the Matα library would be expected to carry the pGAD427-LexA construct while white colonies would carry other pGAD427 plasmid constructs. To prove this hypothesis, 10 white and 10 blue colonies were randomly selected from a picked agar-tray of the Mata library, and twenty colonies from a 384-well microtiter plate that had been automatically picked from this plate. All 40 colonies were hand inoculated into individual 1 ml liquid cultures of SD-trp medium and the cultures grown for 3 days at 30° C. The inset carried by each clone was checked by direct PCR amplification of the pBTM117c insert from the yeast culture and DNA sequencing by standard protocols. All ten yeast colonies that had activated the readout system and turned blue carried the 1.2 Kb HIP1 fragment, while the white colonies carried the 1.6 Kb HD1.6, the 1.1 Kb SIM insert or gave no amplification reaction from the non-recombinant vector. Of the twenty clones selected from the 384-well microtiter plate which had been automatically visually differentiated, none carried the 1.2 Kb HIP1 fragment. A similar experiment of clones manually selected and automatically picked from the Mata library confirmed that blue colonies contained the LexA insert from the pGAD427-LexA construct, and no automatically picked colonies carried this insert. The pBTM117c-HIP1 plasmid encoded for the LexA-HIP1 fusion protein, and the pGAD427-LexA encoded for the GAL4ad-lexA fusion protein were known to auto-activate the readout system without any partner protein. Hence, automatic visual differentiation has preselected against these false positive clones and automatically created a regular grid pattern of yeast clones expressing a single fusion protein unable to activate the readout system.

Example 9

Figure 21:
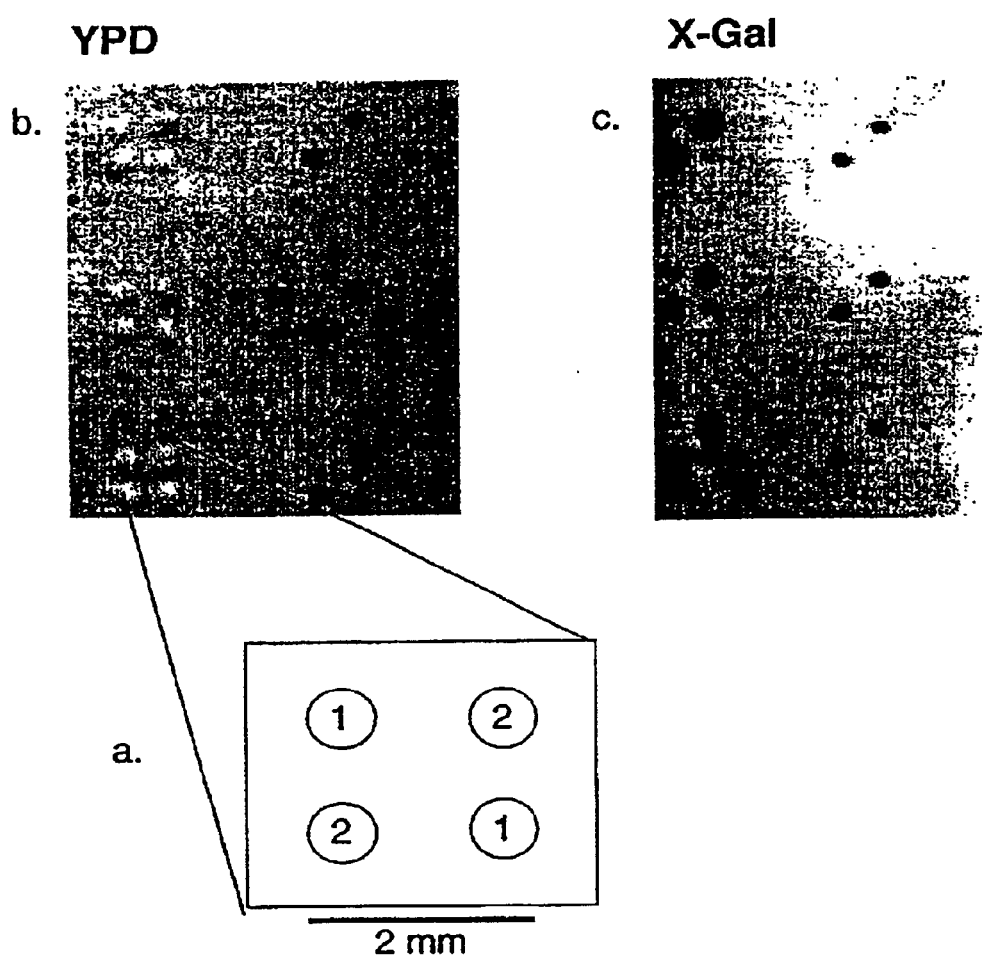

Automated Interaction Mating to Combine Genetic Elements in Yeast Cells 9.1 Automated Interaction Mating on a Solid Support in Regular Pattern The yeast strains that did not express auto-activating fusion proteins in section 8.1 were mated using an automated approach. Each of the yeast strains x1a, x2a, y1α and y2α was grown in every well of one of four microtiter plates containing SD-trp-ade medium for the Mata strains and SD-leu-ade medium for the Matα strains. Each plate was labelled with a unique barcode and using a spotting robot such as described by Lehrach et al. (1997), the yeast strains x1a and x2a were transferred in a defined 2×2 duplicate pattern with an inter-spot spacing of 2 mm to Hybond-N+ membrane (Amersham) which had been pre-soaked with YPD medium. The spotting robot then automatically transferred the yeast strains y1α and y2α to the same respective spotting positions on each membrane as, and already containing the x1a and x2a clones. The robot automatically sterilised the spotting tool, changed the microtiter plate between each set of clones transferred and created a data-file in which the spotting pattern produced and the barcode that had been automatically read from each microtiter plate was recorded. The spotted membranes were transferred to YPD plates and incubated for over night at 30° C. to allow mating and growth to occur. Each membrane was assayed for β-Gal activity using the method of Breeden & Nasmyth (1985) and was subsequently air dried overnight. A digital image of each dried filter was captured using a standard A3 computer scanner and image processed as described in section 4.1. The processed image was stored on computer and the identity of clones that expressed β-Galactosidase was determined using the image analysis system described in section 4.1. FIG. 21 shows the results of automated interaction mating between the strains x1a & y1a and x2a & y2a. Both resulting diploid strains grew on YPD media, yet only the diploid strain resulting from the interaction mating of x2α & y2α that contained plasmids encoding the interacting fusion proteins LexA-SIM1 & GAL4ad-ARNT respectively, showed a LacZ+phenotype and turned blue on incubation with X-Gal. No β-galactosidase activity was observed for the diploid strain resulting from the interaction mating between the strains x1a and y1α that contained plasmids encoding the proteins LexA and GAL4ad.

9.2 Automated Interaction Mating Based on Liquid Culture

Two defined libraries of clones which express fusion proteins were created. First, the yeast strain L40 ccu was transformed with the plasmid pLUA and a resulting stable transformant colony cultured in minimal medium lacking adenine. Cells from this culture were rendered competent and transformed with 3 µg pooled mixture of all six pBTM117c constructs shown in Table 2. Second, the yeast strain L0 ccuα was transformed with the plasmid pLUA and a resulting stable transformant colony cultured in minimal medium lacking adenine. Cells from this culture were rendered competent and transformed with 3 µg pooled mixture of all six pGAD427 constructs shown in Table 2. In all cases, competent cells were prepared and transformations conducted using the method of Schiestel & Gietz (1989).

The cells in the two resulting transformation mixes were allowed to recover by incubation at 30° C. in YPD liquid medium for 2 hours before plating onto large 24×24 cm agar trays (Genetix, UK). The Mata cells containing the pBTM117c fusion library were plated onto minimal medium lacking tryptophan and adenine but containing 0.2% 5-FOA (SD-trp-ade+FOA), while the Matα cells containing the pGAD427 fusion library were plated onto minimal medium lacking leucine and adenine but containing 0.2% 5-FOA (SD-leu-ade+FOA).

The colonies on the agar-trays were grown by incubation at 30° C. for 4 to 7 days. To minimise false positives arising from dormant cells, the colonies on the two agar-trays were replica-plated onto new agar-trays containing the same respective selective media as a given original tray using standard velvet replication. This replication procedure only transfered cells from the top of a growing colony and thus reduced the carry over of dormant cells and hence the number of false positive clones in the yeast two-hybrid system. These replica agar-trays were incubated at 30° C. for 4 to 7 days in order for the yeast cells to grow.

To conduct the liquid interaction mating, the resulting Mata and Matα colonies were separately collected off both replica trays by washing with 20 ml of liquid minimal medium. These two mixtures of yeast clones were carefully resuspended, pelleted and washed with sterile distilled water before incubation in 100 ml of YPD in order to ensure that the cells in both mixtures were mating competent. The two populations of mating competent cells were combined in 500 ml of YPD liquid media contained within a 10 litre flat bottomed flask and incubated at 30° C. with very gentle shaking (<60 rpm) overnight to allow interaction mating to proceed. The resulting mixture of diploid cells was pelleted by gentle centrifugation at 3000 rpm for 5 min, washed twice with 50 ml of sterile distilled water and finally, 10 ml of the resulting cell suspension was plated onto each of five 24×24 cm agar-trays containing 300 ml of minimal medium lacking leucine, trptophan, adenine, histidine and uracil (SD-leu-trp-ade-his-ura). The agar trays were poured using an agar-autoclave and pump (Integra, Switzerland) to minimise tray-to-tray variation in agar colour and depth. After plating, the colonies were grown by incubating the trays at 30° C. for 4 to 7 days.

After incubation, the resulting diploid yeast cells expressing interacting fusion proteins were automatically picked using our modified picking system as described in section 3.1 except that the picked clones were inoculated into microtiter plates containing the liquid selective medium SD-leu-trp-ade/7% glycerol. The interaction library comprising the diploid yeast cells contained in the microtiter plates were grown by incubation at 30° C. as described in section 3.1. Two further copies of the interaction library were made into new microtiter plates containing SD-leu-trp-ade/7% glycerol growth medium, all plates were individually labelled with a unique barcode and stored at −70° C. until required for further analysis as described in section 3.1.

It will be clear that higher density regular grid-patterns of such an interaction library can be easily generated by a person skilled in the art from these microtiter plates of diploid yeast cells by following the methods disclosed in sections 3.2, 3.3 and 3.4 of this invention. The creation of high-density regular grid patterns of diploid yeast cells can be conducted using the procedures as described in earlier sections. These arrays can be used to assay reporter gene activity, or for generation of nucleic acid arrays for hybridisation. Modifications to selective medium may be required which a person skilled in the art will recognise.

Example 10

Application of the Improved Two-Hybrid System to a Prokaryotic Two-Hybrid System 10.1 Strains, Readout Systems and Vectors Two *E. coli* strains KS1-OR2HF+ and KS1-OR2HF− were created that carry the sacB conterselective marker under the control of the placO$_1$2-62 promoter, and also the tetracycline selective gene under the control of a second placO$_R$2-62 promoter. Both strains have the sacB counterselective reporter gene stabley inserted within the *E. coli* chromosome by knock-out of the arabinose operon to enable arabinaose controlled inducible promoters to be utilised. The selective Tet. reporter gene is stabley inserted in within the chromosome by knock-out of the lactose operon which also enables a lacY counterselective marker to be utilised. Strain KS1-OR2HF⁺ was created by transformation of the fertility conferring F' plasmid into KS1-OR2HF⁻. KS1-OR2HF⁻ was created by site-specific knock-out and insertion of the sacB reporter gene construct into the arabinose operon of strain KS1-ORTet by transformation of the plasmid pKO3-araOrsacB and subsequent selection for stable insertions using the method of Link et al. (1997) pKO3-araOrsacB was prepared by blunt-ended ligation of a 1.4 Kb OrsacB fragment into Stu I digested pKO3-ARA to produce an insert of the OrsacB fragments flanked by 2.5 Kb bp and 1.0 Kb of the 3' and 5' ends of the *E. coli* arabinose operon respectively. pKO3-ARA carries the complete arabinose *E. coli* operon which had been amplified by PCR from *E. coli* genomic DNA using tailed primers, digested with Sal I and cloned into the Sal I site of pKO3 by standard procedures. The OrsacB fragment was created by ligating together PCR fragments of the placO$_R$2-62 promoter and the sacB gene. The placO$_R$2-62 promoter and sacB PCR fragments were amplifed using standard procedures and anchor primers which gave rise to complementary overhangs between the two consecutive fragments which were subsequently annealed to generate the chimeric sequence (see, for example, Current Protocols in Molecular Biology, Eds. Ausubel et al. John Wiley & Sons: 1992) from the plasmids KJ306-31 and pKO3. The lac promotor derivative placO$_R$2-62 carried by the plasmid KJ306-3 I was prepared by cleaving the plasmid KJ306 with Hinc II and inserting a 31 bp linker sequence (Dove et al. 1997). The strain KS1-ORTet was created by site-specific knock-out and insertion of a tetracycline reporter gene under the control of the placO$_R$2-62 promoter into the lactose operon of strain KS 1F also by genomic knock-out utilising the pKO3 system. The tetracycline gene was obtained by PCR of the plasmid pACYC184. Modifications to the above knock-out insertion method were made to make an appropriate pKO3 construct to enable the knock-out insertion of the chimeric tetracycline reporter gene into the lactose operon as will be possible by a person skilled in the art. The *E. coli* strain KS1F— was constructed from KS1 (Dove et al.) by removal of the F' plasmid using standard plasmid curing procedures.

Figure 22:
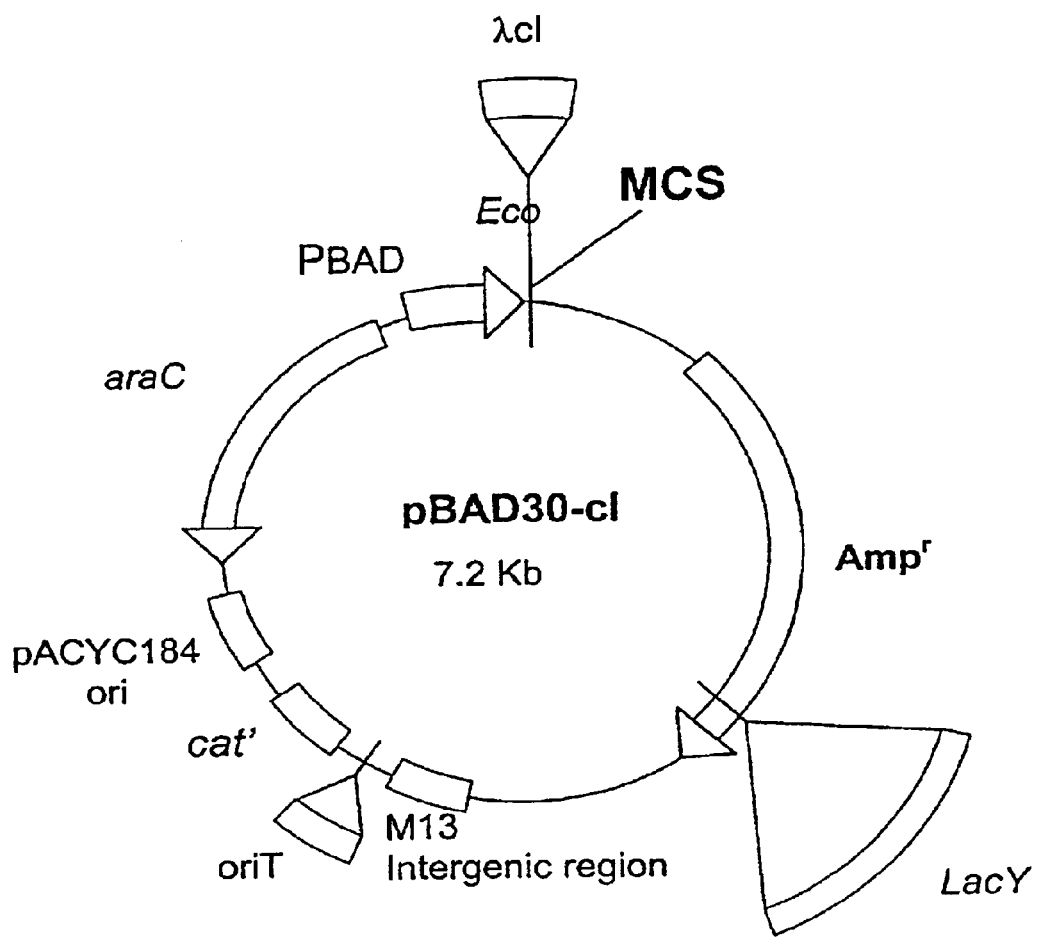

Two vectors, pBAD18-αRNAP and pBAD30-cI were constructed to provide further genetic features to enable the method of invention (FIG. 22). The vectors are based on the pBAD series of vectors which provide tight inductive control expression of cloned genes using the promoter from the arabinose operon (Guzman et al., 1995 J. Bact. 177: 4141–4130, and can be maintained in the same *E. coli* cell by virtue of compatible origins of replication. The plasmid pBAD18-αRNAP expresses under the control of the arabiose promoter, fusion proteins between the α amino terminal domain (NTD) of the α-subunit of RNA polymerase and DNA fragments cloned into the multiple cloning site. The presence of this plasmid in kanamycin sensitive cells can be selected by plating, on growth medium supplemented with kanamycin, or for its absence by the counterselective rpsL allele by plating on media supplemented with streptomycin (Murphy et al. 1995). The plasmid pBAD30-cI expresses under the control of the arabinose promoter, fusion proteins between the λcI protein and DNA fragments cloned into the multiple cloning site. The presence of this plasmid in amplicillin sensitive cells can be selected by plating on growth medium supplemented with amplicillin, or for its absence by the counterselective lacY gene by plating on media supplemented with 2-nitrophenyl-β-D-thiogalactosidase (tONPG) (Murphy et al. 1995). Additionally, the 288 bp oriT sequence enables unidirectional genetic exchange of the pBAD30-cI plasmid and its derivatives from *E. coli* cells containing the F' fertility factor to F⁻ stains lacking the fertility factor.

The plasmid pBAD18-αRNAP was constructed by cloning a 0.7 Kb DNA fragment encoding the α amino terminal domain (NTD) (residues 1–248) of the c-subunit of RNA polymerase (α-NTD) into Eco RI digested pBAD18-CS. The 0.7 Kb A-NTD fragment was =isolated by PCR from the plasmid pHTflα (Tang et al., 1994 Genes Dev 8: 3058–3067). The plasmid pBAD 18-CS was obtained by site-specific insertion assisted by PCR cloning of the 400 bp coding region and translational start site of the rpsL allele into pBAD18-Kan (Guzman et al 1995) before the transcriptional termination signal of the kanamycin gene to enable polycistronic transcription of the counterselective and selective markers. The rpsL allele was obtained by PCR amplification of the plasmid pNO1523 (Murphy et al. 1995).

The plasmid pBAD30-cI was constructed by cloning a 730 bp DNA fragment encoding the λcI protein into Eco RI digested pBAD30-TCS. The 730 bp fragment encoding the λcI protein was isolated by PCR from the plasmid pACλcI (Dove et al 1997). The plasmid pBAD30-TCS was obtained by site-specific insertion assisted by PCR cloning of the 1.3 Kb coding region and translational start site of the lacY gene into pBAD30-T before the transcriptional termination signal of the ampicillin gene to enable polycistronic transcription of the counterselective and selective markers. The lacY gene was obtained by PCR amplification of the plasmid pCM10 (Murphy et al. 1995). The plasmid pBAD30-T was obtained by site specific insertion of a 288 bp oriT sequence obtained by PCR from the F' plasmid between the M13 intergenic region and cat'locus of pBAD30 (Guzman et al 1995).

10.2 Detection and Identification of Interacting Proteins Using a Large-Scale and Automated Prokaryotic Two-Hybrid System Generation of a Libraries of *e. Coli* Cells Expressing Fusion Proteins The pSport1 plasmid extraction containing the amplified cDNA library of *Strongylocentrotus purpuratus* described in section 6.1 was used. Approximately 1 μg of the library inserts were then isolated from the plasmid DNA by Hind III/Sal 1 digestion and size selective (1–1.5 Kb) agarose gel purification using standard procedures.

The two plasmids pBAD18-αRNAP and pBAD30-cI were prepared by digestion with Hind 111Sal 1. The insert mixture that was isolated as above was split into two equal fractions and 300ng was ligated with 50 ng of each of the two prepared plasmids. Following ligation, the pBAD18-αRNAP reaction was then transformed into competent KS 1-OR2HF⁻ *E. coli* cells, and the pBAD30-cI was transformed into competent KS1-OR2HF⁺ *E. coli* cells.

Genetic Preselection Against False Positive Clones and the Automated Creation of a Regular Grid-Pattern of *e. Coli* Cells Expressing a Fusion Protein The two transformation mixes were plated onto large 24×24 cm agar trays (Genetix, UK) containing selective media. The F cells containing the pBAD18-αRNAP fusion library were plated onto LB selective medium supplemented with kanamycin (50 ug/ml), arabinose (0.2% w/v) and sucrose (5% w/v). The F+cells containing the pBAD30-cI fusion library were plated LB selective medium supplemented with amplicillin (100 ug/ml), arabinose (0.2%) and sucrose (5%). The agar trays were poured using an agar-autoclave and pump (Integra, Switzerland) to minimise tray-to-tray variation in agar colour and depth. After plating, the colonies were grown by incubating the trays at 37° C. for 18 to 24 hours. The E. coli cells expressed fusion proteins under the control of the arabinose promoter, and those cells expressing single fusion proteins able to auto-activate the sacB reporter gene were unable to grow, since expression of the sacB gene confers sensitivity to sucrose supplemented in the growth media at high concentrations.

Automated picking of E. coli clones for DNA analysis using vision-controlled robotic systems such as described in Lehrach et al. (1997) is well known in the art. Such systems should also be appropriate for the analysis of E. coli cells that express interacting or potentially interacting fusion proteins. Therefore, a laboratory picking robot was used to automatically pick individual E. coli colonies from the selective agar-trays into individual wells of a sterile 384-well microtiter plate (Genetix, UK) containing sterile liquid medium. The cells expressing the pBAD18-αRNAP fusion library were inoculated into liquid LB selective medium supplemented with kanamycin (50 ug/ml) and 10% (v/v) glycerol (LB+Kan/10% Gly), while the cells expressing the pBAD30-cI fusion library were inoculated into LB selective medium supplemented with amplicillin (100 ug/ml) and 10% (v/v) glycerol (LB+Amp/10% Gly). The resulting microtiter plates were incubated at 37° C. for 18 to 24 hours, and after growth of E. coli strains within the microtiter plates, each plate was labelled with a unique number and barcode. The plates were also replicated to create two additional copies using a sterile 384-pin plastic replicator (Genetix, UK) to transfer a small amount of cell material from each well into pre-labelled 384-well microtiter plates and pre-filled with the liquid selective medium containing 10% glycerol as was appropriate for the E. coli strain. The replicated plates were incubated at 37° C. for 18 to 24 hours, subsequently labelled, frozen and stored at −70° C. together with the original picked microtiter plates of the libraries of E. coli cells expressing fusion proteins.

In this manner, we generated a regular grid patterns of E. coli cells expressing fusion proteins using a robotic and automated picking system. 384-well microtiter plates have a well every 4.5 mm in a 16 by 24 well arrangement. Therefore, for each 384-well microtiter plate we automatically created a regular grid pattern at a density greater that 4 clones per square centimetre. It will be clear that higher density regular grid-patterns of such an interaction library can be easily generated by a person skilled in the art from these microtiter plates of E. coli cells by following the methods disclosed in sections 3.2, 3.3 and 3.4 of this invention. For example, densities of greater than 19 clones per square centimetre can be obtained by robotic pipetting of clones into wells of a 1536-well microtiter plate.

Visual Differentiation Against False Positive Clones and the Automated Creation of a Regular Grid-Pattern of e. Coli Cells Expressing a Fusion Protein To demonstrate that visual differentiation against cells that express single fusion proteins that auto-activate the readout system could be applied to a prokaryotic two-hybrid system, the libraries of fusion proteins described in section 10.2.1 were utilised. The two transformation mixes were plated onto large 24×24 cm agar trays (Genetix, UK) containing selective media The F⁻ cells containing the pBAD18-αRNAP fusion library were plated onto LB selective medium supplemented with kanamycin (50 ug/ml), arabinose (0.2%) and X-Gal (2 ug/ml). The F⁺ cells containing the pBAD30-cI fusion library were plated LB selective medium supplemented with amplicillin (100 ug/ml), arabinose (0.2%) and X-Gal (2 ug/ml). The agar trays were poured using an agar-autoclave and pump (Integra, Switzerland) to minimise tray-to-tray variation in agar colour and depth. After plating, the colonies were grown by incubating the trays at 37° C. for 18 to 24 hours and to allow any blue colour of colonies to develop. The E. coli cells expressed fusion protein under the control of the arabinose promoter, and those cells expressing fusion proteins able to auto-activate the lacZ reporter gene turned blue by enzymatic reaction of the X-Gal substrate as is well known in the art.

Using an automated picking system, white E. coli cells expressing single fusion proteins unable to activate the readout system were automatically visually differentiated from false positive E. coli cells that had turned blue and only white E. coli cells were arrayed in a regular grid pattern. A standard laboratory picking robot (Lehrach et al., 1997) was used except that the improvements relating to reliable sorting of white from blue yeast colonies as described in section 3.1 was also used to reliably discriminate between white and blue E. coli colonies. White E. coli colonies from the two sets of agar trays prepared above were automatically picked and inoculated into the appropriate selective media in 384-well microtiter plates as described in section 10.2. It will be recognised by a person skilled in the art that higher density regular grid patterns of these clones may easily be formed.

Automated Interaction Conjugation to Combine Genetic Elements in E. Coli Cells

It will be clear to a person skilled in the art that automated interaction mating on a solid support as described for yeast cells in section 9.1 is equally appropriate for E coli cells of different conjugation types that have been selected by the methods of genetic preselection or visual differentiation as disclosed in this invention. In such case, appropriate modifications to the selective media would be required. However, a person skilled in the art would be able to recognise and effect said modifications to the selective media by following the disclosures herein.

To demonstrate an automated approach to interaction conjugation based on liquid culture, two libraries of clones that express fusion proteins were prepared as described in section 10.1. The F⁻ cells containing the pBAD18-αRNAP fusion library were plated onto LB selective medium supplemented with kanamycin (50 ug/ml), arabinose (0.2%) and sucrose (5% w). The F+cells containing the pBAD30-cI fusion library were plated LB selective medium supplemented with ampicillin (100 ug/ml), arabinose (0.2%) and sucrose (5%).

To conduct the liquid interaction conjugation, the resulting F⁻ and F⁺ colonies were separately collected off the agar-trays by washing with 20 ml of liquid LB medium. These two mixtures of E. coli clones were carefully resuspended, pelleted and washed with LB. The two populations of cells were combined in 500 ml of LB liquid media and incubated at 37° C. with gentle shaking for 6 hours to allow interaction conjugation to proceed. The resulting mixture of E. coli cells was pelleted by gentle centrifugation at 3000 rpm for 5 min, washed twice with 50 ml of LB liquid media and finally, 10 ml of the resulting cell suspension was plated onto each of five 24×24 cm agar-trays containing 300 ml of the solid LB selective medium supplemented with ampicillin (100 ug/ml), kanamycin (50 ug/ml), arabinose (0.2%) and tetracycline (35 ug/ml) (LA+Amp+Kan+Tet+ara). The agar trays were poured using an agar-autoclave and pump (Integra, Switzerland) to minimise tray-to-tray variation in agar colour and depth. After plating, the colonies were grown by incubating the trays at 37° C. for 18 to 24 hours.

After incubation, resulting E. coli cells that expressed interacting fusion proteins grew on the surface of the selective agar, and were automatically picked using a laboratory picking system as described in section 10.2 except that picked clones were inoculated into microtiter plates containing the liquid LB medium supplemented with ampicillin (100 ug/ml), kanamycin (50 ug/ml) and 10% (v/v) glycerol (LB+Amp+Kan/10% Gly). The interaction library comprising the E. coli cells contained in the microtiter plates were grown by incubation at 37° C. for 18 to 24 hours. Two further copies of the interaction library were made into new microtiter plates containing LB+Amp+Kan/10% Glyc growth medium, all plates were individually labelled with a unique barcode and stored at −70° C. until required for further analysis as described above. It will be recognised by a person skilled in the art that higher density regular grid patterns of these clones may easily be formed.

Generation of a Regular Grid Pattern of Clones from an Interaction Library on Planar Carriers Using Automation A high-throughput spotting robot such as that described by Lehrach et al. (1997) was used to construct porous planar carriers with a high-density regular grid-pattern of E. coli clones from the defined interaction library contained within 384-well microtiter plates that is described above. The robot recorded the position of individual clones in the high-density grid-pattern by the use of a pre-defined duplicate spotting pattern and the barcode of the microtiter plate. Individually numbered membrane sheets sized 222×222 mm (Hybond N+, Amersham UK) were pre-soaked in LB medium, laid on a sheet of 3 MM filter paper (Whatmann, UK) also pre-soaked in LB medium and placed in the bed of the robot. The interaction library was automatically arrayed as replica copies onto the membranes using a 384-pin spotting tool affixed to the robot. Microtiter plates from the first copy of the interaction library were replica spotted in a '5×5 duplicate' pattern around a central ink guide-spot onto 10 nylon membranes—corresponding to positions for over 27,000 clones spotted at a density of over 100 spots per cm2. The robot created a data-file in which the spotting pattern produced and the barcode that had been automatically read from each microtiter plate was recorded.

Each membrane was carefully laid onto approximately 300 ml of solid agar media in 24×24 cm agar-trays. Six membranes were transferred to LB+Amp+Kan+Tet agar containing 0.2% arabinose and two each of the remaining membranes were transferred to either LB agar supplemented with kanamycin (50 ug/ml), arabinose (0.2%) and tONPG (1 mM) (LB+kan+ara+tONPG) or LB agar supplemented with amplicillin (100 ug/ml), arabinose (0.2%) and streptomycin (at an appropriate concentration for counterselction) (LB+Amp+ara+Sm). The E. coli colonies were allowed to grow on the surface of the membrane by incubation at 37° C. for 18 to 24 hours.

Detection of the Readout System in a Regular Grid Pattern

Two membranes from each of the selective media was processed to detect β-galacosidase activity using the method of Breeden & Nasmyth (1985) and a digital image was captured and stored on computer as described in section 4.1. Using the image analysis and computer systems described section 4.1, positive E. coli clones were identified by consideration of the activation state of the β-galactosidase readout system when clones had been grown on the various selective media. Positive clones were identified as those that turned blue after growth on the selective media LB+Amp+Kan+Tet+ara but not when grown on either of the counterselective media LB+Kan+ara+tONPG or LB+Amp+ara+Sm.

Identification of Individual Members of the Interaction

A positive E. coli clone (identified as 15F09) that expressed interacting fusion proteins as determined by the computer systems as described above, was recovered from a stored frozen copy of the interaction library. Both members comprising the interaction were recovered by specific PCR amplification of the insets carried by the pBAD18αRNAP and pBAD30-cI plasmids directly from the E. coli culture using plasmid-specific primers. Both members of the interaction were sequenced by standard procedures, and the information entered into a data-base as described in Example 7.

As described in section 4.1, high-density arrays of DNA representing interaction libraries or members comprising interaction libraries can be made by transfer to solid supports by a variety of means. To demonstrate the applicability of DNA hybridisation to identify E. coli clones carrying plasmids that encode for interacting fusion proteins, one membrane that had been taken from the LB+Amp+Kan+Tet+ara growth medium was processed to affix the DNA carried by the E. coli cells comprising the interaction library according to the method of Hoheisel et al (1991). The insert carried by the pBAD30-cI plasmid of clone 15F09 was radioactively labelled by the method of Feinberg & Vogelstein, (1983) and used as a hybridisation probe to the DNA array, and positive signals identified as described in section 4.1. A clone (22C 11) was identified as hybridising to the probe and was shown to be a positive clone by query of the data based described in section 4.1. In this manner, further steps in a protein—protein interaction pathway can be identified by hybridisation, consideration of reporter gene activation of hybridisation-positive clones and recovery of plasmids encoding members comprising these interactions. Recovery of the plasmids allows further investigation such as DNA sequencing to identify the members or repeated hybridisation to identify further steps in the protein—protein interaction pathway and hence develop protein—protein interaction networks as described in section 6.6.

Example 11

Application of the Improved Two-Hybrid System to a Mammalian Two-Hybrid System 11.1 Strains, Readout Systems and Vectors The human embryonic kidney fibroblast-derived cell line HEK 293 (or simply 293 cells) is especially suitable for mammalian 2H studies due to its high susceptibility for DNA during transfection (Graham, F. L. and Van der Eb, A. J. (1973), *Virol.* 54: 536–539; Graham, F. L., Smiley, J., Russel, W. C. and Naim, R. (1977), *J. Gen. Virol.* 36: 59–72). The cell line is available from ATCC.

Plasmids carrying teh mammalian readout systems named pG5E1bEGFPneo, pG5E1bEGFPhyg or pG5E1bEGFPpur are used. These plasmids contain the TATA element of the adenoviral E1b gene and five tandem copies of the GAL4 responsive element $UAS_G$ (5' CGGAGTACTGTCC TGCG 3' (SEQ ID No. 9)) (Sadowski, I., Ma, J., Treizenberg, S. and Ptashne, M. (1988), *Nature* 335: 559–560) positioned immediately upstream of the coding sequence for the enhanced green fluorescent protein (EGFP; Yang, T. T., Cheng, L. and Kain, S. R. (1996), *Nucl. Acids Res.* 24 (22): 4592–4593). These reporter plasmids are generated by replacing the coding sequence for CAT in G5E1bCAT (Dang, C. V., Barrett, J., Villa-Garcia, M., Resar, L. M. S., Kato, G. J. and Fearon, E. R. (1991), *Mol. Cell. Biol.* 11: 954–962) by the EGFP coding sequence and introducing either a neomycin, hygromycin or puromycin resistance marker gene (neo$^r$, hyg$^r$ or pur$^r$) using standard subcloning procedures.

The plasmids pMneo1,2,3 or pMhyg1,2,3, which are derived from pM1,2,3 (Sadowski, I., Bell, B., Broad, P. and Hollis, M. (1992), *Gene* 118: 137–141) by insertion of either neo$^r$ hyg$^r$ marker gene using standard subcloning procedures, are series (1,2,3 correspond to three possible reading frames) of improved Gal4p-fusion vectors derived from the pSG424 plasmid, which was designed for mammalian expression of fusion proteins that contain the DNA-binding domain of the yeast Gal4 protein (Sadowski, I. and Ptashne, M. (1989), *Nucl. Acids Res.* 17: 7539). This vector contains a polylinker preceded by coding sequences for Gal4p amino acids 1–147. Thus, a hybrid reading frame that encodes a Gal4p-fusion protein can be generated by inserting cDNA sequences into the polylinker region of pSG424/pM's. Transcripts of the hybrid reading frame are inititated from the SV40 early promoter and their processing is facilitated by the SV40 polyadenylation signal. Alternatively, the hybrid reading frames are subcloned into pLXSN or any other similar retroviral vector to allow packaging cell line-aided infection of target cells.

The plasmids pVP-Nconeo and pVP-Ncohyg are derived from pVP-Nco vector (Tsan, J., Wang, Z., Jin, Y., Hwang, L., Bash, R. O., Baer, R. The Yeast Two-Hybrid System, edn 1. Edited by Bartel, P. L., Fileds, S. New York: Oxford University Press (1997): 217–232) by insertion of either a neo$^r$ or hyg$^r$ marker gene using standard subcloning procedures. pVP-Nco in turn is an improved version of the pNLVP16 plasmid, which was constructed for the expression of herpes simplex virus protein VP16-fusion proteins in mammalian cells (Dang, C. V., Barrett, J., Villa-Garcia, M., Resar, L. M. S., Kato, G. J. and Fearon, E. R. (1991), *Mol. Cell. Biol.* 11: 954–962). A polylinker sequence is preceded by an artificial reading frame including the eleven amino-terminal residues of Gal4p (MKLLSSIEQAC (SEQ ID No. 10)), a nuclear localization signal from the SV40 large T antigen (PKKKRKVD (SEQ ID No. 11)) and the acidic transactivation domain (amino acids 411–456) of the VP16 protein. Alternatively, the hybrid reading frames comprising Gal4 (1–147) and individual sequences of a cDNA library are subcloned into pLXSN or any other similar retroviral vector to allow packaging cell line-aided infection of target cells.

11.2 Detection and Identification of Interacting Proteins

A number of monoclonal 293 cell lines stably containing the pG5E1bEGFPneo-, pG5E1bEGFPhyg or pG5E1bEGFPpur readout system are generated by the method of calcium phosphate transfection (Chen, C. and Okayama, H. (1987), *Mol. Cell. Biol.* 7:2745–2752), lipofectamine transfection or any other common transfection method, followed by selection in G418, hygromycinb (HygB) or puromycin containing medium, respectively. It is tested subsequently which particular clone is most appropriate (number of readout system copies and site(s) of integration into the host chromosomes may influence expression levels and inducibility of the reporter gene) for the method of invention.

The selected 293-G5E1bEGFPneo, 293-G5E1bEGFPhyg or 293-G5E1bEGFPpur reporter cell line is used as a "modified host cell strain" to perform the method of invention (detection and identification of interacting proteins).

Two pools representing all three reading frames of the two vector series pMneo or Mhyg and pVP-Nconeo or pVP-Ncohyg were prepared by Not 1/Sal 1 digestion and pooling of 1 µg each of vectors pMneo/pMhyg 1,2,3 and pVP-Nconeo/pVP-Ncohyg 1,2,3 respectively. 300 ng of a cDNA insert mixture that was isolated as described in section 6.1 was split into two equal fractions and was ligated with 50 ng of each prepared vector-series pool. Following ligation, each reaction was then separately transformed into electro-competent *E. coli* cells, and recombinant clones for each library were selected on five 24×24 cm plates ampicillin. Approximately 500 µg of the pVP-Nconeo/pVP-Ncohyg and 500 µg of the pMneo/pMhyg libraries were extracted from *E. coli* transformants by washing off the plated cells and a subsequent QiaPrep plasmid extraction of the wash mixture as described above. 16 µg of each vector was used to transfect a 10 cm plate of 293 cells.

11.3 Pre-Selection Against False Positives by Visual Differentiation

The pMneo1,2,3 or pMhyg1,2,3 plasmids containing the cDNA library fused to the Gal4-DNA binding domain were transfected into the selected 293 reporter cell line. For infection with retroviruses, designated packaging cell lines are transfected with the respective retroviral vectors and virus-containing supernatant from such cultures is then used to infect the reporter cell line (according to standard protocols; e.g. Redemann, N., Holzmann, v.Rüden, T., Wagner, E. F., Schlessinger, J. and Ullrich, A. (1992), *Mol. Cell. Biol.* 12: 491–498). Transfection and infection protocols can be optimized in a way to introduce on average only one plasmid per cell by adjusting the plasmid concentration for transfection or the virus titer during infection. Antibiotics G418 or HygB are employed to select for successfully transfected/infected reporter cells.

At this stage it is necessary to eliminate those cells that display a readout system activation as a consequence of only expressing a DNA-binding domain-fusion protein (in which case the fusion protein would be referred to as an "auto-activator"), instead of requiring an appropriate (interacting) transactivation domain-fusion protein to be coexpressed. Thus, the resultant polyclonal pool of stably transfected/infected reporter cells is then subjected to a preselection screen using the readout system to visually differentiate cells that express auto-activating fusion proteins. In the EGFP-based readout system cells expressing auto-activators can be identified by screening for expression of EGFP and consequently for the ability of the respective cells to emit a green fluorescent light (507 nm) upon stimulation with the appropriate excitatory wavelength (488 nm) (Yang, T. T., Cheng, L. and Kain, S. R. (1996), *Nucl. Acids Res.* 24 (22): 4592–4593). Monitoring readout system activation is either done by eye using a fluorescence microscope or by an automated detection device. The cells that activated the GRP reporter system were visually differentiated and sorted from otehr cells not actiavting the reporter system using a flouorescent assisted cell sorting deivce (FACS). Alternatively, elimination of false positive cells expressing auto-activators is either done manually or by removal/killing of cells by means of a suction pump or a micromanipulator or by a detector-linked automated system employing micromanipulator or a laser ablation device.

After elimination of cells that express autoactivating fusion proteins, the remaining polyclonal pool of 293 reporter cells expressing DNA-binding fusion proteins are then subjected to a second transfection/infection step as described above using pVP-Nconeo or pVP-Ncohyg plasmids or respective retroviral derivatives containing the cDNA library fused to the VP16 transactivator sequence. Selection for successfully transfected/infected cells employing antibiotics G418 or HygB is optional here. If selection is desired it has to be made sure that the resistance marker that forms part of the readout system is different from the marker genes on previously transfected/infected vectors. Addition of the antibiotics selecting for the second transfection/infection-vector may be necessary, if the subsequent screening/final selection procedures take several days to complete, in order to prevent loss/diluting out of the plasmids in the absence of selective pressure. A complete selection also eliminates cells that have not been successfully cotransfected (i.e. have not received a pVP-Nco-plasmid), although such cells would not be a major problem (as long as transfection/infection efficiency is high) because they would not be identified by the interaction screening anyway. It is also noteworthy that the longer the cells are kept in culture until cell lysis (and molecular analyses of the interacting proteins and their corresponding cDNA sequences) the more likely it is to loose cDNAs that encode for more or less toxic fusion proteins.

1.4 Automated Identification of Cells Expressing Interacting Proteins

The resulting polyclonal pool of doubly transfected reporter cells is then subjected to visual screening for interacting proteins as described for the visual preselection. Green fluorescent ("positive") cells, indicative of the expression of two interacting proteins were automatically sorted using a FACS system to arrange cells in a regualr grid pattern in wells of a mirotitre plate. Subsequently, single cell PCR and DNA sequencing was conducted to identify members comprising the interactions. Alternatively, the positive cells can be seeded onto a culture dish in a regular array/grid pattern. Cells might also be placed one by one into small wells of a multiwell dish and provided with an appropriate growth factor-supplemented medium or conditioned medium to allow the cells to survive and grow in isolation from other cells.

11.5 Double Preselection and Cell Fusion

The cotransfection protocol described above only includes a single preselection (instead of a double preselection). It does not include the possibility of a preselection against false positive clones arising from pVP-Nco (transactivation domain-cDNA fusion library) plasmids. Although the number of false positives from pVP-Nco plasmids is usually much lower than from pM1,2,3 (DNA binding domain-cDNA fusion library) plasmids, it may under some circumstances be necessary to apply a double preselection strategy.

To that end two different polyclonal pools of stable cell lines expressing either members of the pM- or pVP-Nco-cDNA fusion library are generated by transfection/infection of the 293 reporter cell line and selected by means of the respective (different) antibiotics (G418 and HygB) as described above. Both pools of cell lines are then subjected separately to preselection and elimination of false positive clones as detailed above.

In order to combine both fusion vectors and their corresponding expressed fusion proteins in one cell, individual cells of both pools of cell lines are fused together using state-of-the-art cell fusion-protocols involving PEG-facilitated electrofusion as described in Li, L.-H. and Hui, S. W. (1994), *Biophys. J.* 67: 2361–2366; Hui, S. W., Stoicheva, N. and Zhao, Y.-L. (1996), *Biophys. J.* 71: 1123–1130, and Stoicheva, N. and Hui, S. W. (1994), *Membrane Biol.* 140: 177–182. Fusions n between one cell of both pools is desired. For that purpose one cell of each pool is placed into each well of a multiwell dish as detailed above. After cell fusion, the combined cells are then subjected to visual selection. Cells are left on the same dish for visual or automated screening or collected and sorted by FACS.

11.6 Double Preselection and Cell Fusion Using an Inducible Expression System

A disadvantage of the above described double preselection method is that proteins with toxic or anti-proliferative effects and their corresponding cDNAs will be lost during the lengthy selection process necessary to establish polyclonal pools of stable cell lines for both cDNA-fusion library-sequences. In order to prevent elimination of cDNA sequences encoding for toxic/anti-proliferative proteins one can combine the double preselection strategy with the following inducible system.

The host cell strain is a 293 cell line which expresses a tetracycline (Tet)-controlled transactivator (tTA), which is a fusion of amino acids 1–207 of the tetracycline repressor (TetR) and the C-terminal activation domain (130 amino acids) of herpes simplex virus protein VP16. The cell line is called 293 Tet-Off as tTA is able to activate transcription from a Tet operator sequence (tetO)-controlled gene only in the absence of Tet. The reverse situation exists in the 293 Tet-On cell line, which stably expresses a reverse tTA ((r)tTA) that requires the presence of Tet to induce transcription from tetO-regulated genes. Both, 293 Tet-Off and 293 Tet-On cell lines are G418-resistant (neo$^r$). These cell lines are available through Clonetech Inc. tTA plasmids used to generate 293 Tet-Off and 293 Tet-On cell lines are described in Gossen, M. and Bujard, H. (1992), *Proc. Natl. Acad. Sci. USA* 89: 5547–5551 and in Gossen M., Freundlieb, S., Bender, G., Müller, G., Hillen, W. and Bujard, H. (1995), *Science* 268: 1766–1769.

293 Tet-On or -Off cell lines are then transfected with a readout system (described in 11.1.) and the reporter cell lines 293 Tet-On- or -Off-pG5E1bEGFPhyg/pur are generated through selection in G418 or HygB.

The sequences for the Gal4-DNA binding domain and for the SV40 nuclear localisation signal/VP16 transactivation domain (details and references as given in 11.1) are retrieved from pM and pVP-Nco plasmids and separately subcloned into the polylinker of pREV-TRE, a retroviral vector (Clonetech Inc.) to generate pREV-TRE-Gal4 and pREV-TRE-VP16. pREV-TRE contains the retroviral extended packaging signal, T+, which allows for production of infectious but replication-incompetent virus in conjunction with a packaging cell line such as PT67, followed by a hyg$^r$ gene (selectable marker) and seven copies of tetO fused to the cytomegalovirus (CMV) minimal promoter immediately 5' of the polylinker. Ψ+ and polylinker sequences are flanked by 5' and 3'LTRs, respectively. pREV-TRE is available from Clonetech Inc. cDNA libraries are subcloned into the polylinker of pREV-TRE.

The above described reporter cell lines are separately infected with either pREV-TRE-Gal4- or pREV-TRE-VP16derived retroviral particles. A polyclonal pool of new stable cell lines is selected in both cases using the resistance selection marker gene hyg$^r$. Transient expression of fusion proteins from pREV-TRE plasmids has to be induced by withdrawal (Tet-Off) or addition (Tet-On) of Tet in order to allow for double preselection and elimination of false positives as described above.

11.7 Cell Fusion and Selection for Cells Expressing Interacting Proteins

The remaining polyclonal pools of cell lines are then subjected to cell fusion as described above. The HygB concentration in the culture medium is increased to minimize a possible loss of either one component of the pairs of fusion protein cDNA sequences present in all fused cells. For the detection of positive clones, i.e. cells expressing a pair of interacting proteins (as detailed above), expression of fusion proteins has to be induced by addition or withdrawal of Tet.

REFERENCES

Allen, T. B., Walberg, M. W., Edwards, M. C., Elledge, S. J. (1995) Finding prospective partners in the library: the two-hybrid system and phage display find a match. TIBS, 20: 511–516

Anderson M. T., Tjioe I. M., Lorincz M. C. Parks D. R., Herzenberg L. A., Nolan G. P., Herzenberg L. A. (1996) Simultaneous fluorescence-activated cell sorter analysis of two distinct transcriptional elements within a single cell using engineered green fluorescent proteins. Proc. Natl. Acad. Sci. USA: 93: 8508–11

Barillo, E., Lacroix, B & Cohen, D (1991) Theoretical analysis of library screening using a N-dimensional pooling strategy. NAR 25: 6241–6247.

Bartel, P., Chien, C.-T., Sternglanz, R., Fields, S. (1993) Elimination of false positives that arise in using the two-hybrid system. Biotechniques 14: 920–924.

Bartel, P. L., Rothstein, J. A., SenGupta, D., Fields, S. (1996) A protein linkage map of *Escherichia coli* bacteriophage T7. Nat. Genet. 12: 72–77

Bendixen, C., Gangloff, S., Rothstein, R. (1994) A yeast mating-selection scheme for detection of protein—protein interactions. Nucl. Acids Res., 22: 1778–1779.

Benton, D. (1996) Bioinformatics—principles and potential of a new multidisciplinary tool. Trends in Biotechnology 14: 261–272.

Breeden, L. and K. Nasmyth, K. (1985). Regulation of yeast HO gene. *Cold Spring Harbor Symp. Quant. Biol.* 50: 643–650.

Boeke, J. D., LaCroute, F. and Fink, G. R. (1984). A positive selection for mutants lacing orotidine-5'-phosphate decarboxylase activitiy in yeast: 5-fluoro-orotic acid resistance. Mol. Gen. Genet. 197: 345–346

Cubbitt, A. B., Heim, R., Adams, S. R., Boyd, AE., Gross, L. A. and Tsien, R. Y. (1995). Understanding, improving and using green fluorescent proteins. *Trends Biochem. Sci.* 20: 448–455.

Davidson, 1986. Gene Activity in Early Development, Third Edition, Academic press, Orlando Fla.

DeRisi, J., Penland, L., Brown, P. O., Bittner, M. L., Meltzer, P. S., Ray, M., Chen, Y., Su, Y. A. and Trent J. M. (1996). Use of a cDNA microarray to analyse gene expression patterns in human cancer. Nat. Genet 14: 457–460.

Dove, S., Joung, J. K., Hochschild, A. (1997) Activation of prokaryotic transcription through arbitrary protein—protein contacts. Natur, 386:627–630

Dramanac, R., Labat, I., Brukner, I., Crkvenjakov, R. (1989) Sequencing of megabase plus DNA by hybridisation: theory of the method. Genomics, 4: 114–128.

Fearon, E., Finkel, T., Gillison, M. L., Kennedy, S. P., Casella, J. F., Tomaselli, G. F., Morrow, J. S., Van Dang, C. (1992) Karyoplasmic interaction selection strategy: A general strategy to detect protein—protein interactions in mammalian cells. Proc. Natl. Acad. Sci. USA, 89: 7958–7962.

Feinberg, A. P. and Vogelstein, B. (1983). A technique for radiolabelling DNA restriction endonuclease fragments to high specifity activity. *Anal. Biochem.* 132: 6–13

Fields, S. and Song, 0. (1989). A novel genetic system to detect protein—protein interactions. *Nature* 340: 245–246.

Fleischmann, R. D., Adams, M. D., (1995) Whole genome random sequencing and assembly of *Haemophiilus influenza* Rd. Science 269: 496–512.

Gietz, D., St. Jean, A., Woods, R. A., Schiestl, R. H. (1992) Improved method for high efficiency transformation of intact yeast cells. Nucleic Acids Research 20: 1425.

Gress, T. M., Më üller-Pillasche, F., Geng, M., Zimmerhack, F., Zehetner, G., Friess, H., Büchler, M., Adler, G., Lehrach, H. (1996) A cancer-specific expression profile. Oncogene 13: 1819–1830.

Han, L. and Colicelli, J. (1995). A human protein selected for interference with Ras function interacts directly with Ras and competes with Rafl. Mol. Cell. Biol. 15: 1318–1323.

Harper, J. W., Adami, G. R, Wei, N., Keyomarsi, K., Elledge, S. J. (1993) The p21 Cdk-interacting protein Cip1 is a potent inhibitor of G1 Cyclin-dependent kinases. Cell, 75: 805–816.

Hoffmann, W. (1985). Molecular characterisation of the CAN1 locus in *Saccharomyces cerevisiae*. *J. Biol. Chem.* 260:11831–11837.

Hoheisel, J. D., Lennon, G. G., Zehetner, G. & Lehrach, H 1991. Use of reference libraries of *Drosophila melanogaster* for relational data analysis; a step towards mapping and sequencing of the genome. J. Mol. Biol. 20: 903–914.

Hurd, D., Fallon, R. A., White, M., Jones, N. (1997) Improvements relating to assay systems. WO 97/23609

Johnson, R. F., Pickett, S. C., Barker, D. L. (1990) Autoradiography using storage phosphor technology. Electrophoresis 11: 355–360.

Kaeufer, N. F., Fried, H. M., Schwindinger, W. F., Jasin, M. and Warner, J. R. (1983). Cycloheximide resistance in yeast: the gene and its protein. *Nucleic Acids Res.* 11: 3123–3135.

Kawaguchi, Y., Okamoto, T., Taniwaki, M., Aizawa, M., Inoue, M., Katayama, S., Kawakami, H., Nakamura, S., Nishimura, M., Akiguchi, I., Kimura, J., Narumiya, S. and Kakizuka, A. (1994). CAG expansions in a novel gene for Machado-Joseph disease at chromosome 14q32.1. *Nat. Genet.* 8: 221–228.

Kietzmann, M., Kalkum, M., Maier, E., Bancroft., David, Eickhoff, H., Ivanov, I., Przewieslik, T., Horn, M. & Lehrach, H. (1997) Pizo-inkjet based pipetting-system for high density gridding and nanowell filling. Poster presentation at: *Automation in mapping and DNA sequencing*. EMBL Heidelberg, Mar. 16–19$^{th}$ 1997.

Larin, Z. and Lehrach, H. (1990). Yeast artificial chromosomes: an alternative approach to the molecular analysis of mouse developmental mutations. *Genet. Res.* 56: 203–208.

Lehrach, H., Bancroft, D. and Maier, E. (1997). Robotics, computing, and biology: An interdisciplinary approach to the analysis of complex genomes. *Interdisp. Science Rev.* 22: 37–43.

Le Douarin, B., Pierrat, B., vom Baur, E., Chambon, P, Losson, R. (1995) A new version of the two-hybrid assay for detection of protein—protein interactions. Nucl. Acids Res., 23: 876–878.

Lennon, G. G., Lehrach, H. (1991) Hybridisation analysis of arrayed cDNA libraries. Trends in Genetics 7: 375–388.

Li, M. (1997) Compounds and related methods for modulating potassium ion channels and assays for such compounds. WO 97/31112.

Li, J. J. and Herskowitz, 1. (1993). Isolation of ORC6, a component of the yeast origin recognition complex by a one-hybrid system. *Science* 262:1870–1874.

Link A. J., Phillips D. & Church G. M. (1997) Methods for generating precise deletions and insertions in the genome of wild-type *Escherichia coli*: application to open reading frame charcterisation. J Bacteriol 179:6228–6237

Liu, J. Stanton, VP, Fujiwara, TM, Wang, JX, Rezonzew, R. Crumley, MJ, Morgan, K, Gros, P., Housman, D. & Schurr, E (1995) large-scale cloning of human chromosome 2-specific yeast artificial chromosomes (YACs) using an interspersed repetitive sequences (IRS)—PCR approach. Genomics 26: 178–191.

Lockhart, D. J., Dong, H. Byme, M. C., Follettie, M. T., Gallo, M. V., Chee, M. S., Mittmann, M., Wang, C., Kobayashi, M., Horton, H. and Brown, E. L. (1996) Expression monitoring by hybridisation to high-density oligonucleotide arrays. nature Biotechnology 12: 1675–1680.

Maier, E., Maier-Ewert, S., Bancroft, D., Lehrach, H. (1997) Automated array technologies for gene expression profiling. Drug Discovery Today, 2: 315–324.

Meier-Ewert, S., Maier, E., Ahmadi, A., Curtis, J & Lehrach, H. (1993) An automated approach to generating expressed sequence catalogues. Nature 361: 375–376.

Murphy, C. K., Stewart, E. J. & Beckwith J. (1995) A double counter-selective system for the study of null allelels of essential genes in *Eschericia coli*. Gene 155: 1–7.

Nandabalan, K., Rothberg, J. M., Yang, M., Knight, J. R., Kalbfleisch, T. (1997) Identification and comparison of protein—protein interactions and inhibitors thereof, WO 97/47763

Pansegrau, W., Miele, L., Lurz, R. and Lanka E. (1987). Nucleotide sequence of the kanamycin resistance determinant of plasmid RP4: homology to other aminoglycoside 3'-phosphotransferases. *Plasmid* 18: 193–204.

Probst, M. R., Fan, C. M., Tessier-Lavigne, M. and Hankinson, 0. (1997). Two murine homologs of the *Drosophila* single-minded protein that interact with the mouse aryl hydrocarbon receptor nuclear translocator protein. *J. Biol. Chem.* 272: 4451–4457.

Putz, U., Skehel, P. and Kuhl, D. (1996). A tri-hybrid system for the analysis and detection of RNA-protein interactions. *Nucleic Acids Res.* 24: 4838–4840.

Ray BL, White CI, Haber JE (1991) Heteroduplex formation and mismatch repair of the "stuck" mutation during mating-type switching in *Saccharomyces cerevisiae*. Mol Cell Biol 11:5372–80

Ross, M. T., Hoheisel, J. D., Monaco, A. P., Larin, Z., Zehetner, G., & Lehrarch, H. (1992) High density gridded YAC filters: their potential as genome mapping tool. In: Anand, R (Ed.) Techniques for the analysis of complex genomes. Academic Press, New York, pp. 137–154.

Schiestl, R. H. and Gietz, R. D. (1989). High efficiency transformation of intact yeast cells using single stranded nucleic acids as a carrier. *Curr. Genet.* 16: 339–346.

Schober, A., Guenther, R. Schwienhorst, A., Doering, M. and Lindemann, B. F. (1993). Accurate high-speed liquid handling of very small biological samples. Biotechniques 15: 324–329.

SenGupta DJ., Zhang B., Kreamer B., Pochart P., Fields S., Wickens M. (1996). A three-hybrid system to detect RNA-protein interactions in vivo. *PNAS.* 93:8496–501

Shalon, D., Smith, S. J. and Brown, P. O. (1996). A DNA microarray system for analysing complex DNA samples using two-colour fluorescent probe hybridisation. Geneome Research 6, 639–645.

Sherman, F., Fink, G. R. & Hicks, J. B. Methods in Yeast Genetics. Cold Spring Harbor Laboratory, Cold Spring Harbor, N.Y.

Stanton, R., Jansee, A., Meinhof, C-G., Johnson, J., Giles, J. & Hamilton, S. (1995) Automating the mechanical subtraction of cDNA libraries. Presentation at the Third International Conference on Automation in Mapping and DNA Sequencing, Lawrence Berkeley National Laboratories, Berkeley, Calif. Nov. 5–8 1995.

Strauss, WM., Jaenisch, E & Jaenisch, R (1992) A strategy for rapid production and screening of yeast artificial chromosome libraries. Mamm. Genome 2: 150–157

Vidal, M., Boeke, J. D., Harlow, E. (1996a) Reverse two-hybrid system. WO 96/32503

Vidal, M., Brachmann, R. K., Fattaey, A., Harlow, E., Boeke, J. D. (1996b) Reverse two-hybrid and one-hybrid systems to detect dissociation of protein—protein and protein-DNA interactions. Proc. Natl. Acad. Sci. USA, 93: 10315–10320

Wanker, E. E., Rovira, C., Scherzinger, E., Hasenbank, R., Waelter, S., Tait, D., Colicelli, J. and Lehrach H. (1997). HIP-I: a huntingtin interacting protein isolated by the yeast two-hybrid system. *Hum. Mol. Genet.* 6: 487–495.

Went, G., (1996) Quantitative Expression Analysis$^{SM}$ of cancer: new prospects for discovery and Therapy guidance™. Presentation at Advances in Gene Amplification & detection: New technology, Research & Clinical Applications. The Ritz-Carlton, McLean, Virginia June 17–19

Wu, L. C., Wang, Z. W., Tsan, J. T., Spillman, M. A., Phung, A., Xu, X. L., Yang, M. C., Hwang, L. Y., Bowcock, A. M. and Baer, R. (1996). Identification of a RING protein that can interact in vivo with the BRCA1 gene product. *Nat. Genet.* 14: 430–440.

Yang, M., Wu, Z. and Fields (1995). Protein-peptide interactions analyzed with the yeast two-hybrid system. Nucleic Acids Res. 23:1152–1156

Zhang, J. and Lautar, S. (1996). A yeast three-hybrid method to clone ternary protein complex components. *Anal. Biochem* 242:68–72.

TABLE 1

Oligonucleotide adapters for the construction of the novel yeast two-hybrid vectors pBTM118 a, b and c and pGAD428 a, b and c.

| Oligonucleotide | Sequence (5'-3') |
| --- | --- |
| a sense | TCGAGTCGACGCGGCCGCTAA (SEQ ID No. 12) |
| A antisense | GGCCTTAGCGGCCGCGTCGAC (SEQ ID No. 13) |
| b sense | TCGAGGTCGACGCGGCCGCAGTAA (SEQ ID No. 14) |
| B antisense | GGCCTTACTGCGGCCGCGTCGACC (SEQ ID No. 15) |
| c sense | TCGAGAGTCGACGCGGCCGCTTAA (SEQ ID No. 16) |
| c antisense | GGCCTTAAGCGGCCGCGTCGACTC (SEQ ID No. 17) |

TABLE 2

Two-hybrid vectors used for the expression of fusion proteins.

| Plasmid | Fusion-protein | Insert (kb) | Counter-selection | Selection in yeast | Fusion protein Reference |
|---|---|---|---|---|---|
| PBTM117c | LexA | — | CAN1 | TRP1 | N/A |
| pBTM117c-HD1.6 | LexA-HD1.6 | 1.6 | CAN1 | TRP1 | Wanker et al., 1997 |
| pBTM117c-HD3.6 | LexA-HD3.6 | 3.6 | CAN1 | TRP1 | Wanker et al., 1997 |
| pBTM117c-SIM1 | LexA-SIM1 | 1.1 | CAN1 | TRP1 | Probst et al., 1997 |
| pBTM117c-MJD | LexA-MJD | 1.1 | CAN1 | TRP1 | this work |
| pBTM117c-HIP1 | LexA-HIP1 | 1.2 | CAN1 | TRP1 | this work |
| PGAD427 | GAL4ad | — | CYH2 | LEU2 | N/A |
| pGAD427-ARNT | GAL4ad-ARNT | 1.4 | CYH2 | LEU2 | Probst et al., 1997 |
| pGAD427-HIP1 | GAL4ad-HIP1 | 1.2 | CYH2 | LEU2 | Wanker et al., 1997 |
| pGAD427-HIPCT | GAL4ad-HIPCT | 0.5 | CYH2 | LEU2 | Wanker et al., 1997 |
| pGAD427-14-3-3 | GAL4ad-14-3-3 | 1.0 | CYH2 | LEU2 | this work |
| pGAD427-LexA | Gal4ad-LexA | 1.2 | CYH2 | LEU2 | this work |

TABLE 3

Yeast strains used for the 5-FOA counterselection and the automated interaction mating

| Strain | Plasmids | Selected on |
|---|---|---|
| x1a | pBTM117c/pLUA | SD-trp-ade |
| x2a | pBTM117c-SIM1/pLUA | SD-trp-ade |
| x3a | pBTM117c-HIP1/pLUA | SD-trp-ade |
| y1α | pGAD427/pLUA | SD-leu-ade |
| y2α | pGAD427-ARNT/pLUA | SD-leu-ade |
| y3α | pGAD427-LexA/pLUA | SD-leu-ade |

TABLE 4

Identification of fusion proteins that activate the URA3 readout system.

a.

| Strain | Plasmids | SD-trp-ade | SD-trp-ade + 5-FOA | SD-trp-ade-ura |
|---|---|---|---|---|
| x1a | pBTM117c/pLUA | + | + | − |
| x2a | pBTM117c-SIM1/pLUA | + | + | − |
| x3a | pBTM117c-HIP1/pLUA | + | − | + |

SD-trp-ade: Selective medium lacking tryptophan and adenine.
SD-trp-ade + 5-FOA: Selective medium containing 0.2% 5-FOA.
SD-trp-ade-ura: Selective medium lacking tryptophan, adenine and uracil.

TABLE 4-continued

Identification of fusion proteins that activate the URA3 readout system.

b.

| Strain | Plasmids | SD-leu-ade | SD-leu-ade + 5-FOA | SD-leu-ade-ura |
|---|---|---|---|---|
| y1α | pGAD427/pLUA | + | + | − |
| y2α | pGAD427-ARNT/pLUA | + | + | − |
| y3α | pGAD427-LexA/pLUA | + | − | + |

SD-leu-ade: Selective medium lacking leucin and adenine.
SD-leu-ade + 5-FOA: Selective medium containing 0.2% 5-FOA.
SD-leu-ade-ura: Selective medium lacking leucin, adenine and uracil.

TABLE 5

Identification of fusion proteins that activate the LacZ readout system.

A. L40ccu yeast cells transformed with pBTM117c plasmid constructs expressing a fusion protein comprising the LexA DNA binding domain are plated on minimal medium lacking trptophan, buffered to pH 7.0 with potassium phosphate and containing 2 ug/ml of X-Gal (SD-trp/XGAL): Results for the state of the readout system for various auto-activating and non-auto-activating fusion proteins

| Plasmid Construct | Fusion protein | Growth on SD-trp/XGAL | Blue colouration |
|---|---|---|---|
| pBTM117c | LexA | + | − |
| pBTM117c-HD1.6 | LexA-HD1.6 | + | − |
| pBTM117c-HD3.6 | LexA-HD3.6 | + | − |
| pBTM117c-SIM1 | LexA-SIM1 | + | − |
| pBTM117c-MJD | LexA-MJD | + | − |
| pBTM117c-HIP1 | LexA-HIP1 | + | + |

B. L40ccuα yeast cells transformed with pGAD427 plasmid constructs expressing a fusion protein comprising the GAL4ad activation domain are plated on minimal medium lacking leucine, buffered to pH 7.0 with potassium phosphate and containing 2 ug/ml of X-Gal (SD-leu/XGAL): Results for the state of the readout system for various auto-activating and non-auto-activating fusion proteins.

| Plasmid Construct | Fusion protein | Growth on SD-leu/XGAL | Blue colouration |
|---|---|---|---|
| pGAD427 | GAL4ad | + | − |
| PGAD427-ARNT | GAL4ad-ARNT | + | − |
| PGAD427-HIP1 | GAL4ad-HIP1 | + | − |
| PGAD427-HIPCT | GAL4ad-HIPCT | + | − |
| PGAD427-14-3-3 | GAL4ad-14-3-3 | + | − |
| PGAD427-LexA | Gal4ad-LexA | + | + |

We claim:

1. A method for reducing false positives in the identification of at least one member of a pair or complex of interacting molecules from potentially interacting molecules, comprising:

(A) providing at least one set of host cells, each set containing at least one genetic element comprising a selectable marker, said selectable marker being different between different sets of host cells, said genetic element comprising a nucleic acid encoding one of said potentially interacting molecules, said host cells further carrying a readout system that is activated upon the presence of auto-activating molecules;

(B) transferring at least one set of said host cells or progeny of at least one set of said host cells to at least one selective medium, different for each set of host cells, which allows growth of said host cells in the presence of said genetic element comprising a selectable marker and which precludes growth of said host cells upon auto-activation of said readout system, thereby selecting against host cells expressing a molecule able to auto-activate the readout system;

(C) combining in said host cells at least two said genetic elements, wherein at least one set of said host cells with one of said at least two genetic elements undergoes the selecting step as specified in (B);

(D) allowing at least one interaction between said potentially interacting molecules, if any, to occur;

(E) selecting for said interaction by transferring said host cells or progeny of said host cells to a selective medium that allows identification of said host cells upon activation of the readout system;

(F) identifying host cells that contain interacting molecules that activate said readout system on said selective medium;

(G) identifying at least one member of said pair or complex of interacting molecules; wherein said host cells are not yeast cells.

2. A method for reducing false positives in the identification of at least one member of a pair or complex of interacting molecules from potentially interacting molecules, comprising:

(A) providing at least one set of host cells, each set containing at least one genetic element comprising a selectable marker, said selectable marker being different between different sets of host cells, said genetic elements each comprising a nucleic acid encoding one of said potentially interacting molecules, said host cells further carrying a readout system that is activated upon the presence of auto-activating molecules;

(B) selecting against host cells expressing a molecule able to auto-activate the readout system by transferring at least one set of said host cells or progeny of at least one set of said host cells to at least one selective medium, different for each set of host cells, which allows growth of said host cells in the presence of said genetic element comprising a selectable marker and visual differentiation between those cells whose readout system has been activated from those host cells whose readout system has not been activated;

(C) combining in said host cells at least two different genetic elements, wherein at least one set of said host cells with one of said at least two genetic elements undergoes the selecting step as specified in (B);

(D) allowing at least one interaction between said potentially interacting molecules, if any, to occur;

(E) selecting for said interaction by transferring said host cells or progeny of said host cells to a selective medium that allows identification of said host cells upon activation of the readout system;

(F) identifying host cells that contain interacting molecules that activate said readout system on said selective medium;

(G) identifying at least one member of said pair or complex of interacting molecules.

3. The method of claim 1, wherein said pair or complex of interacting molecules is selected from RNA—RNA, RNA-DNA, RNA-protein, DNA—DNA, DNA-protein, protein-peptide, peptide—peptide or protein—protein interactions.

4. The method of claim 1, wherein said genetic element is a plasmid, artificial chromosome, virus or other extrachromosomal element.

5. The method of claim 1, wherein said interaction leads to the formation of a transcriptional activator that comprises a DNA-binding domain and a transactivating protein domain and is capable of activating a response moiety driving the activation of said readout system, wherein said DNA-binding domain and said transactivating protein domain are separately encoded by said at least two different genetic elements.

6. The method of claim 1, wherein said readout system comprises at least one counter-selectable gene.

7. The method of claim 6, wherein said counterselectable gene is one of the genes URA3, LYS2, sacB, CAN1, CYH2, rpsL, or lacY.

8. The method of claim 6, wherein the selective medium in step (B) comprises a counterselective compound.

9. The method of claim 8, wherein said counterselective compound is 5-fluoroorotic acid, canavanine, cycloheximide, sucrose, 2-nitrophenyl-β-D-thiogalactosidase (tONPG) or streptomycin.

10. The method of claim 2, wherein said readout system comprises or further comprises at least one detectable protein.

11. The method of claim 10, wherein said detectable protein is encoded from at least one of the genes lacZ, HIS3, URA3, LYS2, tetA, sacB, gfp (green fluorescent protein), yfp (yellow fluorescent protein), bfp (blue fluorescent protein), CAT (chloramphenicol acetyltransferase), luxAB, HPRT (hypoxanthine phosphoribosyltransferase), bla (β-lactamase), kan (kanamycin) or a surface marker.

12. The method of claim 1, wherein said host cells are bacterial cells, mammalian cells, insect cells or plant cells.

13. The method of claim 1, further comprising transforming, infecting or transfecting at least one set of host cells of said sets of host cells with said genetic element or genetic elements prior to step (D).

14. The method of claim 1, further comprising transforming, infecting or transfecting each set of host cells of said sets of host cells with said genetic elements prior to step (D).

15. The method of claim 1, further comprising transforming, infecting or transfecting one set of host cells of said sets of host cells with at least one genetic element prior to step (A), selecting against host cells in said one set of host cells expressing a molecule able to auto-activate said readout system as specified in step (B), and transforming, infecting or transfecting said set of host cells with at least one further genetic element in step (D).

16. The method of claim 1, wherein cell fusion, conjugation or interaction mating is used for the generation of said host cells with said genetic elements prior to step (D).

17. The method of claim 16, wherein said cell fusion, conjugation or interaction mating is affected or assisted by automation.

18. The method of claim 17, wherein said automation is effected by an automated process including picking, spotting, rearraying pipetting, micropipetting, or cell sorting.

19. The method of claim 18, wherein said process is effected by a picking robot, spotting robot, rearraying robot, pipetting system, micropipetting system or fluorescent assisted cell sorting (FACS) system.

20. The method of claim 1, wherein said selectable marker is an auxotrophic or antibiotic marker.

21. The method of claim 20, wherein said auxotrophic or antibiotic marker is LEU2, TRP1, URA3, ADE2, HIS3, LYS2, kan (kanamycin), bla (β-lactamase), Zeocin, neomycin, hygromycin, pyromycin or G418.

22. The method of claim 1, wherein host cells or progeny of host cells of step (D) are transferred to a storage compartment.

23. The method of claim 22, wherein the transfer to a storage compartment is effected or assisted by automation.

24. The method of claim 22 wherein the transfer to a storage compartment is effected by an automated process including arraying, replicating, picking, spotting, pipetting or micropipetting, or cell sorting.

25. The method of claim 24, wherein said process is effected by a picking robot, spotting robot, pipetting system, micropipetting system or fluorescent assisted cell sorting (FACS) system.

26. The method of claim 22, wherein said storage compartment comprises an anti-freeze agent.

27. The method of claim 22, wherein said storage compartment is at least one microtitre plate.

28. The method of claim 27, wherein said at least one microtitre plate comprises 96, 384, 846 or 1536 wells.

29. The method of claim 1, wherein the transfer of host cells or progeny of host cells in step (E) is effected or assisted by automation using a regular grid pattern.

30. The method of claim 29, wherein the transfer of host cells or progeny of host cells in step (E) is effected by an automated process including replicating, picking, spotting, pipetting or micropipetting, or cell sorting.

31. The method of claim 30, wherein said process is effected by a replicating robot, picking robot, spotting robot, pipetting system, micropipetting system or fluorescent assisted cell sorting (FACS) system.

32. The method of claim 29, wherein the transfer of host cells or progeny of host cells in step (E) is made by multiple transfers carrying additional host cells to the same position in said regular grid pattern.

33. The method of claim 1, wherein the transfer of host cells or progeny of host cells in step (E) is made to at least one carrier using a regular grid pattern.

34. The method of claim 33, wherein said at least one carrier is a microtitre plate and the regular grid pattern is at densities greater than 1 clone per square centimeter.

35. The method of claim 33, wherein said at least one carrier is a porous support and the regular grid pattern is at densities in the range of 1 to 10 clones per square centimeter.

36. The method of claim 33, wherein said at least one carrier is a non-porous support and the regular grid pattern is at densities in the range of 1 to 100 clones per square centimeter.

37. The method of claim 1 or claim 2, wherein the identification of host cells in step (F) for consideration of the activation state of said readout system is effected or assisted by an automated visual means.

38. The method of claim 1 or claim 2, wherein the identification of host cells in step (F) from consideration of the activation state of said readout system is effected or assisted by an automated process including digital image capture, digital storage, digital processing and/or digital analysis.

39. The method of claim 1, wherein the identification of said at least one member of said pair or complex of interacting molecules in step (G) is effected by nucleic acid hybridisation, oligonucleotide hybridisation, nucleic acid or protein sequencing, restriction digestion, spectrometry or antibody reactions.

40. The method of claim 1, wherein the identification of said at least one member of said pair or complex of interacting molecules in step (O) is effected using a regular grid pattern of said at least one member or of said nucleic acids encoding said at least one member.

41. The method of claim 40, wherein construction of regular grid patterns in step (G) is effected or assisted by automation.

42. The method of claim 41, wherein the automation is effected or assisted by an automated process including spotting, pipetting or micropipetting, or cell sorting.

43. The method of claim 42, wherein automation in step (G) is implemented by employing a spotting robot, spotting tool, pipetting system or micropipetting system.

44. The method of claim 40, wherein said identification is effected by an automated process including digital image capture, digital storage, digital processing and/or digital analysis.

45. The method of claim 1, wherein nucleic acid molecules, prior to said identification in step (G), are amplified by PCR or are amplified in a different host cell as a part of said genetic element or genetic elements.

46. The method of claim 1, further comprising:
(H) providing at least one of said genetic element in step (A), which additionally comprises or comprise a counter-selectable marker, wherein said counter-selectable markers are different for genetic elements associated with different sets of host cells;

(I) selecting for interaction by transferring host cells or progeny of host cells in step (E) to
  (i) at least one selective medium that precludes growth of host cells in the presence of the counter-selectable marker associated with said genetic element specified in (H) and allows growth in the presence of a selectable marker associated with another of said at least two genetic elements in step (C); and
  (ii) a further selective medium that allows identification of host cells upon activation of the readout system;
(J) identifying host cells in step (F) that contain interacting molecules that:
  (iii) do not activate said readout system on said at least one selective medium specified in (i); and
  (iv) activate said readout system on said selective medium specified in (ii).

47. The method of claim 46, wherein the genetic element that additionally comprises a counter-selectable marker further encodes an activation domain fusion protein.

48. The method of claim 1, further comprising:
(K) providing at least two of said genetic elements in step (A), which additionally comprise different counter-selectable markers;
(L) selecting for interaction by transferring host cells or progeny of host cells in step (E) to
  (v) at least one selective medium that precludes growth of host cells in the presence of the first counterselectable marker of the counterselectable markers specified in (K) and allows growth in the presence of a first selectable marker;
  (vi) at least one selective medium that precludes growth of host cells in the presence of the second counterselectable marker of the counterselectable markers specified in (K) and allows growth in the presence of a second selectable marker;
  (vii) a further selective medium that allows identification of said host cells upon activation of the readout system; and
(M) identifying host cells that contain molecules that:
  (viii) do not activate said readout system on said at least one selective medium specified in (v); and
  (ix) do not activate said readout system on said at least one selective medium specified in (vi); and
  (x) activate said readout system on said selective medium specified in (vii).

49. The method of claim 48, wherein said at least two genetic elements that additionally comprise a counter-selectable marker further encode a DNA binding domain fusion protein and an activation domain fusion protein, respectively.

50. The method of claim 46 or 48, wherein said counter-selectable marker or counter-selectable markers of step (H) or (K) are selected from the group of URA3, LYS2, sacB, CAN1, CYH2, rpsL or lacY.

51. The method of claim 46 or 48, wherein the transfer of host cells or progeny of host cells in step (I) or (L) is effected or assisted by automation.

52. The method of claim 51, wherein the said automation in step (I) or (L) is effected by an automated process including replicating, picking, spotting, pipetting or micropipetting, or cell sorting.

53. The method of claim 52, wherein said automation in step (I) or (L) is implemented by employing a replicating robot, picking robot, spotting robot, spotting tool, automated pipetting or micropipetting system, or fluorescent assisted cell sorting (FACS) system.

54. The method of claim 2, wherein said visual differentiation in step (B) is based on a difference between host cells in different activation states of the readout system which can be detected by visual means.

55. The method of claim 54, wherein said difference between host cells in different activation states that can be detected by visual means is brought about by activation of one of the genes lacZ, gfp (green fluorescent protein), yfp (yellow fluorescent protein), bfp (blue fluorescent protein), CAT (chloramphenicol acetyltransferase), luxAB, or of a surface marker.

56. The method of claim 54, wherein said visual means include digital image capture, digital storage, digital processing and/or digital analysis.

57. The method of claim 1, wherein said nucleic acid encoding one of said potentially interacting molecules is different for each host cell in a set of host cells or a majority of host cells in a set of host cells.

58. The method of claim 57, wherein said nucleic acid encoding one of said potentially interacting molecules is identical in not more than 10% of host cells in a set of host cells.

59. The method of claim 16, wherein cell fusion, conjugation or interaction mating is used for the generation of said host cells with said genetic elements in step (C).

60. The method of claim 34, wherein said regular grid pattern is at a density greater than 4 clones per square centimeter.

61. The method of claim 60, wherein said regular grid pattern is at a density greater than 10 clones per square centimeter.

62. The method of claim 61, wherein said regular grid pattern is at a density greater than 18 clones per square centimeter.

63. The method of claim 35, wherein said regular grid pattern is at a density in the range of 10 to 50 clones per square centimeter.

64. The method of claim 63, wherein said regular grid pattern is at a density in the range of 50 to 100 clones per square centimeter.

65. The method of claim 64, wherein said regular grid pattern is at a density in the range of greater than 100 clones per square centimeter.

66. The method of claim 36, wherein said regular grid pattern is at a density in the range of 100 to 500 clones per square centimeter.

67. The method of claim 66, wherein said regular grid pattern is at a density in the range of 500 to 1000 clones per square centimeter.

68. The method of claim 67, wherein said regular grid pattern is at a density in the range of greater than 1000 clones per square centimeter.

69. The method of claim 45, wherein the amplification is carried out in a bacterial host cell.

70. The method of claim 69, wherein the bacterial host cell is *E. coli*.

71. The method of claim 58, wherein said nucleic acid encoding one of said potentially interacting molecules is identical in not more than 5% of host cells in a set of host cells.

72. The method of claim 71, wherein said nucleic acid encoding one of said potentially interacting molecules is identical in not more than 2% of host cells in a set of host cells.

73. The method of claim 72, wherein said nucleic acid encoding one of said potentially interacting molecules is identical in not more than 1% of host cells in a set of host cells.

74. The method of claim 1, wherein in step (C), each set of host cells with one of said at least two genetic elements undergoes the selecting step as specified in (B).

75. The method of claim 2, wherein in step (C), each set of host cells with one of said at least two genetic elements undergoes the selecting step as specified in (B).

76. The method of claim 5, wherein in step (C), said DNA-binding domain is encoded by one of said at least two genetic elements undergone the selecting step as specified in (B).

\* \* \* \* \*

UNITED STATES PATENT AND TRADEMARK OFFICE
CERTIFICATE OF CORRECTION

PATENT NO. : 6,905,818 B1
DATED : June 14, 2005
INVENTOR(S) : Wanker et al.

It is certified that error appears in the above-identified patent and that said Letters Patent is hereby corrected as shown below:

Column 87,
Line 42, delete "O" and instead insert -- G --.

Signed and Sealed this

Twenty-ninth Day of November, 2005

JON W. DUDAS
*Director of the United States Patent and Trademark Office*

SEQUENCE LISTING

<160> NUMBER OF SEQ ID NOS: 17

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: polylinker

<400> SEQUENCE: 1
tcgagtcgac gcggccgcta accgg                                           25

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: polylinker

<400> SEQUENCE: 2
tcgaggtcga cgcggccgca gtaaccgg                                        28

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: polylinker

<400> SEQUENCE: 3
tcgagagtag acgcggccgc ttaaccgg                                        28

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 4
tcgtagatct tcgtcagcag                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 5
ggaattagct tggctgcagc                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 6
cgatgatgaa gatacccccac                                                20

<210> SEQ ID NO 7
<211> LENGTH: 21

-continued

```
<212> TYPE: DNA
<213> ORGANISM: Artificial Sequence
<220> FEATURE:
<223> OTHER INFORMATION: Description of Artificial Sequence: primer

<400> SEQUENCE: 7
gcacagttga agtgaacttg c                                              21

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence:
      oligonucleotide adapter

<400> SEQUENCE: 8
taagatcgcg acat                                                      14

<210> SEQ ID NO 9
<211> LENGTH: 17
<212> TYPE: DNA
<213> ORGANISM: Saccharomyces cerevisiae

<400> SEQUENCE: 9
cggagtactg tcctgcg                                                   17

<210> SEQ ID NO 10
<211> LENGTH: 11
<212> TYPE: PRT
<213> ORGANISM: Saccharomyces cerevisiae

<400> SEQUENCE: 10

Met Lys Leu Leu Ser Ser Ile Glu Gln Ala Cys
 1               5                  10

<210> SEQ ID NO 11
<211> LENGTH: 8
<212> TYPE: PRT
<213> ORGANISM: Simian virus 40

<400> SEQUENCE: 11

Pro Lys Lys Lys Arg Lys Val Asp
 1               5

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
tcgagtcgac gcggccgcta a                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
ggccttagcg gccgcgtcga c                                              21
```

```
<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
tcgaggtcga cgcggccgca gtaa                                             24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
ggccttactg cggccgcgtc gacc                                             24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
tcgagagtcg acgcggccgc ttaa                                             24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
ggccttaagc ggccgcgtcg actc                                             24
```